(12) United States Patent
Uber, III et al.

(10) Patent No.: US 9,056,200 B2
(45) Date of Patent: Jun. 16, 2015

(54) APPARATUS AND METHODS FOR DELIVERY OF FLUID INJECTION BOLUSES TO PATIENTS AND HANDLING HARMFUL FLUIDS

(75) Inventors: Arthur E. Uber, III, Pittsburgh, PA (US); Mark Trocki, Cheswick, PA (US); Marc A. Mabie, Pittsburgh, PA (US); Larry McCutchan, Allison Park, PA (US); L. George Siddoway, Pittsburgh, PA (US); Kevin P. Cowan, Allison Park, PA (US); Lisa M. Coates, Massillon, OH (US); John F. Kalafut, Pittsburgh, PA (US); Aaron Hughes, Masontown, PA (US); David M. Griffiths, Pittsburgh, PA (US); Peter Twichell, Cranberry, PA (US); Julie Gulick, Murrysville, PA (US); Frederick W. Trombley, III, Gibsonia, PA (US)

(73) Assignee: Bayer Medical Care Inc., Indianola, PA (US)

( * ) Notice: Subject to any disclaimer, the term of this patent is extended or adjusted under 35 U.S.C. 154(b) by 414 days.

(21) Appl. No.: 12/996,520

(22) PCT Filed: Jun. 5, 2009

(86) PCT No.: PCT/US2009/046437
§ 371 (c)(1),
(2), (4) Date: Dec. 6, 2010

(87) PCT Pub. No.: WO2009/149367
PCT Pub. Date: Dec. 10, 2009

(65) Prior Publication Data
US 2011/0209764 A1 Sep. 1, 2011

Related U.S. Application Data

(60) Provisional application No. 61/171,240, filed on Apr. 21, 2009, provisional application No. 61/153,070, filed on Feb. 17, 2009, provisional application No. 61/059,384, filed on Jun. 6, 2008.

(51) Int. Cl.
*A61N 5/00* (2006.01)
*A61N 5/10* (2006.01)
(Continued)

(52) U.S. Cl.
CPC .............. *A61N 5/1007* (2013.01); *A61M 5/007* (2013.01); *A61M 5/16827* (2013.01);
(Continued)

(58) Field of Classification Search
CPC .................. B01L 2200/027; B01L 2300/0864; B01L 3/5027; B01L 3/502746; B01L 3/502776; B01L 3/56; B01L 3/561; B01L 9/527; A61N 2005/1021; A61N 2005/1094; A61N 5/1002; A61N 5/1007
USPC ....................... 600/5; 137/1; 220/501; 604/19
See application file for complete search history.

(56) References Cited

U.S. PATENT DOCUMENTS

| 2,201,108 A | 5/1940 | Mahler |
| 3,718,138 A | 2/1973 | Alexandrov et al. |

(Continued)

FOREIGN PATENT DOCUMENTS

| EP | 0333276 | 9/1989 |
| EP | 1616587 | 1/2006 |

(Continued)

OTHER PUBLICATIONS

The Extended European Search Report dated Jun. 11, 2014 from corresponding EP Application No. EP09759525.
(Continued)

*Primary Examiner* — Christine H Matthews
*Assistant Examiner* — Sunita Reddy
(74) *Attorney, Agent, or Firm* — Joseph L. Kent; David Schramm; James R. Stevenson

(57) ABSTRACT

A hazardous fluid transport container and a hazardous fluid delivery system are disclosed. The hazardous fluid transport container includes a housing enclosing an at least partially shielded enclosure. First and second fluid path elements are disposed within the housing, with the first fluid path element and second fluid path element fluidly coupled together. A pump unit may be provided for dispensing fluid from the first and second fluid path elements optionally into a third fluid path element. Also, methods for priming the hazardous fluid transport container and for mitigating laminar flow injection bolus spreading are disclosed. Additionally, disclosed is a radioactive fluid transport container for a syringe or other container. The radioactive fluid transport container allows the syringe or container to be used in an injection procedure without removal from the container.

23 Claims, 24 Drawing Sheets

(51) Int. Cl.
*A61M 5/00* (2006.01)
*A61M 5/168* (2006.01)
*A61M 5/178* (2006.01)
*A61M 5/14* (2006.01)

(52) U.S. Cl.
CPC .... *A61M 5/1785* (2013.01); *A61M 2005/1402* (2013.01); *A61M 2202/0225* (2013.01); *A61M 2202/049* (2013.01); *A61M 2206/11* (2013.01); *A61M 2206/18* (2013.01)

(56) References Cited

U.S. PATENT DOCUMENTS

| | | |
|---|---|---|
| 3,984,695 A | 10/1976 | Collica et al. |
| 4,307,713 A | 12/1981 | Galkin et al. |
| 4,401,108 A | 8/1983 | Galkin et al. |
| 4,409,966 A | 10/1983 | Lambrecht et al. |
| 4,562,829 A | 1/1986 | Bergner |
| 4,585,009 A | 4/1986 | Barker et al. |
| 4,968,305 A | 11/1990 | Takahashi et al. |
| 4,994,012 A | 2/1991 | Nakayama et al. |
| 5,274,239 A | 12/1993 | Lane et al. |
| 5,472,403 A | 12/1995 | Cornacchia et al. |
| 5,514,071 A | 5/1996 | Sielaff, Jr. et al. |
| 5,559,324 A | 9/1996 | Rapkin et al. |
| 5,569,181 A | 10/1996 | Heilman et al. |
| 5,739,508 A | 4/1998 | Uber, III |
| 5,806,519 A | 9/1998 | Evans, III et al. |
| 5,810,988 A * | 9/1998 | Smith et al. ............... 204/666 |
| 5,927,351 A | 7/1999 | Zhu et al. |
| 6,162,198 A | 12/2000 | Coffey et al. |
| 6,425,174 B1 | 7/2002 | Reich |
| 6,453,188 B1 | 9/2002 | Ardenkjaer-Larsen et al. |
| 6,589,158 B2 | 7/2003 | Winkler |
| 6,767,319 B2 | 7/2004 | Reilly et al. |
| 6,773,373 B2 | 8/2004 | Henneken et al. |
| 7,018,363 B2 | 3/2006 | Cowan et al. |
| 7,105,846 B2 | 9/2006 | Eguchi |
| 7,151,267 B2 | 12/2006 | Lemer |
| 7,351,227 B2 | 4/2008 | Lemer |
| 7,457,804 B2 | 11/2008 | Uber, III et al. |
| 7,537,560 B2 | 5/2009 | Powers et al. |
| 2004/0015038 A1 | 1/2004 | Lemer |
| 2004/0064041 A1 | 4/2004 | Lazzaro et al. |
| 2004/0115038 A1 | 6/2004 | Nuesser et al. |
| 2004/0254525 A1 | 12/2004 | Uber, III et al. |
| 2004/0260143 A1 | 12/2004 | Reilly et al. |
| 2005/0085682 A1 | 4/2005 | Sasaki et al. |
| 2005/0107698 A1 | 5/2005 | Powers et al. |
| 2005/0113754 A1 | 5/2005 | Cowan |
| 2005/0203329 A1 | 9/2005 | Muto et al. |
| 2005/0203330 A1 | 9/2005 | Muto et al. |
| 2005/0277833 A1 | 12/2005 | Williams, Jr. |
| 2006/0051531 A1 | 3/2006 | Kashiwamura |
| 2006/0151048 A1 | 7/2006 | Tochon-Danguy et al. |
| 2008/0038839 A1 | 2/2008 | Linder et al. |
| 2008/0131362 A1 | 6/2008 | Rousso et al. |
| 2008/0177126 A1 | 7/2008 | Tate et al. |
| 2008/0242915 A1 | 10/2008 | Jackson et al. |
| 2009/0131862 A1 | 5/2009 | Buck et al. |

FOREIGN PATENT DOCUMENTS

| | | |
|---|---|---|
| JP | SHO60-236079 | 11/1985 |
| JP | 2000350783 | 12/2000 |
| JP | 2002-341040 | 11/2002 |
| JP | 2004290455 | 10/2004 |
| JP | 2005024291 | 1/2005 |
| JP | 2005283431 | 10/2005 |
| WO | 2004004787 | 1/2004 |
| WO | 2007010534 | 1/2007 |
| WO | 2008011401 | 1/2008 |
| WO | 2008083313 | 7/2008 |
| WO | 2009014367 | 1/2009 |

OTHER PUBLICATIONS

Ictal SPECT Using an Attachable Automated Injector: Clinical Usefulness in the Prediction of Ictal Onset Zone, Lee et al., Informa Healthcare, Acta Radiologica, pp. 1160-1168, 2009.
Automatic and Remote Controlled Ictal SPECT Injection for Seizure Focus Localization by Use of a Commercial Contrast Agent Application Pump, Feichtinger, et al., Blackwell Publishing Inc., pp. 1409-1413, 2007.
Counterpart European Search Report EP10015627 Jun. 16, 2011.
Counterpart Partial European Search Report EP10015627, Mar. 23, 2011.
International Search Report from counterpart PCT Application No. PCT/US09/46437 dated Aug. 11, 2009.

* cited by examiner

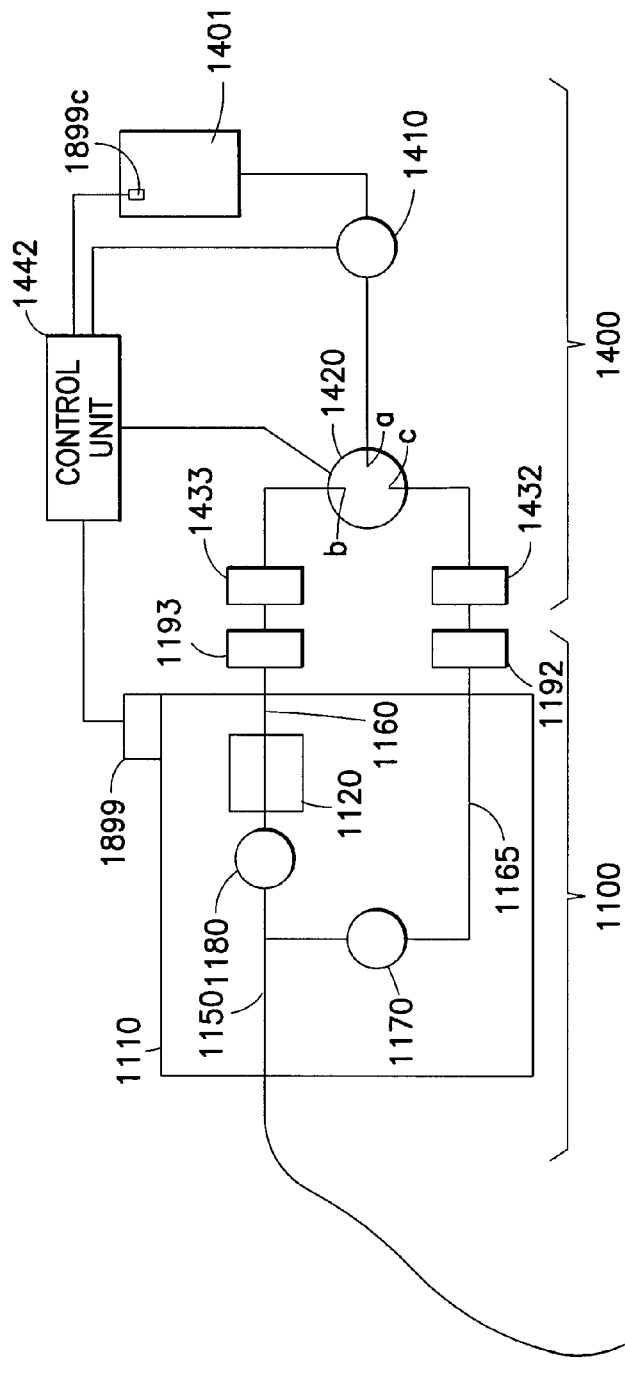
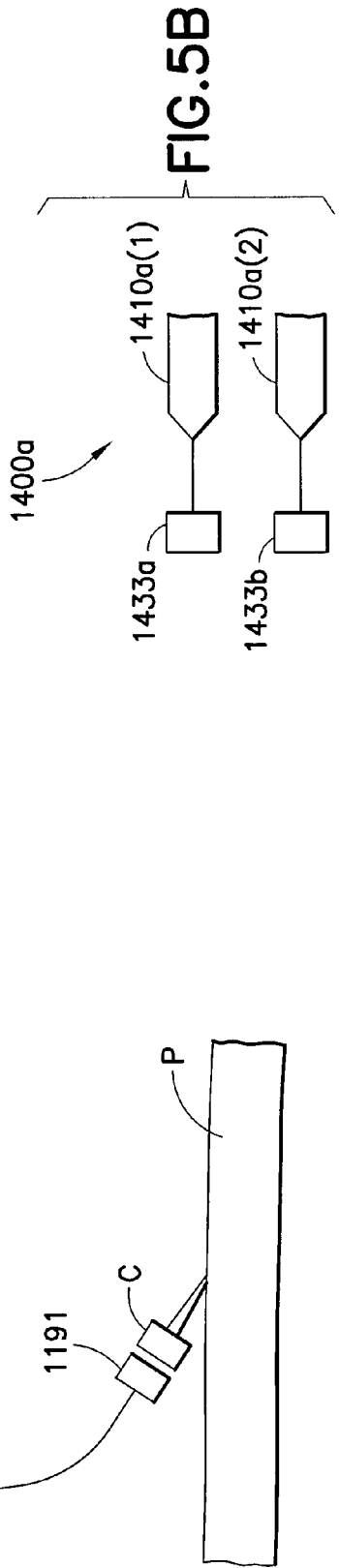
FIG.5A
FIG.5B

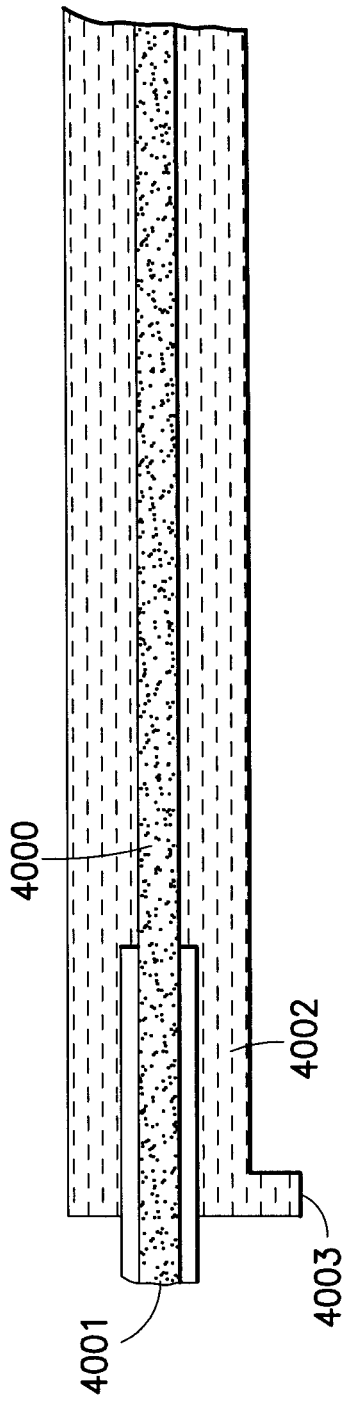
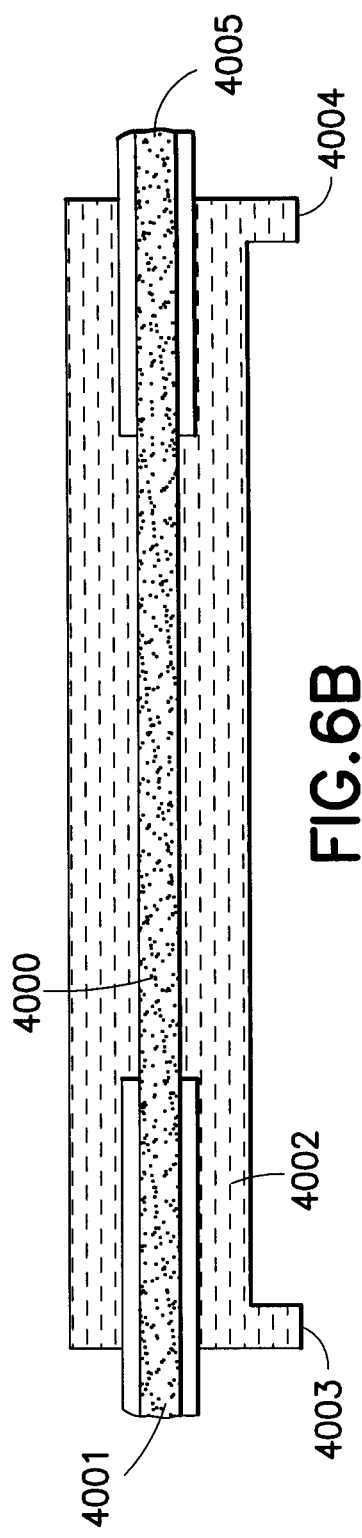

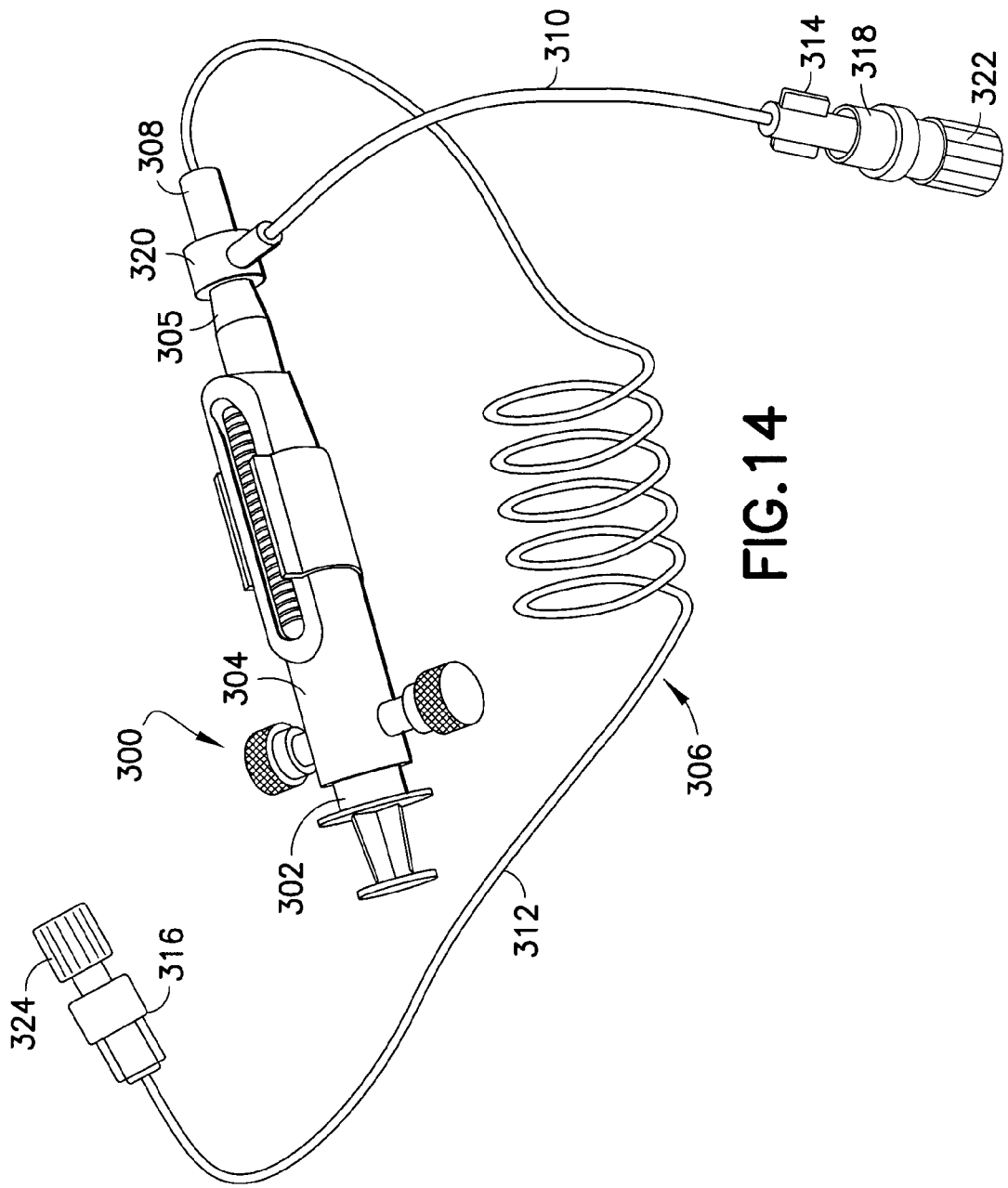

APPARATUS AND METHODS FOR DELIVERY OF FLUID INJECTION BOLUSES TO PATIENTS AND HANDLING HARMFUL FLUIDS

CROSS REFERENCE TO RELATED APPLICATIONS

This application claims the benefit of: U.S. Patent Application No. 61/171,240 filed Apr. 21, 2009 entitled "Apparatus and Methods for Delivery of Fluid Injection Boluses to Patients and Handling Harmful Fluids"; U.S. Patent Application No. 61/153,070 filed Feb. 17, 2009 entitled "Apparatus and Methods for Delivery of Fluid Injection Boluses to Patients and Handling Harmful Fluids"; and U.S. Patent Application No. 61/059,384 filed Jun. 6, 2008 entitled "Apparatus and Methods for Delivery of Fluid Injection Boluses to Patients".

This application also incorporates by reference International Application No. PCT/US07/89101 (WO 2008/083313), filed Dec. 28, 2007 and entitled "Methods and Systems for Integrated Radiopharmaceutical Generation, Preparation, Transportation, and Administration", which claims the benefit of U.S. Provisional Patent Application No. 60/910,810 entitled "Methods and Systems for Integrated Radiopharmaceutical Generation, Preparation, and Administration" filed Apr. 9, 2007 and, further, claims the benefit of U.S. Provisional Patent Application No. 60/878,334 entitled "Methods and Equipment for Handling Radiopharmaceuticals" and U.S. Provisional Patent Application No. 60/878,333 entitled "Pharmaceutical Dosing Method", both filed Jan. 1, 2007.

BACKGROUND OF THE INVENTION

1. Field of the Invention

The invention disclosed herein relates to handling and administration of pharmaceutical substances, typically intrinsically harmful or toxic pharmaceutical substances such as radioactive pharmaceutical substances, generally known as radiopharmaceuticals, to human and animal subjects and, more specifically, to apparatus and methods and associated components for the handling and administration of fluid radiopharmaceutical substances to human and animal subjects. Also included are methods and apparatus for handling and administration of chemotherapeutic agents and other fluids delivered to human and animal subjects.

2. Description of Related Art

Administration of radioactive pharmaceutical substances or drugs, generally termed radiopharmaceuticals, is often used in the medical field to provide information or imagery of internal body structures and/or functions including, but not limited to, bone, vasculature, organs and organ systems, and other tissue. Additionally, such radiopharmaceuticals may be used as therapeutic agents to kill or inhibit the growth of targeted cells or tissue, such as cancer cells. However, radiopharmaceutical agents used in imaging procedures and therapeutic procedures typically include highly radioactive nuclides of short half-lives and are hazardous to attending medical personnel. These agents are toxic and can have physical and/or chemical effects for attending medical personnel such as clinicians, imaging technicians, nurses, and pharmacists. Excessive radiation exposure is harmful to attending medical personnel due to their occupational repeated exposure to the radiopharmaceuticals. However, due to the short half-life of typical radiopharmaceutical agents and small applied dosages, the radiation exposure risk to benefit ratio for individual patients is acceptable. The constant and repeated exposure of medical personnel to radiation from radiopharmaceuticals over an extended period of time is a significant problem in the nuclear medicine field.

A number of techniques are used in the medical field to reduce radiation exposure to attending medical personnel associated with the creation, handling, transport, dose preparation, and administration of radiopharmaceuticals to patients. These techniques encompass one or more of minimizing the time of exposure of medical personnel, maintaining distance between medical personnel and the source of radiation, and/or shielding medical personnel from the source of radiation. As a certain amount of close-proximity interfacing between medical personnel and radiopharmaceutical agents (including patients who have or are to receive radiopharmaceutical agents) is somewhat inevitable during the current practice of generating, preparing, and administering radiopharmaceutical agents to patients and caring for these patients, radiation shielding has considerable importance in the nuclear medicine field. A simple patient radiation guard is disclosed in U.S. Pat. No. 3,984,695 to Collica et al. as an example. It is well-known to use shielded containers known as "pigs" for general handling and transport of radiopharmaceutical containers (bottles, vials, etc.) and use shielded syringes to remove the radiopharmaceutical from the radiopharmaceutical containers and administer the same to individual patients. Radiopharmaceutical transport pigs are also configured to transport syringes. Examples of shielded transport pigs are disclosed in U.S. Pat. No. 5,274,239 to Lane et al. which is incorporated by reference and U.S. Pat. No. 6,425,174 to Reich, also incorporated herein by reference. An example of a shielded syringe is disclosed in U.S. Pat. No. 4,307,713 to Galkin et al. which is also incorporated herein by reference. Other shielded syringes are known from U.S. Pat. No. 6,589,158 to Winkler; U.S. Pat. No. 7,351,227 to Lemer; and U.S. Pat. No. 6,162,198 to Coffey et al., all incorporated herein by reference.

As is generally known in the nuclear medicine field, radiation emanates in all directions from radioactive substances and, consequently, emanates in all directions from an unshielded container holding a radioactive substance. While radiation may be scattered or deflected, it is generally sufficient to protect personnel from the direct "shine" of radiation, unless the activity levels in the container are very high. Transport pigs come in various configurations for holding radiopharmaceutical containers (bottles, vials, syringes, etc.). One form often includes a removable cover that allows access to the held radiopharmaceutical container, as disclosed in U.S. Pat. No. 7,537,560 to Powers et al. incorporated herein by reference. Such containers may be in the form of a vial with an elastomeric, for example rubber, stopper or septum which retains the radiopharmaceutical agent in the vial. When the pig cover is in place, the radiation exposure is acceptable. When the cover is opened or removed, a radiation "shine" emanates from the opening. A common sterile transfer procedure to remove the radiopharmaceutical agent from its container is to pierce the elastomeric stopper or septum with a sterile needle on a syringe. Commonly, the exposed surface of the stopper or septum is sterilized with an alcohol wipe prior to piercing the stopper or septum with the transfer needle on the syringe. Commonly, this is also done in a clean hood and following the procedures recommended in Pharmacopeia <797>.

Syringes, during loading and once loaded with radiopharmaceutical agents, are commonly handled via syringe shields and shielded glove boxes or containers, but may also be transported in a suitably configured transport pig as noted previously. Syringe shields are commonly hollow cylindrical structures that accommodate the cylindrical body of the syringe and are constructed of lead or tungsten with a lead glass window that allows the handler to view the syringe plunger and liquid volume within the syringe. Due to its cylindrical configuration, syringe shields protect against radiation emissions in a generally radial direction along the length of the syringe body but the two open ends of the syringe shield provide no protection to the handler as there is radiation "shine" emanating from the two ends of the syringe shield. Devices are further known for drawing radiopharmaceutical agents into syringes. For example, U.S. Pat. No. 5,927,351 to Zhu et al. discloses a drawing station for handling radiopharmaceuticals for use in syringes, and is incorporated herein by reference. In radiopharmaceutical delivery applications, devices are known for remotely administering radioactive substances from syringes to minimize radiation exposures to attending medical personnel as disclosed in U.S. Pat. No. 5,514,071 to Sielaff Jr. et al. or U.S. Pat. No. 3,718,138 to Alexandrov et al. An automated device for controlled administering radioactive substances is disclosed in U.S. Pat. No. 5,472,403 to Cornacchia et al., incorporated herein by reference. A system approach to controlling injectors used to inject radioactive material into a patient is disclosed in published United States Patent Application Publication No. 2008/0242915.

In addition to the difficulties introduced by the hazardous nature of radiopharmaceuticals, the short half-lives of such radiopharmaceuticals further complicate the administration of a proper dosage to a patient. The radioactivity levels of the radiopharmaceutical agents used as tracers in, for instance, single-photon emission computerized tomography (SPECT) and positron emission tomography (PET) imaging procedures are measured by medical personnel, such as radiopharmacists or nuclear medicine technologists, to determine the radiation dose that will be administered to the individual during the course of a diagnostic procedure. The radiation dose received depends on a number of factors including the half-life of the radiopharmaceutical agent and the initial radioactivity level of the radiopharmaceutical agent at the time it is injected into the individual. One known solution is to measure or calibrate the initial radioactivity of the radiopharmaceutical and time the injection so that a dose of the desired level of radioactivity is delivered (as calculated from the half-life of the radiopharmaceutical). Often, radiation levels are determined as part of the dispensing or container filling process as disclosed generally in United States Patent Application Publication No. 2006/0151048 to Tochon-Ganguy et al. or measured by a stand-alone device adapted to receive the radiopharmaceutical container as disclosed in U.S. Pat. No. 7,151,267 to Lerner or U.S. Pat. No. 7,105,846 to Eguchi. Radiation detectors have also been placed upon syringe shields and in-line with the radiopharmaceutical delivery system. For example, U.S. Pat. No. 4,401,108 to Galkin et al. discloses a syringe shield for use during drawing, calibration, and injection of radiopharmaceuticals. This syringe shield includes a radiation detector for detecting and calibrating the radioactive dosage of the radiopharmaceutical drawn into the syringe. A similar arrangement to that disclosed by Galkin et al. but in connection with a transport pig is disclosed in Japanese Publication No. JP 2005-283431, assigned to Sumitomo Heavy Industries. U.S. Pat. Nos. 4,562,829 and 4,585,009 to Bergner and Barker et al., respectively, and incorporated herein by reference disclose strontium-rubidium infusion systems and a dosimetry system for use therein. The infusion system includes a generator of the strontium-rubidium radiopharmaceutical in fluid connection with a syringe used to supply pressurized saline. Saline pumped through the strontium-rubidium generator exits the generator either to the patient or to waste collection. Tubing in line between the generator and the patient passes in front of a dosimetry probe to count the number of disintegrations that occur. As the geometric efficiency (or calibration) of the detector, the flow rate through the tubing, and volume of the tubing is known, it is possible to measure the total activity delivered to the patient (for example, in milliCuries). Likewise, radiation measurements have been made upon blood flowing through the patient. For example, U.S. Pat. No. 4,409,966 to Lambrecht et al. discloses shunting of blood flow from a patient through a radiation detector. Information about nuclear medicine imaging devices and procedures can be found in PCT Application Publication No. WO 2006/051531 A2 and in PCT Application Publication No. WO 2007/010534 A2 assigned to Spectrum Dynamics LLC., both incorporated herein by reference. A portable fluid delivery unit is known from U.S. Pat. No. 6,773,673 to Layfield et al., incorporated herein by reference.

As noted above, examples of the use of radiopharmaceutical agents in diagnostic imaging procedures include positron emission tomography (PET) and single-photon emission computerized tomography (SPECT) which are noninvasive, three-dimensional imaging procedures that provide information regarding physiological and biochemical processes in patients. In effect, the radiopharmaceutical agent acts as a tracer to interact with the targeted area. An initial step in producing PET images or SPECT images of, for example, vasculature, organs and organ systems, tumors, and/or other targeted tissue is to inject the patient with a dose of the radiopharmaceutical agent. The radiopharmaceutical agent is absorbed on or by certain tissue or cells in the body structure of interest and concentrates in this area. As an example, fluorodeoxyglucose (FDG) is a slight modification to the normal molecule of glucose, the basic energy fuel of cells, which readily accepts a radionuclide as a replacement to one of the atoms of the molecule. FDG tends to be preferentially taken up by cells with higher metabolism, such as some cancer cells, inflammation, active muscles, or active neurons. The radiopharmaceutical "tracer" emits a positron which creates photons that can be detected as the tissue is scanned at various angles and the photons pass through a detector array. A computer is used to reconstruct a three-dimensional color tracer image of the selected tissue structure.

With the foregoing background in place, exemplary current practice of generating, preparing, and administration of radiopharmaceuticals will now be described. Typical radiopharmaceutical treatment practice in the United States includes having the radiopharmaceutical agent initially generated off-site from a treatment location, typically a hospital, by an outside nuclear medicine facility and then delivered to the treatment location for further preparation, for example, individual dosing and administration. The treatment location, for example, a hospital, orders specific radioactive substances to be ready at a specific time for a specific patient. These substances are prepared by the outside nuclear medicine facility and with sufficient radioactivity that they will have the desired radioactivity level at the targeted time. For example, the outside nuclear medicine provider may have a facility equipped with a cyclotron or radioisotope generator in, for example, a lead-shielded enclosure wherein the radiopharmaceutical agent, namely, a radioactive isotope is generated or created. Further refining or dose preparation steps, namely, placing the radioisotope in injectable form, may occur at the off-treatment site. Thus, the outside provider may provide a radiopharmaceutical substance to the treatment site having a desired radioactivity level at the targeted time. Further "individual" dose preparation of the radiopharmaceutical agent may occur at the treatment site. Alternatively, the outside provider may provide a "finished" radiopharmaceutical agent ready for injection to a specified patient at a specified time so that treatment site personnel are only required to confirm that the correct radioactive dosage is present in the radiopharmaceutical agent, for example, in a stand-alone radiation dosimetry device as described previously. During the forgoing process, there is frequent close-proximity contact with radioactive materials by personnel and, as described previously, handling and transport shielding devices are needed for the protection of these personnel.

Transport pigs are commonly employed to transport the radiopharmaceutical agents, which are individual doses prepared for individual patients, to the treatment facility. At the treatment facility, data about each unit dose is entered into a facility computer either manually or through reading a bar code, floppy disk, or other similar data format, which may accompany or be on the transport pig or the radiopharmaceutical agent container. When it is time to deliver a specified unit dose to a specified patient, treatment facility personnel must remove, for example, a syringe containing the radiopharmaceutical agent from the transport pig and confirm that the dose in the syringe is within the range prescribed for that patient. Alternatively, the attending personnel must transfer the radiopharmaceutical agent to a shielded syringe as identified previously and confirm dosage. If the dose is too high, some is discarded into a shielded waste container. If the dose is too low, either a different syringe is used and/or additional agent is loaded into the syringe if available. While it possible for the attending treatment site personnel to be involved with dosage preparation, typical United States practice is to have the radiopharmaceutical agent delivered to the treatment site which will have the desired radioactivity level at the targeted time. Manual manipulation of the radiopharmaceutical agent at the treatment site is limited due to this procedure. Nonetheless, various manual checks are required to confirm that a correct radiopharmaceutical dose is ready for injection into a specific patient. These manual checks include visual inspections and radioactivity measurements as noted above.

As an example of the foregoing, in PET imaging, an injectable radiopharmaceutical agent such as, for instance, FDG (fluorodeoxyglucose) is fabricated in a cyclotron device at an outside nuclear medicine facility. Thereafter, the FDG is processed to be in a radiopharmaceutical form and is transferred in an individual dose container (i.e., vial, bottle, syringe, etc.) and the container loaded into a transport pig to prevent unnecessary radiation exposure to personnel, such as the radio-pharmacist, technician, and driver responsible for creation, handling, and transport of the FDG from the cyclotron site to the PET imaging site. Since the half-life of FDG is short, approximately 110 minutes, it is necessary to quickly transport the FDG to the PET imaging site. Depending upon the elapsed transport time and the initial radioactivity level of the FDG at the time of fabrication, the radioactivity level of the FDG may need to be re-measured at the PET imaging site. As an example, if the radioactivity level is too high, the radiopharmacist at the PET imaging site may be required to dilute the FDG with a diluent such as, for instance, saline solution, and remove part of the volume or extract fluid to reduce radioactivity prior to patient injection. During this entire process, the handling of FDG from creation to patient injection may be entirely manual. Within this process, shielding products, as described previously (i.e., transport pigs, syringe shields, L-blocks, etc.) are used to shield individuals from FDG. While shielding may reduce the radiation exposure of the radio-pharmacist, the radio-pharmacist may still be exposed to emissions from the radiopharmaceutical agent during the manual mixing, volume reduction, and/or dilution process needed to obtain the required dose. After injection and often after an additional delay to allow the radiopharmaceutical to reach and be absorbed by the desired regions of interest in the body, the patient is typically placed on a moveable bed that slides by remote control into a circular opening of an imaging scanner referred to as the gantry. Positioned around the circular opening and inside the gantry are several rings of radiation detectors. In one type of radiation detector, each detector emits a brief pulse of light every time it is struck with a gamma ray coming from the radionuclide within the patient's body. The pulse of light is amplified by a photomultiplier converted to an electronic signal and the information is sent to the computer that controls the apparatus and records imaging data.

For the sake of completeness, it should be noted that in the United States it also known to have radiopharmaceutical agents delivered in a multi-dose format to the treatment site. As a result, this multi-dose format must be divided into singular doses for individual patients at the treatment site. While it possible that this division may occur at the point of injection or administration, it more typical for a radio-pharmacist or nuclear medicine technologist to perform the dividing process in a "hot lab" at the treatment facility. The "hot lab" is equipped with a clean hood, shielding, and dose calibrators, all expensive durable equipment. Individual radiopharmaceutical doses are then transported to the administration location within the treatment facility where the doses are administered to specific patients.

In Europe, radiopharmaceutical creation and dose preparation practice differs from United States practice in that these actions typically all occur within a "hot lab" in the treatment facility again, typically, a hospital. As an example, the hospital itself typically has cyclotron or isotope generators (such as technetium generators manufactured by Mallinckrodt Inc., St. Louis, Mo.; Amersham Healthcare, 2636 South Clearbrook Drive, Arlington Heights, Ill. 60005; or GE Healthcare Limited, Amersham Place, Little Chalfont, Buckinghamshire, United Kingdom) in a shielded location in the hot lab. Two manufactures of shielded glove boxes are Comecer in Italy and Lemer Pax in France. Hospital personnel create or extract the radioactive isotope, perform additional chemistry steps necessary to formulate the radioactive drug (i.e., radiopharmaceutical) early in the day, and then prepare unit doses for individual patients, generally close to the time the patient is to be injected with the radiopharmaceutical. While an internal "hot lab" has advantages in minimizing hazardous material transport and improving internal information transfer, additional time and radiation burdens are placed on hospital staff as the measurement of radioactivity levels at the various steps still depends upon manual insertion of a container (i.e., a vial, bottle, or syringe) into a dose calibrator and then repeated adjustments of the radioactivity until the desired level is achieved. The unit dose radiation level is commonly recorded manually or by a printer.

Within the prior art, systems for delivering hazardous fluids are known as disclosed, for example, in U.S. Pat. No. 6,767,319 to Reilly et al. and United States Patent Application Publication No. 2004/0254525 to Uber, III et al., the disclosures of which are incorporated herein by reference. Another system adapted to inject a radioactive liquid into a patient is disclosed in Japanese Publication No. JP 2000-350783 (see also United States Patent Application Publication No. 2005/0085682 to Sasaki et al.), assigned to Sumitomo Heavy Industries. This published patent application discloses a system which dispenses a volume of radioactive fluid into a coiled "medicine container" situated in a radiation measuring unit. When the prescribed radiation dose is accumulated in the coiled container, another syringe pushes saline through the coiled container and into a patient. A similar device and method is disclosed in Japanese Publication No. JP 2002-306609, also assigned to Sumitomo Heavy Industries. Each of the immediately foregoing Japanese publications is incorporated herein by reference.

PCT Application Publication No. WO 2004/004787, assigned to Universite Libre De Bruxelles—Hospital Erasme and incorporated herein by reference, discloses a method by which continuous measurement of radioactivity by dosimetry is eliminated. The disclosed method requires an initial calibration step but, thereafter, radiation dose is calculated based on the predictable decay of radioactivity as a function of time. Japanese Publication No. JP 2004-290455, assigned to Nemoto Kyorindo KK, discloses a radiation-shielded injector system which withdraws FDG from prefilled syringes and allows other fluids such as saline to be administered. European Application Publication No. EP 1616587, assigned to University of Zurich and incorporated herein by reference, discloses a radioactive fluid dispensing device that pushes FDG into tubing within a radiation dose calibrator prior to a saline injection that administers the FDG to the patient. United States Patent Application Publication Nos. 2005/0203329 and 2005/0203330 to Muto et al. disclose a robotic, automated system for extracting radioactive fluids from a vial or bulk container into a number of unit dose syringes. This system may have application in a hospital pharmacy setting. United States Patent Application Publication No. 2005/0277833 (Williams), assigned to E-Z-EM, Inc. and incorporated herein by reference, discloses an injection system for handling, mixing, dispensing, and/or injecting mixtures of radiopharmaceutical agents. Radiation dose is monitored by discrete detectors at several locations in the apparatus.

SUMMARY OF THE INVENTION

In one embodiment, a hazardous fluid transport container is disclosed which comprises a housing enclosing a separate enclosure, a first fluid path element disposed in the separate enclosure and at least partially filled with a first fluid, and a second fluid path element disposed in the housing and connected to the first fluid path element. The second fluid path element is at least partially filled with a second fluid. The first fluid path element is in controlled fluid connection with the second fluid path element and at least one of the fluid path elements is adapted to be accessed from outside the housing.

The separate enclosure may be radiation shielded. At least one of the first and second fluid path elements may comprise coiled tubing adapted to be paid outward from the housing. A fluid detector may be associated with at least one of the first and second fluid path elements. The fluid detector may comprise at least one of a radiation detector and an air detector. The controlled fluid connection between the first fluid path element and the second fluid path element may be provided by a control valve.

In another embodiment, a hazardous fluid delivery system is disclosed, comprising a housing enclosing an at least partially radiation shielded enclosure, a first fluid path element disposed in the shielded enclosure and at least partially filled with a first fluid and a second fluid path element disposed in the housing and fluidly connected to the first fluid path element. The second fluid path element may be at least partially filled with a second fluid. A pump unit is desirably in controlled fluid connection with one or both of the first fluid path element and second fluid path element for dispensing fluid from the first fluid path element and the second fluid path element.

At least one of the first and second fluid path elements comprises coiled tubing adapted to be paid outward from the housing. A fluid detector may be associated with at least one of the first and second fluid path elements. The fluid detector may comprise at least one of a radiation detector and an air detector.

A method of priming a hazardous fluid delivery system with liquid is also described in detail herein. The method comprises providing the fluid delivery system comprising a fluid path element, delivering a first liquid to the fluid path element, delivering a separating fluid to the fluid path element, and delivering a second liquid to the fluid path element whereby the first liquid and second liquid are separated by the separating fluid. The first liquid may comprise a non-hazardous liquid and the second liquid may comprise a hazardous liquid. The hazardous liquid may be a radioactive liquid. The separating fluid may be a gas such as carbon dioxide or, alternatively, a liquid. A solid member, such as a small sphere, may be disposed in the separating liquid.

In another embodiment, a method for mitigating laminar flow injection bolus spreading is disclosed, comprising injecting a first fluid through a first lumen into a fluid flow path and injecting a second fluid through a second lumen into the fluid flow path, with the second lumen disposed concentrically about the first lumen. The first fluid moves substantially in a center of laminar flow in the fluid flow path and the second fluid moves in the fluid flow path substantially concentrically about the first fluid. The first fluid may be removed from the center of laminar flow in the fluid path downstream of the first lumen via an axially centered outlet lumen. The second fluid may be removed from the fluid path concentrically outward from the axially centered outlet lumen.

Further, a radiopharmaceutical fluid transport container is disclosed comprising a container body defining an internal compartment, with at least portions of the internal compartment being radiation shielded and a closure lid associated with the container body for enclosing the internal compartment. An inlet opening and an outlet opening are provided in the container body, the closure lid, or both the container body and closure lid to permit access to the internal compartment. A syringe and a fluid path set connected with an outlet of the syringe may be disposed in the container. The fluid path set comprises an inlet fluid path element and an outlet fluid path element. The syringe is disposed within the internal compartment such that at least a portion of the inlet fluid path element of the fluid path set extends through the inlet opening and at least a portion of the outlet fluid path element extends through the outlet opening. A radiation shielded window may be provided in the closure lid. An inlet check valve may be associated with the inlet fluid path element of the fluid path set and an outlet check valve may be associated with the outlet fluid path element of the fluid path set. At least one of the inlet fluid path element and the outlet fluid path element of the fluid path set may be adapted to be paid outward from the container body through the inlet opening and outlet opening. At least one of the inlet fluid path element and the outlet fluid path element of the fluid path set may be formed from coiled medical tubing.

A further embodiment is directed to a hazardous fluid filling and transport system, which comprises a hazardous fluid transport container and an associated filling system. The fluid transport container comprises a housing enclosing a separate enclosure, a first fluid path element disposed in the separate enclosure, and a second fluid path element disposed in the housing and fluidly connected to the first fluid path element. The filling system is in controlled fluid connection with at least the first fluid path element and comprises at least a first fluid source and a second fluid source. At least one fluid pump is associated with the first fluid source and the second fluid source for dispensing fluid from the first fluid source and the second fluid source into the first fluid path element and then into the second fluid path element.

The separate enclosure may be radiation shielded. At least one of the fluid path elements may comprise coiled tubing adapted to be paid outward from the housing. A fluid detector may be associated with at least one of the first and second fluid path elements. The fluid detector may comprise at least one of a radiation detector and an air detector. Controlled fluid connection between the filling system and the first fluid path element may comprise a control valve.

Further details and advantages will become clear upon reading the following detailed description in conjunction with the accompanying drawing figures wherein like parts are designated with like reference numerals or characters.

BRIEF DESCRIPTION OF THE DRAWINGS

FIG. 5A is a schematic representation of a fluid delivery system incorporating the fluid transport container of FIG. 2 for injecting radioactive fluid into a patient.

FIG. 5B is a schematic representation of a variation to the fluid delivery system of FIG. 5A.

FIG. 6A is a schematic representation of fluid conduction of a first fluid disposed concentrically in a second fluid as applied in several embodiments described herein.

FIG. 6B is an alternative embodiment of a concentric fluid conduction arrangement for multiple fluids to that shown in FIG. 6A.

FIGS. 9A-9I are schematic representations of a fluid delivery system comprising closed loop control of fluid flow from the system to achieve a desired injection bolus profile.

FIG. 14 is a perspective view showing an exemplary hazardous fluid syringe and associated fluid path set which may be carried by the hazardous fluid transport container of FIGS. 12-13.

DESCRIPTION OF THE PREFERRED EMBODIMENTS

Figure 1:
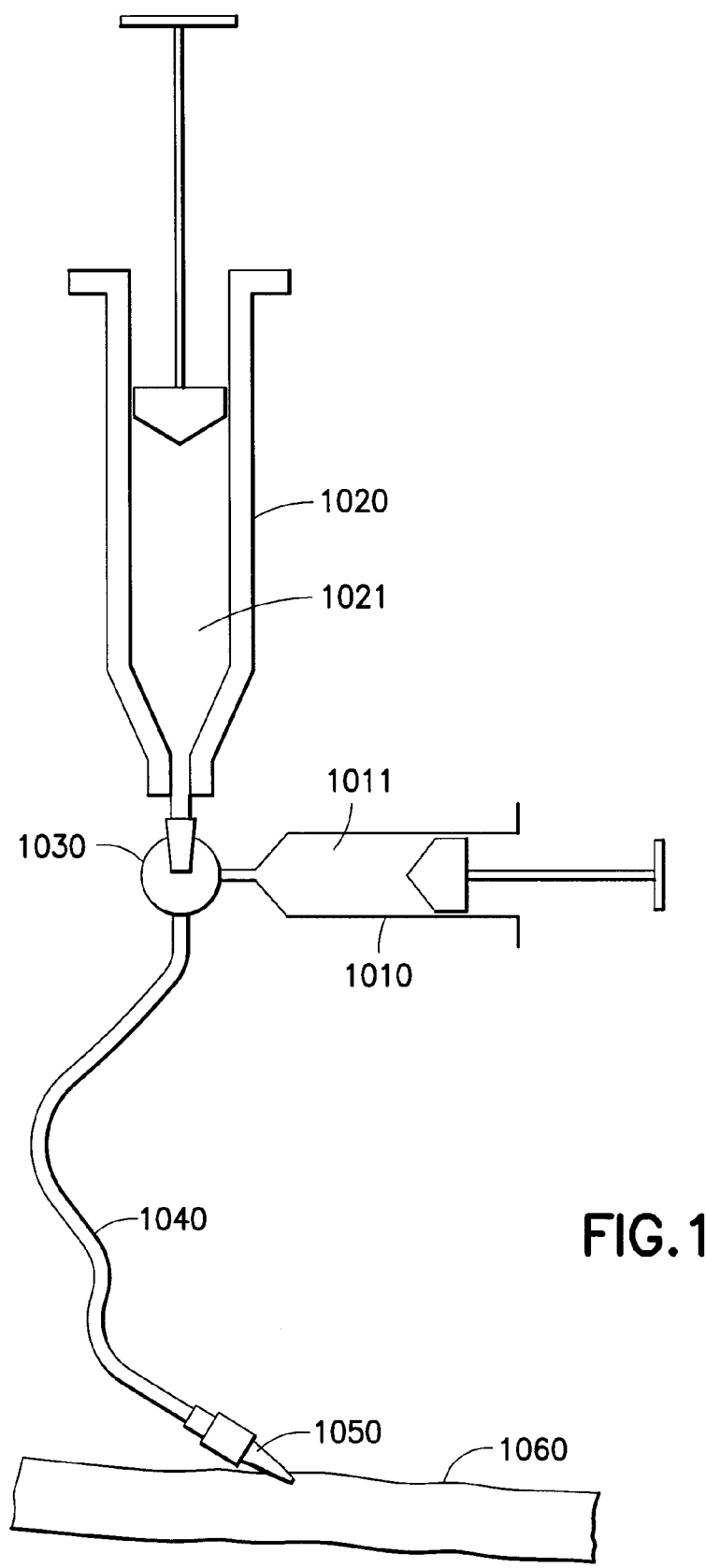
FIG. 1 is a schematic representation of a hand-operated system for injecting a radioactive fluid into a patient.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices, features, and components illustrated in the accompanying drawing figures and described herein are simply exemplary and should not be considered as limiting.

First pass cardiac imaging studies in the prior art involve quickly hand injecting a nuclear medicine tracer or radioisotope into a tubing connected to a patient's vein then quickly injecting a quantity of saline to flush the radioisotope from the tubing and veins of the patient. A series of images is taken as the isotope flows through the right heart, pulmonary arteries, lungs, pulmonary veins, left heart, and aorta. For this study to be most useful, it is desirable that the nuclear medicine tracer is in a "tight" or "compact" bolus and it is especially desirable that there not be two peaks in the time activity curve. The volume of the injected tracer being injected may be a fraction of a milliliter (ml) to a few milliliters. The use of a tight bolus produces better first pass images and/or data to be used in subsequent analysis. A tight bolus is desirably compact and avoids multiple peaks and significantly slow ramping-up or tailing-off. The disclosure herein is applicable to nuclear medicine with shielding and other requirements and all other medical fluid delivery applications that may not require radiation shielding or radiation measurement aspects. Impediments to maintaining a tight or compact bolus can occur in the fluid delivery phase and in the patient himself or herself. This disclosure uses the first pass cardiac imaging procedure as the backdrop for explaining the various concepts and methodologies of the present invention, and the various concepts and methodologies explained herein should not be considered as limited to this one specific application. Other non-limiting exemplary applications will be described herein as well and are known to those skilled in the medical arts. In addition, the manual process of injecting the nuclear tracer, turning a stopcock and then injecting a saline flush exposes the technician to radiation from the radiopharmaceutical.

It is known that certain factors can result in lengthening, smearing, or distorting an injection bolus and these factors can include laminar or turbulent fluid flow in fluid elements, tubing transitions, bends, and roughness which can introduce turbulence or mixing into the injection flow, and capacitance or "dead space" which is volume expansion of expansible elements such as medical tubing under pressure that subsequently contracts when pressure is reduced. A possible solution offered by this disclosure for capacitance effects includes pre-pressurizing expansible components of a fluid delivery system before an injection of drug fluid begins. With respect to the fluid flow path, transitions, bends, and internal roughness can be minimized to reduce turbulence that causes mixing at the beginning and end of the injection bolus.

In laminar flow conditions, it is well-known in the fluid arts that fluid in the center of a straight tube moves at twice the average velocity of the fluid profile and that the fluid velocity has a generally parabolic profile with the velocity being zero at the wall surface. Thus, in the present radiopharmaceutical application, when the fluid changes from one type or drug to another, the new drug (the second liquid) quickly moves down the center of the tubing but only slowly washes the first fluid out of the tube near the walls. With the small internal diameters (ID's) commonly used in medical fluid delivery applications, a medical fluid delivery system generally operates in the laminar regime. In one aspect of this disclosure, it is desirable to separate drugs boluses by solid or gaseous "plugs".

Other factors affecting injection bolus can be patient specific such as the volume of veins, vein branching resulting in insufficient flushing (e.g., fast inflow but then reduced outflow at the blood flow rate), vein stretching or distention, bad vein valves, and reverse flow. As is known, there are natural variations in vein volume and vein branching in the human body from individual to individual. As is further known, veins have a branching structure so that blood may still return to the heart independent of the tight or relaxed conditions of the muscles through which they pass. Table I below gives approximate blood volumes for typical vein segments for an adult human.

Vein branching makes this volume effect worse and, in some cases, makes it impossible to avoid a double-peaked bolus because the fluid path through one branch is longer than through the other. Injections into the veins on the back of the hand, for example, suffer from this effect to an even greater extent because of the additional volume of veins and the branching that occurs in the forearm.

In operation, veins behave similarly to a canvas fire hose in that they expand under pressure and collapse when not under pressure. If the veins are partially or fully collapsed, then much of the initial injection volume will go into expanding the veins and the forward motion will be delayed. Moreover, veins normally have valves that ensure one-way flow toward the heart so that when veins are compressed by movement, this compression helps pump blood back to the heart. If these vein valves are damaged, then the fluid of an injection can travel up stream in the veins. Accordingly, it is desirable pursuant to this disclosure to inject a significant volume of saline before the injection of the drug of interest, a radioactive fluid in the example presented herein.

If a mechanical, powered injector is used as a fluid administrator, inertia limits the acceleration of mechanical components and, thus, the rise time of the fluid injection bolus. Additionally, mechanical slack may be noticeable when changing from reverse motion to forward motion in a powered injection situation because the driving motor has to move some amount so that the force of the motor is transmitted through the mechanical gears and drive to create the pressure to drive the fluid. This inertial limitation can negatively affect injection bolus characteristics.

A feature disclosed herein relates to an improved fluid injection system and associated methods for time critical imaging studies. A desirable result of the fluid injection system is the ability to deliver a "tight" or "compact" bolus of injection fluid to produce or enhance first pass images and corresponding data. However, in certain instances, an extremely "sharp" injection bolus may not be necessary or even desirable, such as if nuclear medicine count rate (density) limitations may mean that there is a preferred time width to the bolus, or the effects of flow or mixing in larger veins and

TABLE 1

| | Length (cm) | Diameter (cm) | Area (cm^2) | Distended Volume (ml) | Velocity (cm/S) when at full area | Blood Flow (ml/S) | | |
|---|---|---|---|---|---|---|---|---|
| Cephalic | 38 | 0.6 | 0.28 | 10.74 | | | Whole | Whole |
| Basilic | 24 | 0.8 | 0.50 | 12.06 | | | Arm at | Arm |
| Brachial | | | | | | | Rest | 2.7 ml/S |
| Axillary | 13 | 1.6 | 2.01 | 26.14 | 1.34 | | 5.83 +/− .67 | |
| Subclavian | 6 | 1.9 | 2.84 | 17.01 | | | | |
| Right side from head | | | | | | | | 8.13 |
| R. Innominate | 2.5 | 1.9 | 2.84 | 7.09 | | | | |
| SVC | 7 | 2 | 3.14 | 21.99 | 6.90 | | | 21.67 |
| Heart | | | | | | | | 108.33 |

From the foregoing, it can be understood that there is quite a significant volume in the veins between the normal antecubital injection site and the superior vena cava (SVC). If the flush volume after the injection is not sufficient to push the injection bolus out into the superior vena cava then, once the injection stops, the bolus will slow down to the flow rate of the blood and move more slowly out into the superior vena cava. Accordingly, it is desirable, pursuant to this disclosure to provide a flush volume of more than 20 ml, preferably 40 to 60 ml, for normal adults, less for children.

right heart may distort the injection bolus sufficiently that even an infinitely tight bolus injected into the arm would be significantly dispersed or rounded before it reaches the regions of interest. A benefit of this system, which can deliver extremely sharp boluses, is that this capability enables a computer control system (as described herein) to controllably and repeatedly deliver less sharp boluses or even more sophisticated or effectively arbitrary bolus shapes or profiles as desired by the operator or required by the medical procedure. While the following discussion relates well to first pass nuclear medicine applications, the concepts herein are suited to other applications such as, but not limited to, nuclear medicine perfusion quantification, hyperpolarized C-13 delivered over a distance of 10 feet and in small volumes of a few ml, computed tomography (CT) test bolus injections (typically 20 ml of contrast), magnetic resonance angiography and functional imaging (typically 10-30 ml of drug), pharmacokinetic or pharmacodynamic studies, receptor dynamics studies, animal injections (often much less than 1 ml of drug), and high viscosity angiography (lubricated by a lower viscosity fluid surrounding the high viscosity contrast fluid, as described herein). In the high viscosity angiography context, a small "lump" or "slug" of contrast may result whose motion through the blood vessels can be tracked and used to help measure blood flow.

FIG. 1 shows a general, prior art hand powered fluid delivery system comprising a syringe 1010, commonly a 3 ml syringe, holding a nuclear medicine tracer 1011 and connected to a stopcock 1030. Also connected to stopcock 1030 is a syringe 1020, commonly a 20 ml syringe, filled with physiologic saline 1021. The saline 1021 is used to prime (e.g., remove air) from the fluid path including connection tubing 1040 terminating in a connection 1050 to an IV catheter. After the system is primed, it is connected to an IV catheter which has previously been inserted into a patient.

One challenge to delivering a tight bolus is the rapidity and uniformity of the hand actuation of the syringes 1010, 1020. Rapidly pushing the small volume of tracer 1011 is relatively easy. However, stopcock 1030 must be turned, which causes the flow in tubing 1040 to stop, and then a saline flush is rapidly delivered. The saline flush is commonly 15 to 20 ml in a 20 or 25 ml syringe 1020. Using such a large syringe 1020 makes it difficult to develop enough pressure to deliver the bolus quickly through a 22 gauge IV catheter, for example. If the volume of tubing 1040 is sufficient to contain all of tracer 1011 (a fluid or drug) in syringe 1010, then it does not start entering the patient until pushed by saline 1021 (or another fluid or drug). Thus, in this case, the delay in turning stopcock 1030 does not distort the bolus because it has not yet entered a patient's arm 1060. In other instances, the connection tubing 1040 is relatively short and the volume of tracer 1011 or other fluid may be one or more milliliters and so the time delay for turning stopcock 1030 can be relevant. In addition, in some instances there are additional drugs, for example, a cardiac stressor such as adenosine, being infused through some or all of the length of connection tubing 1040. In this case, the tracer 1011 that gets into the infusion stream would be carried along as the other drug is being infused at its infusion rate, causing the injection bolus to spread.

Figure 2:
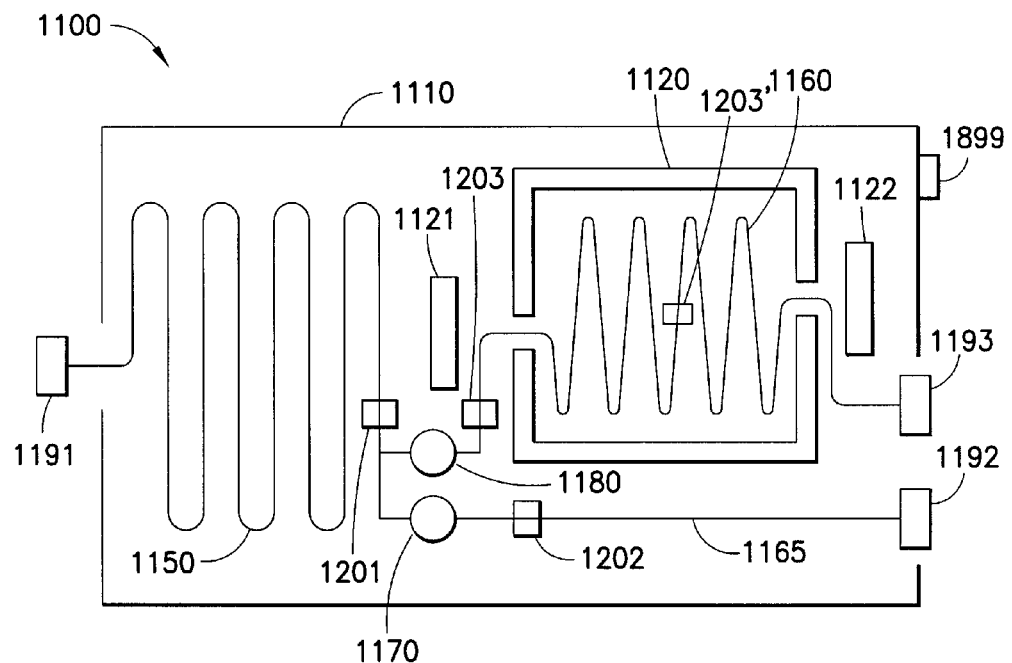
FIG. 2 is a schematic cross sectional view of an embodiment of a fluid transport container used as part of a fluid delivery system for injecting a radioactive fluid into a patient.
Figure 4:
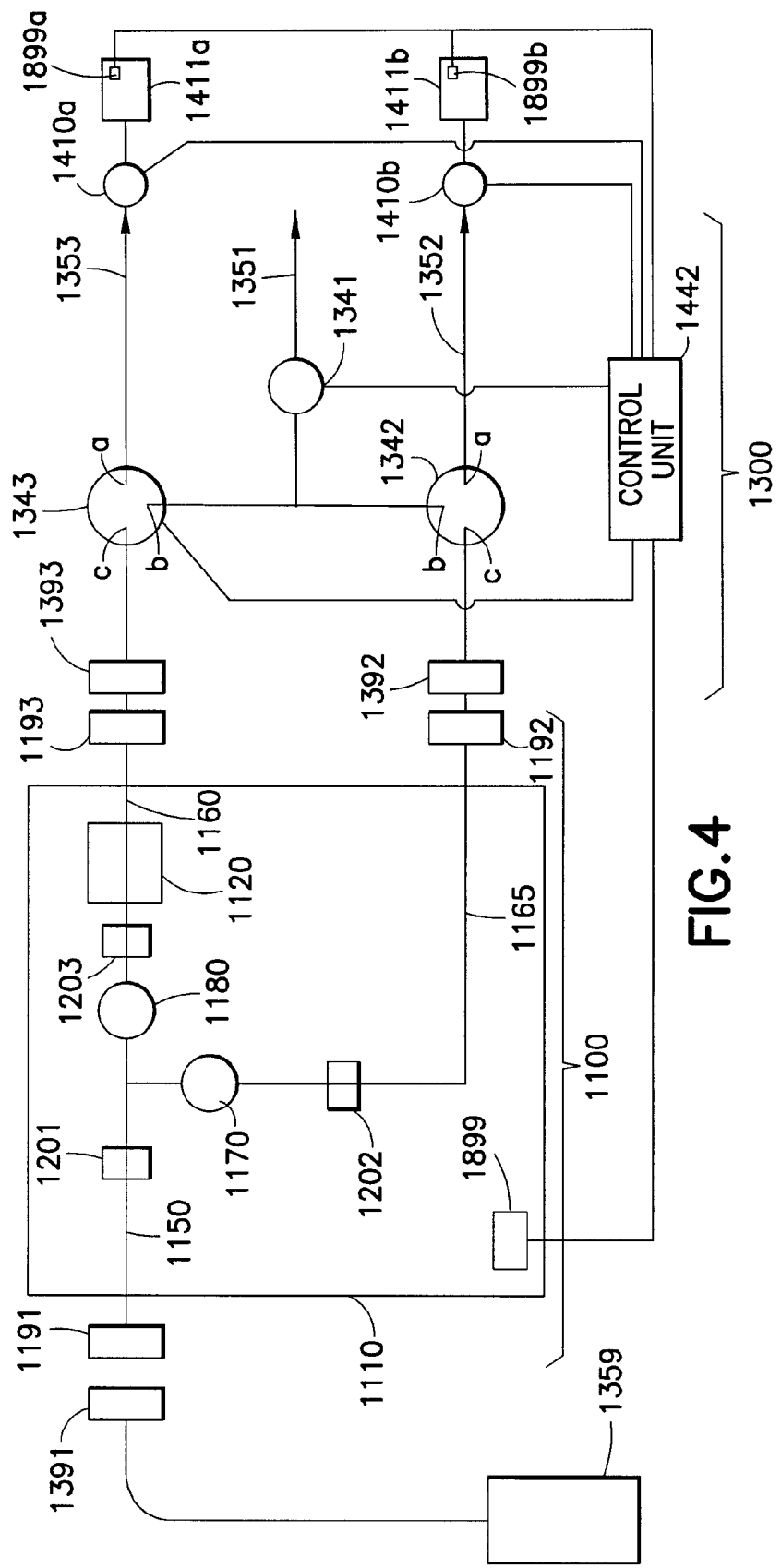
FIG. 4 is a schematic representation of a filling system for loading the fluid transport container of FIG. 2 with radioactive fluid, and which may also be used as a fluid dispensing system or platform.

FIG. 2 illustrates an embodiment of a drug transport container 1100 that is part of a fluid injection system described herein in connection with FIGS. 4-5 to overcome one or more of the impediments to achieving a tight injection bolus. The drug transport container 1100 and the system to be described in connection with FIGS. 4-5 is suited to providing a tight injection bolus to a patient of a drug of interest and the container 1100 and the system may be used in the procedures identified herein. The drug transport container 1100 and the associated system of FIGS. 4-5 implement the various "solutions" identified previously for the limiting factors associated with achieving a tight bolus in fluid injections in humans and animals. Drug transport container 1100 comprises a housing or enclosure 1110. Drug transport container 1100 comprises fluid path elements 1150, 1160, and 1165 in the form of medical connection tubing. Fluid path elements 1160 and 1165 join to form fluid path element 1150. In this disclosure, fluid path element 1160 may be referred to as a first fluid path element, fluid path element 1150 may be referred to as a second fluid path element, and fluid path element 1165 may be referred to as third fluid path element for exemplary purposes in explaining features of the shown embodiment. As schematically illustrated, one desirable form for fluid path elements 1150, 1160, and 1165 is as coiled tubing or optionally any fluid conduit or volume with a separate inlet and outlet such the fluid volume is carried downstream by fluid flow through the conduit. These fluid path elements may be physically mounted on or integrated with a tray or in a container so that the user can place them as a single unit into transport container 1100. While separately designated as distinct or separate fluid path elements 1150, 1160, and 1165 within this disclosure, this is intended to be exemplary only in explaining features of the invention and these elements may be combined or eliminated to yield equivalent fluid carrying flow paths as will be clear to those skilled in the fluid conveying field. One or more of all of the fluid path elements 1150, 1160, and 1165 may be paid outward from housing 1110 due to the coiled form of tubing comprising each element. In FIGS. 4-5 discussed herein, the coiled form of the fluid path elements 1150, 1160, and 1165 is omitted for clarity purposes.

Figure 3:
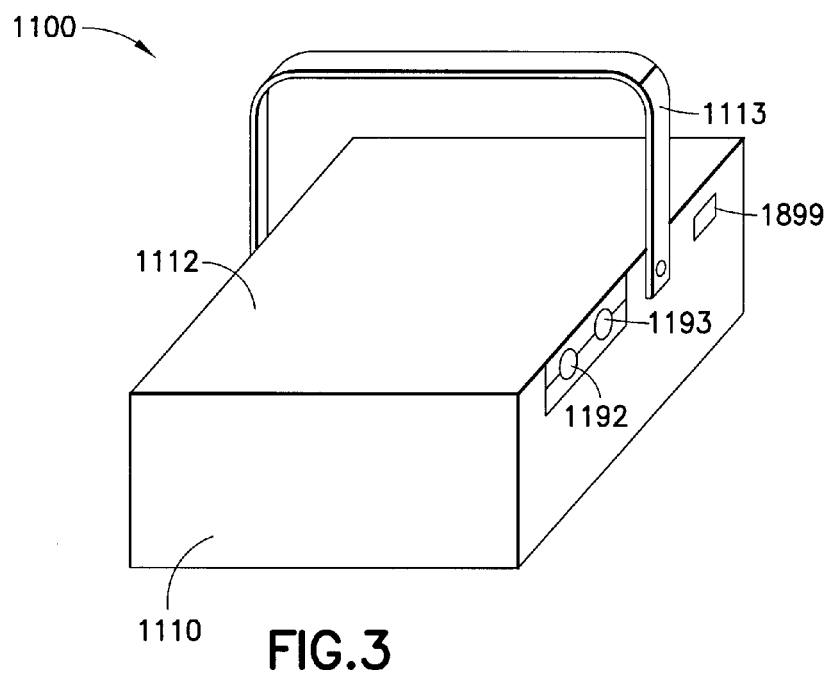
FIG. 3 is a schematic perspective external view of the fluid transport container shown in FIG. 2.

Fluid path element 1160 is intended to contain a radioactive drug and is surrounded by shield elements 1120, 1121, and 1122 of sufficient thickness and desirably made of tungsten, lead, or other shielding material to protect medical personnel from radioactivity emanating from the radioactive drag fluid in fluid path element 1160. Shielding 1120 is desirably in the form of an enclosure surrounding fluid path element 1160. Fluid path connectors 1192, 1193 allow connection of fluid path elements 1165, 1160, respectively, to upstream fluid sources and fluid connector 1191 permits connection of fluid path element 1150 to a patient-inserted catheter. Such upstream fluid sources may comprise a radioactive drug, also interchangeably called a radiopharmaceutical in this disclosure, and saline, as examples. Optional valve elements 1170 and 1180 are used in drug transport container 1100 for fluid flow control and may be, for example, one way check valves or slit silicone diaphragm valves which prevent diffusion and/or gravity driven movement of liquid in fluid path elements 1150, 1160, 1165. Optionally, valve elements 1170 and or 1180 may be normally closed electronically or mechanically activated control valves, for example, pinch valves or rotary valves. Sensor elements 1201, 1202, and 1203, for example, ultrasonic or infrared sensors, are provided to sense whether fluid path elements 1150, 1165, 1160, respectively, contain liquid or gas. Optionally, sensor elements 1201, 1202, and 1203, may incorporate or may be solely radiation sensors for use with radiopharmaceuticals to measure an aspect or condition of the drawing or delivery of a dose. Sensor 1203, if a radiation sensor, may be placed where it can measure radiation from some or all of fluid path element 1160, as indicated by sensor 1203'. Preferably attached to the container housing 1110 is one or more information tags or coded memory units, as indicated by data storage device or information tag 1899, which is associated with one or more of the elements of the transport container 1100. FIG. 3 is an external view of the outside of the drug transport container 1100 with a closed lid 1112 and a handle 1113 for carrying container 1100. Desirably, shielding (not shown) is provided in lid 1112 and in the base of container housing 1110. Thus, when lid 1112 is closed, very little radiation emanates from the drug transport container 1100.

Figure 18:
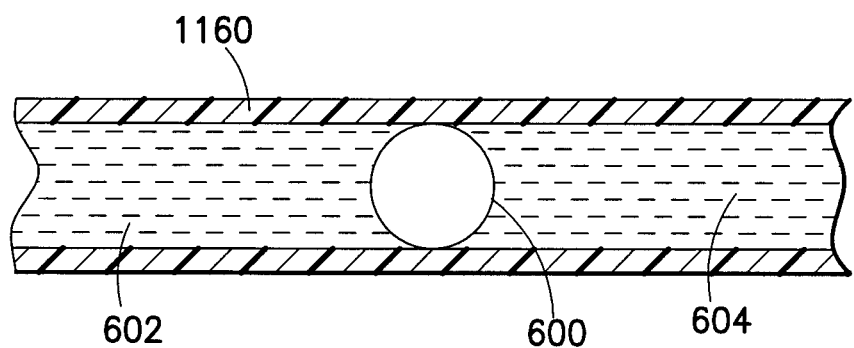
FIG. 18 is a cross-sectional view showing a separating arrangement for segregating two different fluids in a fluid path useful in several embodiments described herein.

FIG. 4 illustrates a filling and/or dose dispensing system 1300 adapted to interface with drug transport container 1100 for filling the drug container 1100 with radiopharmaceutical, saline, and/or other fluids. The filling system employs many elements that are similar to that disclosed in U.S. Pat. No. 5,806,519 (Evans, III, et al.), which is incorporated herein by reference. In this example, bubbles, preferably of $CO_2$ (carbon dioxide), are used to isolate the desired bolus of the radioactive drug and prevent its mixing with the priming fluid and flush fluid, which in this example are both saline. As shown in FIG. 18, a $CO_2$ bubble 600 is used to separate two fluids 602, 604 (saline and a radioactive fluid as described herein) located in, for example, fluid path element 1160 because it is relatively non-harmful when injected into a patient's veins in small quantities. $CO_2$ bubbles are preferred as fluid separators to help provide for maximum bolus sharpness, but are not exclusively required according to this disclosure. The fluid path elements 1150, 1160, 1165, preferably prearranged in a cassette form, preferably including a tray feature to catch any drips, are placed into housing 1110, with fluid path element 1160 residing in internal shielding enclosure 1120. Connector elements 1192 and 1193 are connected to filling system 1300 via mating connectors 1392 and 1393, respectively. To begin a filling operation, a volume of saline is pumped from saline source container 1411*b* with an associated data storage/memory element 1899*a* through conduit 1352 by fluid pump 1410*b* and through control valve 1342, wherein ports a-b are connected, and through control valve 1343, wherein ports b-c are connected, and then into fluid path element 1160. Control valve 1342 is then operated to connect ports a-c and valve 1341 is opened so that $CO_2$ from $CO_2$ source conduit 1351 may flow into fluid path element 1160. The source of the $CO_2$ can be a tank with a low pressure regulator. The volume of $CO_2$ put into the line is a function of the pressure and the time that control valve 1341 is open. A volume, typically less than 1 ml, is delivered. Then, control valve 1341 is closed and control valve 1343 is operated to connect ports a-c. A calculated volume to achieve the prescribed dose of radiopharmaceutical is delivered from a radiopharmaceutical source container 1411*a* with associated data storage/memory element 1899*b* though conduit 1353 by fluid pump 1410*a* into fluid path element 1160, pushing the saline and $CO_2$ before it. After the desired volume of radiopharmaceutical has been delivered into fluid path element 1160, control valve 1343 is operated to connect ports b-c and control valve 1341 is opened and less than 1 ml of $CO_2$ is delivered into fluid path element 1160. Control valve 1341 is then closed. Fluid path element 1160 is desirably sized so that it can contain a maximum volume of the two $CO_2$ boluses and the maximum volume expected for the radiopharmaceutical. Optionally, a radiation sensor 1203' can be used to measure or confirm the radiopharmaceutical dose that has been put in to fluid path element 1160. To complete the loading of fluid path element 1160, control valve 1342 is operated to connect ports a-b and saline is pumped into fluid path element 1160 until the leading edge of the first $CO_2$ "bubble" reaches sensor 1203, an air sensor in this example. The initial saline in fluid path element 1160 is sufficiently large so that its leading edge has moved into fluid path element 1150. Alternatively, without using a sensor, the volume needed to deliver liquid but not the bubble all the way to tubing 1150 could be calculated and delivered by a computer control system or control unit 1442. To complete the priming process, control valve 1342 is operated to connect ports a-c and saline is pumped from saline source 1352 to fill fluid path elements 1165 and 1150. The overflow can flow out fluid connector 1191 or, optionally, be collected in disposable waste container 1359 through connector 1391. Alternatively, a prime tube similar to that associated with a MEDRAD Stellant™ injector may be used, (see U.S. Pat. No. 7,018,363 (Cowan, et al.) and United States Patent Application Publication Nos. 2004/0064041 (Lazzaro) and 2005/0113754 (Cowan), each of which is incorporated herein by reference). The prime tube can remain attached to connector 1191 as a cap until the operator is ready to connect connector 1191 to a patient.

Once filled, drug transport container 1100 can now be transported to an injection site, for example, a cardiac stress room with a first pass camera such as those manufactured by CDL of Wexford, Pa.; a quiet injection room as is commonly done with FDG; or an imaging room so that the imaging may begin with or soon after the injection. Alternatively, drug transport container 1100 may be a non-transportable or an optionally transportable part of a powered injector (such as those shown in FIGS. 2A-2B or FIG. 18 of International Application No. PCT/US07/89101 (WO 2008/083313) incorporated by reference previously).

Delivery of the radiopharmaceutical from drug transport container 1100 can be understood readily when reviewing FIGS. 5A-5B. It is noted that the sensor elements 1201, 1202, and 1203 are omitted in the views of FIGS. 4-5 for clarity in explaining the subject matter of these figures. A fluid delivery system or platform is formed when drug transport container 1100 is mated with a pumping unit or fluid pump system 1400 which contains a pump unit 1410, a system controlled valve 1420, a saline source 1401 and other aspects, not shown, such as a computer, power source, and user interface which are used for controlled, repeatable, and synchronized operation. Fluid connectors 1192 and 1193 are connected to pump outlet connectors 1432, 1433, respectively. Terminal or end connector 1191 and fluid path element 1150 are desirably "pulled" or paid outward from housing 1110 of drug transport container 1100, and connector 1191 is used to connect to an IV catheter C that is inserted previously into the veins of a patient P. Each of the fluid path elements 1150, 1160, 1165 may be coiled tubing that may be pulled or paid out of housing 1110. Stops may be incorporated along the fluid path elements 1150, 1160, 1165 so that the respective fluid path element is not pulled or paid from housing 1110 too far. This is advantageous to ensure that any segment fluid path element 1160 that contains radiopharmaceutical is not pulled from the shielded volume of transport container 1100. Fluid path element 1150 is desirably of sufficient length so that it can reach and be connected to the patient's IV catheter C. In one embodiment, a small volume of fluid is administered (a few milliliters over a few seconds) as a test injection to confirm patency of the patient's IV insertion. If the insertion is patent, then the injection may be given. The drug transport container 1100 could alternatively be used with fluid pump system 1400*a* of FIG. 5B where two independent syringe pumps 1410*a*(1), 1410*a*(2) drive fluid through the two fluid path elements 1160 and 1165. These two syringe pumps could, for example, be a MEDRAD Stellant™ dual injector or a MEDRAD Spectris Solaris EP™ injector. Throughout this disclosure, the injector or pumps are computer controlled and have a user interface that allow programming and control of the fluid flow through means known to those skilled in the art. For the purposes of this disclosure, "pumps", "pump units", and "pressurizing device(s)" may be any type of pumping device known in the medical arts as, for example, a syringe pump as shown in FIG. 5B, peristaltic pumps, rotary vane pumps, positive displacement pumps, or other pumps commonly used in the medical or fluid movement arts. The control unit 1442 interacts with the data storage/memory device(s) 1899 of the drug transport container 1100 to gather information that is useful in the drug delivery and to deliver, save, or record information that will be useful subsequent to the delivery.

As mentioned previously, one of the effects that can distort an injection bolus is the swelling or distension of veins. Also, if there are any incompetent vein valves, when a power injection occurs, fluid can flow backward in the veins, further delaying the delivery of the drug. To reduce the effect of these sources of variability and bolus broadening, it is desirable to inject a volume of saline at the full flow rate of the drug delivery to distend and fill the veins immediately before the delivery of the drug. This is desirably accomplished by connecting pump unit 1410 through control valve 1420 and ports a-c of control valve 1420 and delivering 10 to 40 ml of saline at a programmed flow rate, for example, 4 ml/s. Then, control valve 1420 rapidly operates to connect ports a-b and the saline is again pumped into the patient P preferably at the same flow rate, this time flushing the radiopharmaceutical from fluid path element 1160, through fluid path element 1150, and into the patient P. A sufficient volume of additional saline flush, for example, 20 to 60 ml, may also be delivered so that the radiopharmaceutical is flushed out of the peripheral veins and into the central circulation. After the injections are complete, the "cassette" or "tray" mentioned previously encompassing fluid path elements 1150, 1060, 1065 and any associated mechanical assemblage allows these elements to be removed from container housing 1110 as a unit for disposal. Optionally, fluid path elements 1160 and 1165 may be used for multiple patients and terminal or end fluid path element 1150 or some sufficient segment thereof may be disposed of for each patient. For example, the patient end of fluid path element 1150 can include a segregating check valve to prevent backflow and an additional connector upstream of such a check valve may be incorporated so that the distal shorter length of tubing downstream of the additional connector and including the check valve may be changed out for each patient.

Figure 5C:
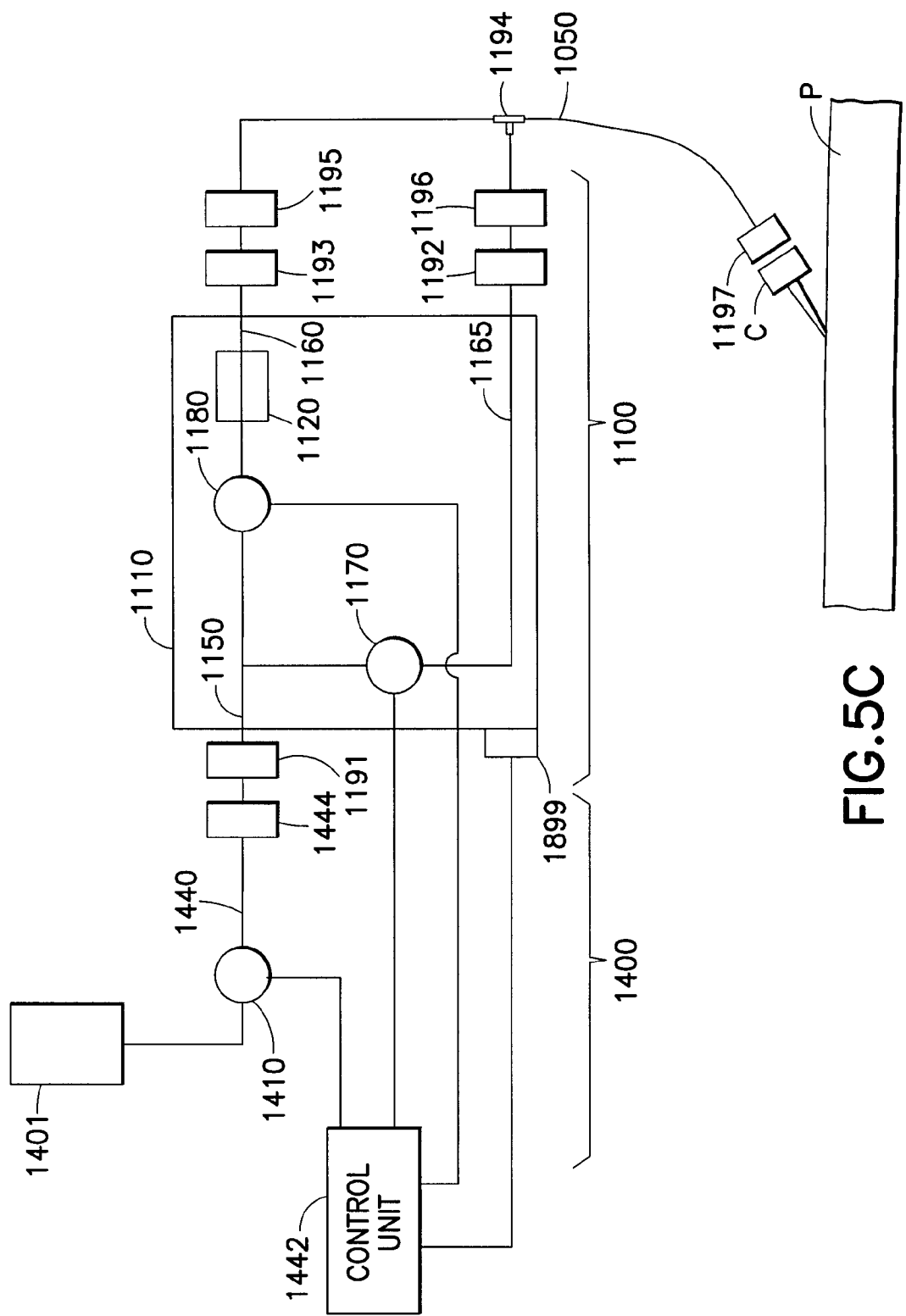
FIG. 5C is a schematic representation of another embodiment of the fluid delivery system of FIG. 5A.

Referring to FIG. 5C showing another embodiment the fluid delivery system shown in FIGS. 5A-5B, if fluid path element 1160 of fluid handling container 1100 described previously is filled with a drug from the end nearer connector 1193, much of the effects of bolus flow spreading may be eliminated by having the injection bolus be ejected out the same end from which it was filled, optionally through a short tube into patient P. This arrangement eliminates the need for the injection bolus to travel the full length of the tubing. The system of FIG. 5C can be used to deliver fluid from the fluid handling container 1100 in the manner described previously. The drug transport container 1100 can be placed near the patient P and the connectors 1193 and 1192 can be connected to the patient through a Y-connector 1194 comprising inlet fluid connector elements 1195 and 1196 (mated to fluid connectors 1193, 1192, respectively) and an outlet fluid connector 1197 connected to patient IV catheter C or a simple short tube to the patient's IV catheter C. A longer fluid path element (e.g., tube) 1440 can be connected to pump unit 1410 and saline source 1401. In this embodiment, valves 1170 and 1180 are preferably electronically controlled valves controlled by a control unit 1442 controlling fluid pump unit 1410 in fluid pump system 1400. Alternatively, the valves 1170 and 1180 could be replaced with a computer-controlled stopcock, for example, and which may be similar to control valve 1420 described previously. For example, injecting saline through fluid path element 1165 allows the veins to be filled before injection. Then, valves 1170 and 1180 may be switched so that the fluid flows through fluid path element 1160, delivering the drug and then a sufficient volume of the flushing fluid and providing all the benefits of the embodiments described hereinabove. One of the benefits of this embodiment in which the drug is loaded through a fluid connector and then delivered back out through that same fluid connector is that the fluid separator can easily be a solid ball in fluid path element 1160 and no separating gas (for example, $CO_2$) is needed.

Such a separating ball is small enough so that it can move down fluid path element 160. The separating ball is constrained to stay in fluid path element 1160 by a screen element or similar capturing mechanism in fluid connector 1193 and at the junction of fluid path element 1160 with fluid path element 1440 which will allow fluid to flow around the ball when it is stopped by the screen. In general, in the embodiments of this invention, the drug and flushing fluids are preferably separated in the fluid path elements or conduits to provide a tighter bolus of the injected drug. The term separating fluid includes a gas of a sufficient volume, a liquid with physical properties such as immiscibility or high viscosity of a sufficient volume to act as plug flow, or a solid element or elements such as the ball described herein, sized so that it flows as a plug in the fluid path elements as desired. Accordingly, in FIG. 18, $CO_2$ bubble 600 may be replaced by a slug of liquid or be a solid member such as a ball that is carried along by fluid flow in the fluid path element.

In variations of the foregoing fluid delivery systems of FIGS. 5A-5C, fluid path element 1165 may be eliminated if there is no desire to start an injection sequence with saline or to deliver saline without moving the radioactive drug. Also, for example, control valve 1420 of FIG. 5A or the Y-connector 1194 of FIG. 5C may be incorporated into drug transport container 1100. Moreover, the whole pumping mechanism including saline source 1401 and fluid pump unit 1410 and control unit 1440 may be physically incorporated into one unit in alternative variations.

In variations of the foregoing fluid delivery systems of FIGS. 5A-5C, fluid path element 1165 may be eliminated if there is no desire to start an injection sequence with saline or to deliver saline without moving the radioactive drug. Also, for example, control valve 1420 of FIG. 5A or the Y-connector 1194 of FIG. 5C may be physically incorporated into drug transport container 1100. Moreover, the whole pumping mechanism including saline source 1401 and fluid pump unit 1410 and control unit 1442 may be physically incorporated into one unit in alternative variations.

A benefit of the system of FIG. 5C is the potential close proximity of the drug to the patient. In the filling or dispensing system of FIG. 4, the drugs are filled into the ends of fluid path elements 1160 and 1165 farthest from fluid path element 1150. By dispensing fluid through the connector elements (connectors 1192, 1191, respectively) through which they were filled, the dispersion of the injection bolus can be reduced. Such a delivery is facilitated by the fluid delivery system of FIG. 5C. In International Application No. PCT/US07/89101 (WO 2008/083313), embodiments are disclosed wherein the drug volume and optionally some other aspects of an injector system are mounted near or on a patient's arm. The present disclosure further envisions that the drug volume and some accompanying aspects of the injector system may be mounted on a vest worn by the patient, which optionally includes some aspects of ECG needs. Alternatively, aspects of the injector system supporting the drug volume could be held by a holster like arrangement worn by the patient, for example, a shoulder holster arrangement or a waist mounted holster arrangement.

If a patient is to receive sequential injections of multiple drugs, additional fluid path elements may be added that come together at a common junction to patient fluid path element 1150 or at a sequence of junctions such that their contents can be delivered to the patient through fluid path element 1150. For example, some imaging procedures use two radioactive isotopes, technetium and thallium. As will be clear to those skilled in the medical art, particularly nuclear medicine field, the fluid transport container, fill and delivery systems, and respective devices of FIGS. 2-5 can include additional elements and devices, optionally similar or identical to those described, to achieve the ability to controllably prepare and deliver multiple drugs. Additionally, many nuclear medicine procedures and many other medical procedures do not require a very tight bolus for a successful outcome. In these instances, $CO_2$ "bubble separation", as described previously, is not needed and certain specific features of the various embodiments described in this disclosure can be relaxed or eliminated, while still retaining some of the other benefits described in this disclosure.

The system, devices, and techniques provided throughout this disclosure may be used in various imaging or other medical procedures where rapidly acquired or first pass information or data is of use. Cardiac first pass nuclear medicine has been described in some detail. There are other nuclear medicine first pass studies involving, for example, the lungs and kidneys. Some PET imaging studies can use first pass information, sometimes in addition to longer duration information. CT angiography (CTA) is preferably done as a first pass study. Various isotopes and/or molecules can be used singly or in combination.

Hyperpolarized C-13 and similar atoms can be incorporated into molecules or used directly as imaging agents in magnetic resonance imaging (MRI). Generally, the atom is hyperpolarized some distance from the imaging magnet because the process requires a high magnetic field, as does the imager, and the two fields must not interfere with each other, as disclosed by U.S. Pat. No. 6,453,188 to Ardenkjaer-Larsen, et al., incorporated herein by reference, (see FIG. 2 for schematic illustration). Either a syringe with a few milliliters of the drug can be quickly moved from the polarizer to the patient or a long tube may be used. If long tubing is used, then many or all of the injection bolus broadening (e.g., distortion) phenomena discussed herein can occur, and the countermeasures discussed herein can be beneficially applied. For example, rather than storing the drug in a dose container with a coiled tube, the drug is effectively transported through fluid path element 1150 discussed previously which spans the distance from the drug's polarization point and delivery to the patient's IV catheter C. For hyperpolarized C-13, there can also be a problem with the material becoming depolarized by contact with the wall of the carrying tubing. A concentric flow arrangement, discussed in detail herein, can reduce or prevent this effect.

In CT imaging, a test bolus can be given to measure or assess the response of the patient's body so that a custom designed imaging bolus or a larger volume can be given to provide optimum imaging. For example, in a CT Angiography (CTA) study, the injection bolus is designed to have sufficient contrast in the coronary arteries for a lumen to be accurately visualized and the lumen observed but not so much contrast that calcifications are confused for lumen. In the right heart, the contrast must be sufficient to differentiate blood from muscle but not so much as to cause streak or beam hardening artifacts. To determine the optimum imaging bolus profile, a test injection bolus of modest volume of about 20 ml or less of contrast may be used. A sequence of images of this test bolus is then used to design the optimum imaging bolus. As discussed previously, there are a number of factors than can delay or distort the test bolus. If the imaging injection bolus is designed using the results of a distorted test bolus, the imaging injection bolus is likely to provide less than optimum results. The system, devices, and methods of this disclosure may be used to minimize the distortion of the test bolus and also improve the sharpness of the imaging injection bolus.

In MR angiography and MRI functional imaging, injections on the order of 10, 20, or 30 ml can be delivered to a patient in a single bolus. For MR angiography, the goal is opacification of blood in the blood vessels. In functional imaging, the goal is to develop a concentration versus time curve in various voxels in the patient. These curves can then be used to calculate perfusion of the tissue. In the brain, for example, increased perfusion can indicate increased activity caused by a specific task. A distorted bolus can distort the concentration versus time curves and make the analysis difficult, inaccurate, or impossible. As discussed previously, there are a number of factors that can delay or distort the test bolus. The system, devices, and methods of this disclosure may be used to minimize the distortion of the test bolus and also improve the sharpness of the imaging bolus.

As described in International Application No. PCT/US07/89101 (WO 2008/083313), a mouse's blood volume is approximately 2 ml, so injecting more than 0.2 ml is likely to be fatal. Injections are commonly 25 to 50 μl (0.02 ml to 0.05 ml). Tubing length and inside diameter (ID) are typically reduced as much as possible but it is difficult to have less than 12 to 18 inches of tubing length. The most common small ID tubing is PE10 which has an ID of 0.010 inch. This tubing has 1.57 μl/inch of length, so an 18 inch piece of tubing has 28 μl of volume, approximately the injection volume. The use of gas bubbles in tubing as provided by this disclosure would be a big benefit in this situation in combination with a dual path to "suck" much of the priming volume out of the line as the injection bolus is being delivered (see FIG. 7 of International Application No. PCT/US07/89101 (WO 2008/083313)).

The embodiments of this invention are generally directed at the delivery of fluids to animal and humans. In this situation the fluid and the elements contacting the fluids need to be sterile, clean, and free of any harmful contaminants or pyrogens. In medical practice in the United States, this is often accomplished by using single use, pre-packaged, sterile disposable fluid path elements and single use, single patient sources of fluids. This may greatly increase the cost and waste, however, as well as the work in preparing the delivery system and thence the opportunity for error in that preparation as well. In a set of issued United States patents, MEDRAD, Inc. has disclosed multi-patient delivery systems which allow the use of bulk containers of fluid and selected elements of the fluid path for multiple patients. These systems also include a single patient disposable that is thrown away after each patient because it could be contaminated by the patient, and the systems include a sterility assurance device or mechanism. Examples can be seen in U.S. Pat. No. 5,569,181 incorporated herein by reference and other patents incorporated herein by reference. For example, the fluid path elements and fluid containers of dispensing or filling system 1300 in FIG. 4 may be multi-patient or multi-use disposables that are disposed of periodically, for example, at the end of the day, but are used for subsequent patients until the fluid source is depleted or changed. Similarly, the fluid path elements of the delivery or pumping system 1400 of FIGS. 5, 10, and 13 may have fluid path elements and fluid containers that are preferentially useable for multiple patients. Likewise, within the transport container 1110, selected fluid path elements or segments of elements, for example 1160, 1165, and 1150 may be used for multiple patients if the distal most segment of fluid path element 1150 is changed, discarded, or disposed of after each patient and sterility assurance devices or mechanism are include to prevent contamination of any multi-use or reusable portion. For example, in FIG. 10A, a segment of fluid path element 1150, fluid path element 1152, could be disposed of after each patient and contain the sterility assurance device, such as a one way check valve or dual one way check valve.

Figure 9A:
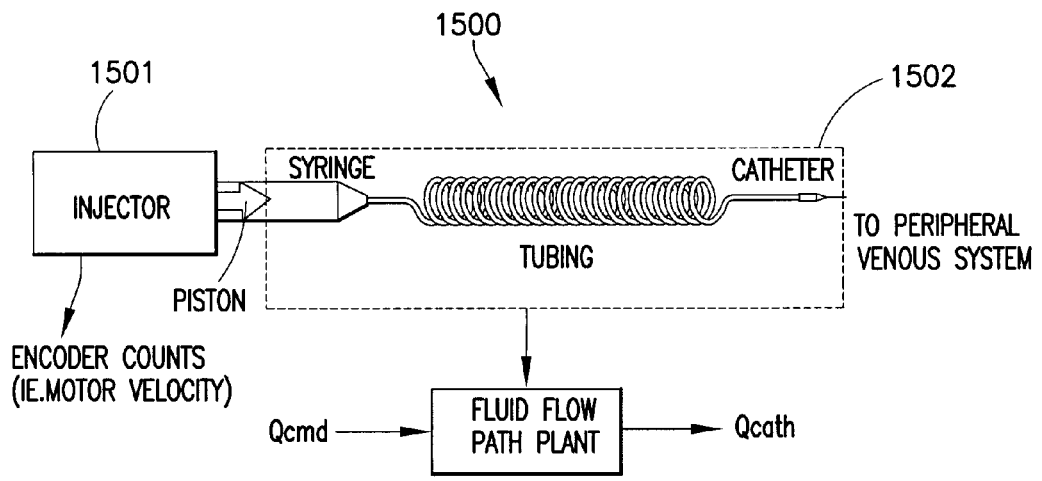
Figure 9B:
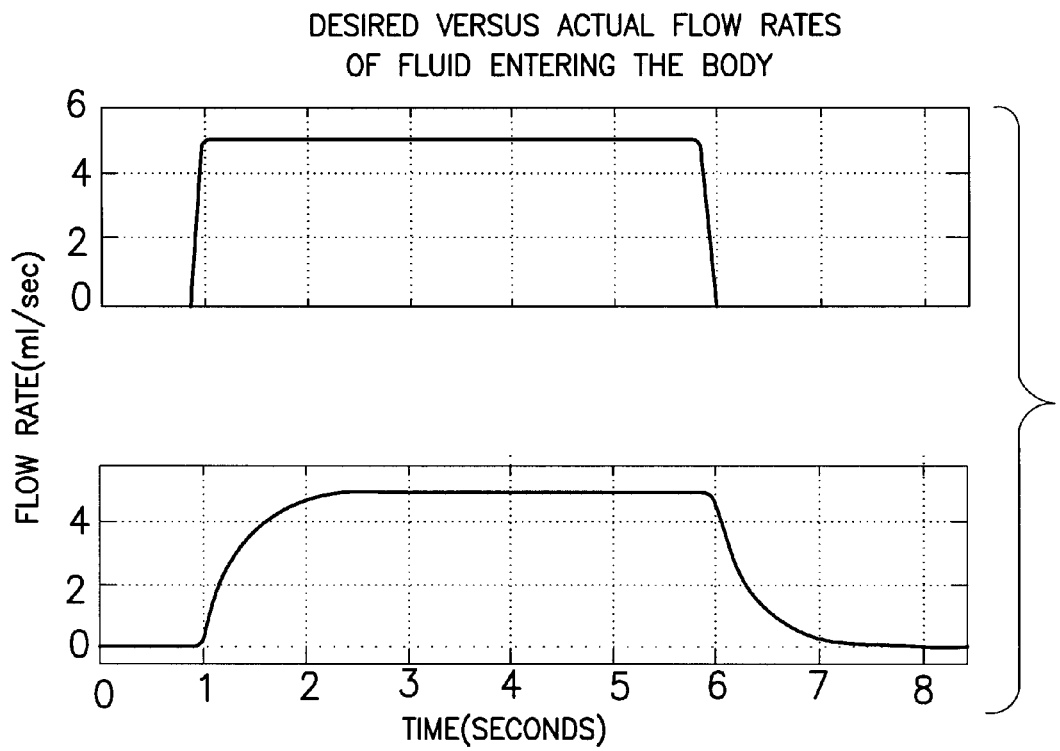

Referring next to FIGS. 9A-9I, in powered injector operations, normally injector servo-systems use a closed loop to control the plunger motion in an injection syringe, as is known in the relevant art. An exemplary powered injector system 1500 is shown in FIG. 9A comprising a powered injector and a fluid flow path 1502. It is desired to obtain a tight, square geometry in the injection bolus as shown in the top graph in FIG. 9B. However, various factors can affect or distort injection bolus characteristics. As a reminder, such factors may include physiochemical properties of the injection fluid (e.g., X-ray contrast media in the graphical examples in FIG. 9B), system factors such as compliance, and patient factors. Distortion phenomena can lead to the injection bolus result shown in the bottom graph in FIG. 9B, as an example. A distorted injection bolus is undesirable because time to steady state flow rate is increased, steady state flow rate may not be achieved within a short imager scan window, and functional perfusion imaging algorithms assume or work best with a tight injection bolus characteristic.

With the foregoing in mind, an algorithmic approach may be used to improve control of the flow profile of the injection bolus of fluid into the patient. This algorithm may be used, for example, to control the operation of pump units 1410, 1410a, and control valve 1420 in the respective fluid delivery systems of FIG. 5A-5C, discussed previously, as examples. This algorithmic approach is desirably based on a data-driven, per-use model of the fluid flow path 1502 designated in FIG. 9A by dashed lines. To simplify the acquisition and improve the accuracy of the data about any or all of the fluid path elements in the system, data storage devices 1899 such as bar codes, memory devices, or RFID's can be associated with various fluid path elements as described in U.S. Pat. No. 5,739,508 (Uber, III), incorporated herein by reference, preferably including the IV catheter C discussed previously. Such data storage devices may also be associated with the drug transport container 1100 described previously, for example, by being associated with the housing 1110 of the container 1100, as well as or alternatively associated with fluid path elements 1150, 1160, or 1165 or a "cassette" including these elements. Additional examples of such data storage devices are found in International Application No. PCT/US07/89101 (WO 2008/083313) and relate to hazardous fluid transport containers generally. These devices may be used to provide the control computer which implements the algorithm with the necessary information about the various fluid path components to tailor the algorithm or model to the fluid path elements that are present. These devices may also be used to transmit or confirm information about the contents and state of the fluid path elements. Additionally, these devices may be used to capture and transmit information about the patient and the procedure, both before or after the procedure, for the individual patient or hospital records, or for broader use, for example, as described in U.S. Pat. No. 7,457,804 (Uber, III, et al.), which is incorporated herein by reference.

Figure 9C:
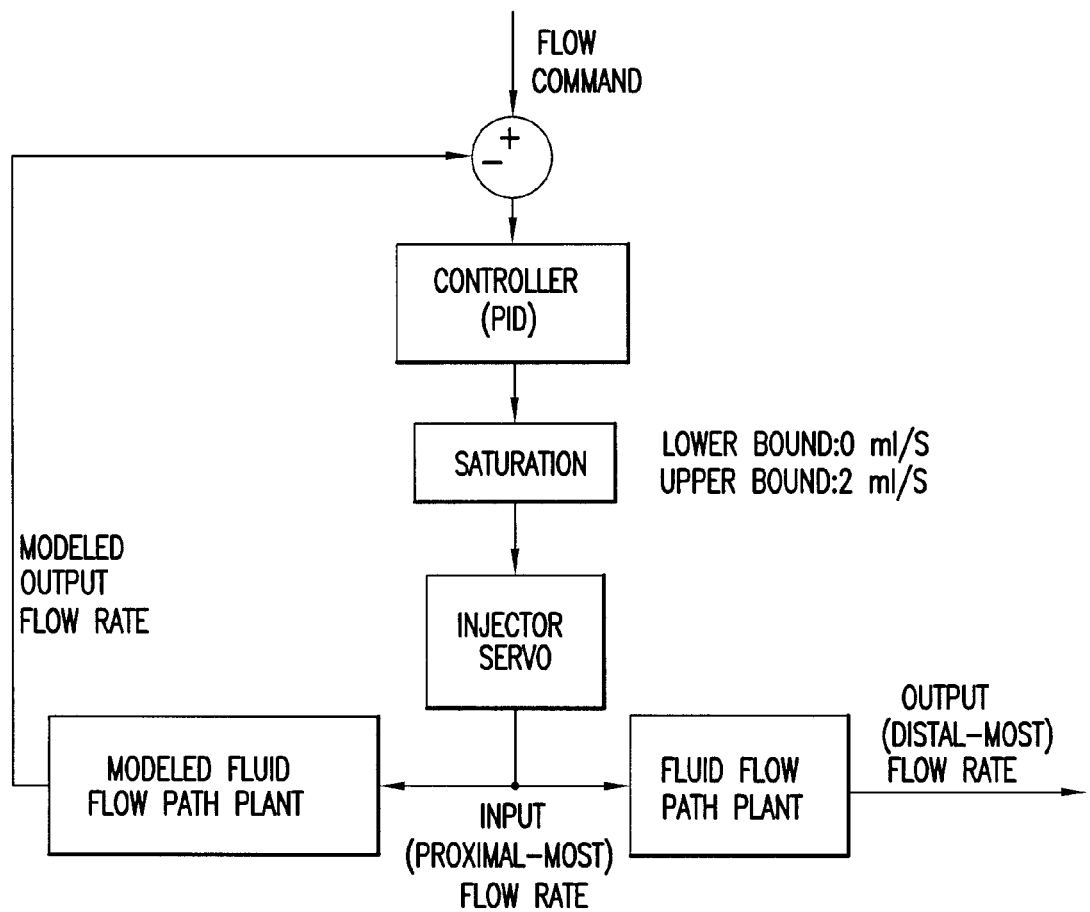
Figure 9F:
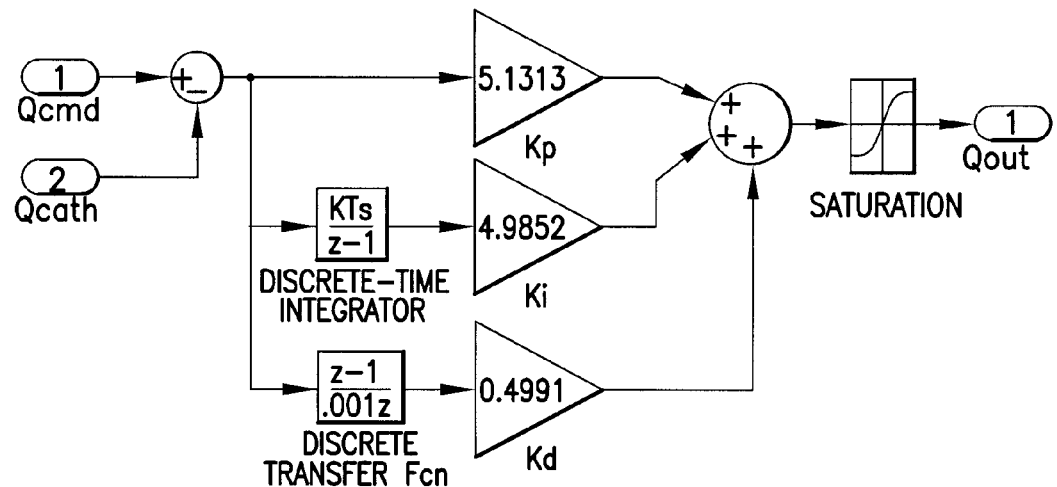

FIG. 9A is one generic example of such a fluid flow path and FIGS. 5A-5C is another such example. Referring to FIG. 9C, the design may encompass a digital control system (for example, a PID controller) with the flow rate bounded, for example, within 0 ml/s to 2 ml/s. FIG. 9C represents a closed loop control system for controlling operation of the fluid delivery system 1500 in FIG. 9A, wherein controller error signal is equal to the desired flow rate minus the estimated output flow rate and the fluid flow path model input is the injector motor velocity measurement.

Figure 9D:
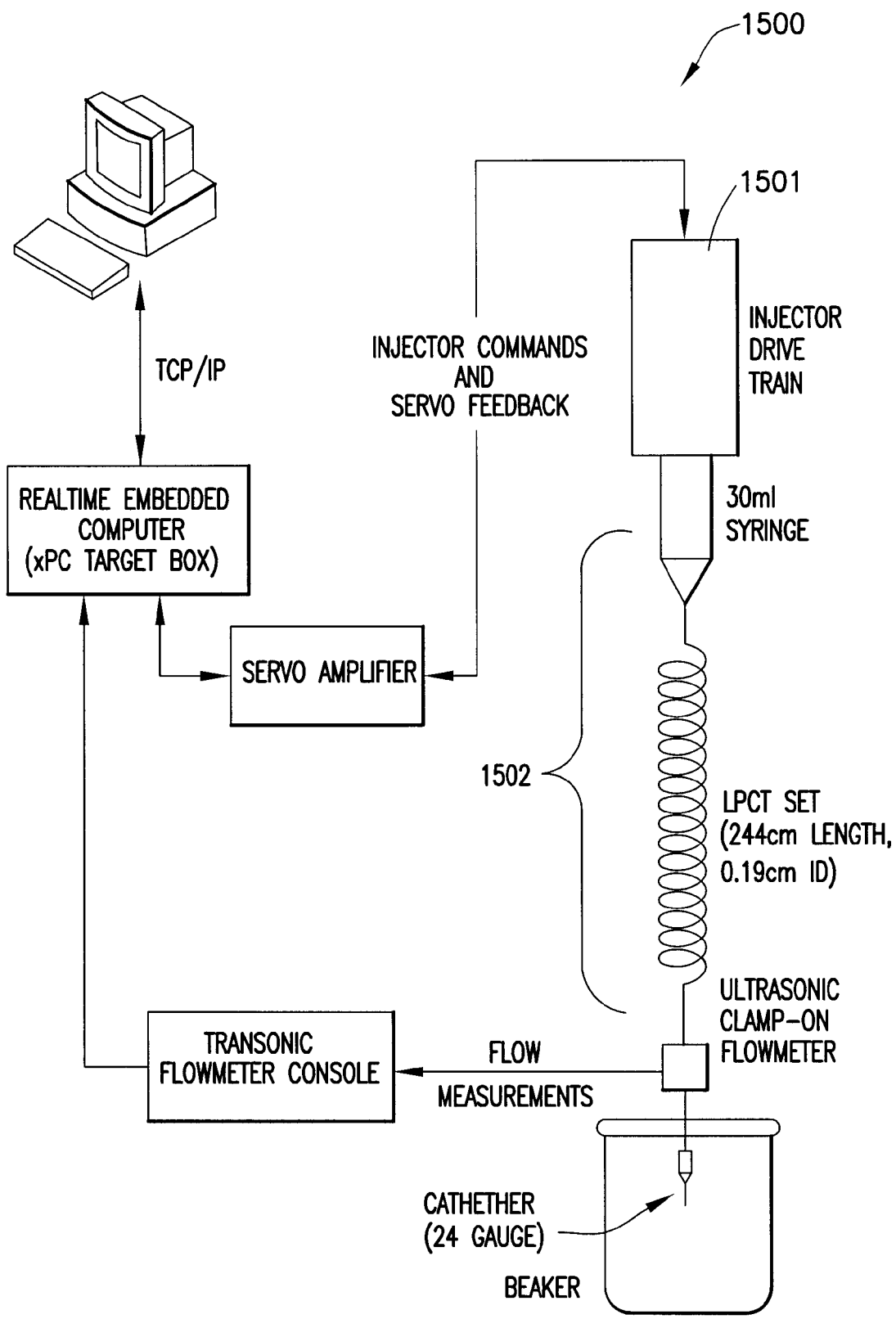
Figure 9E:
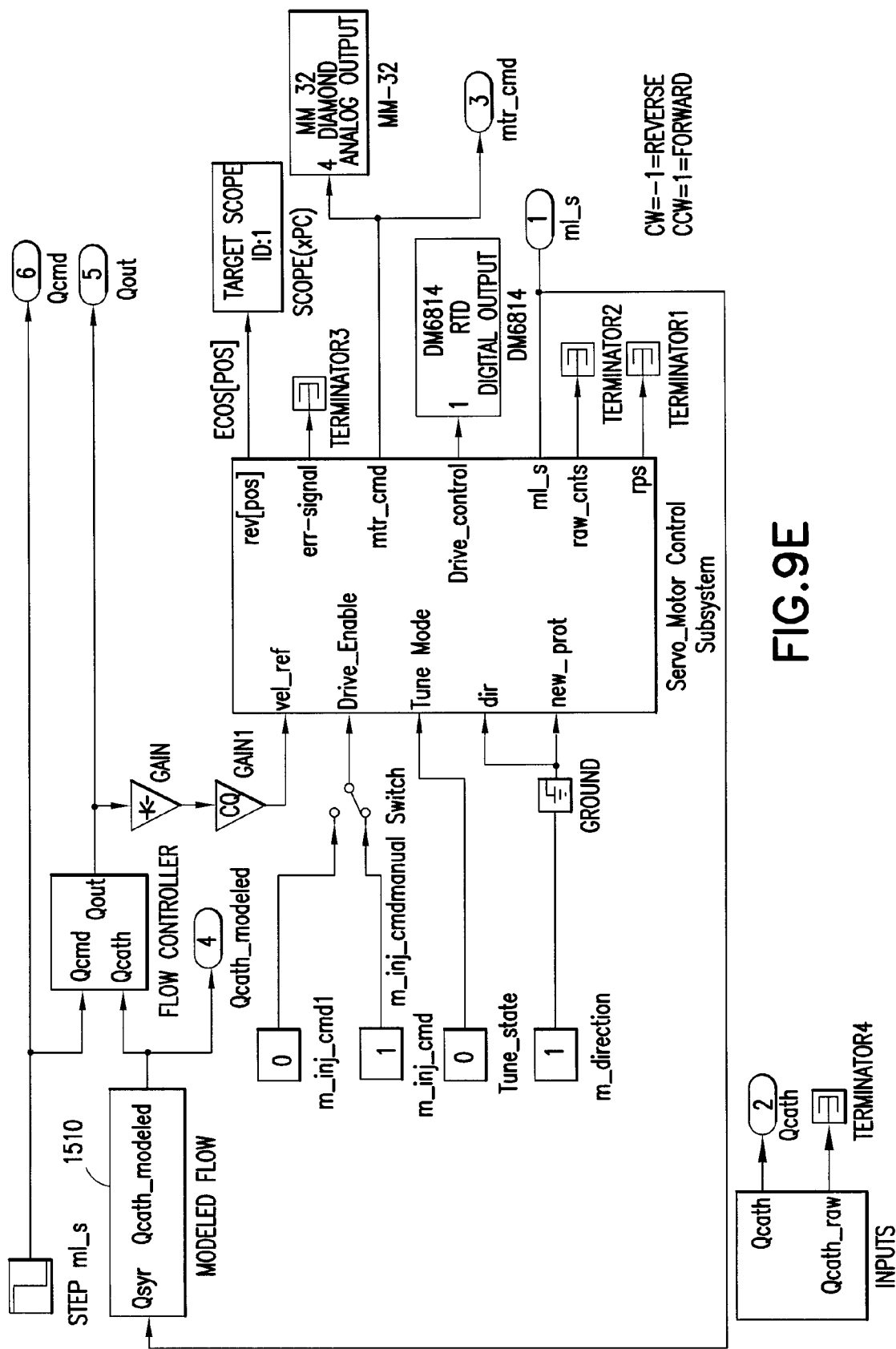

An experimental test was conducted of the basic fluid delivery system 1500 shown in FIG. 9A using the test setup depicted in FIG. 9D. Multiple trials were conducted while measurement of motor velocity of the injector 1501 and distal flow rate from the fluid flow path 1502 were recorded. An algorithm 1510 (see FIG. 9E) modeling the controlled or corrected operation of the fluid delivery system 1500 is set forth hereafter, which is to control the modeled fluid delivery system shown in FIGS. 9E-9F:

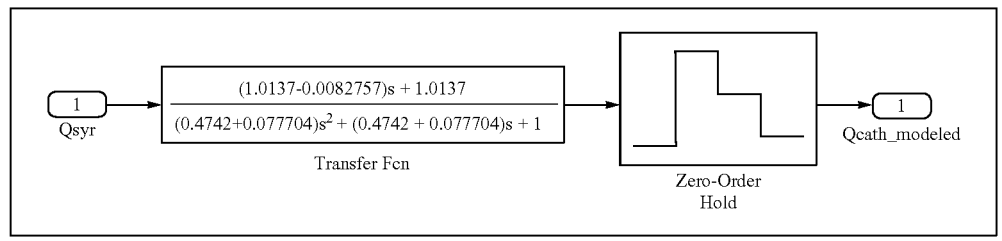

Figure 9G:
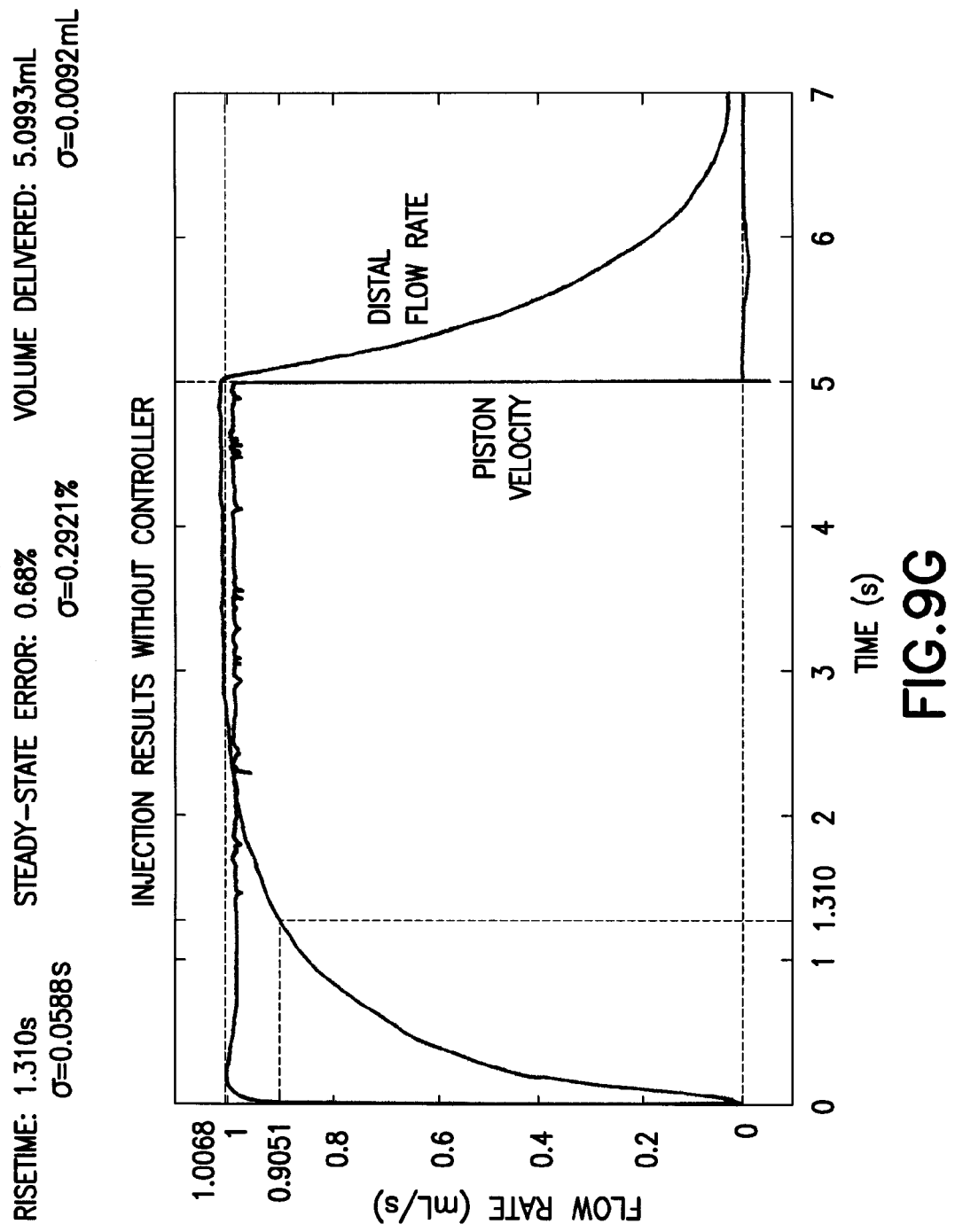
Figure 9H:
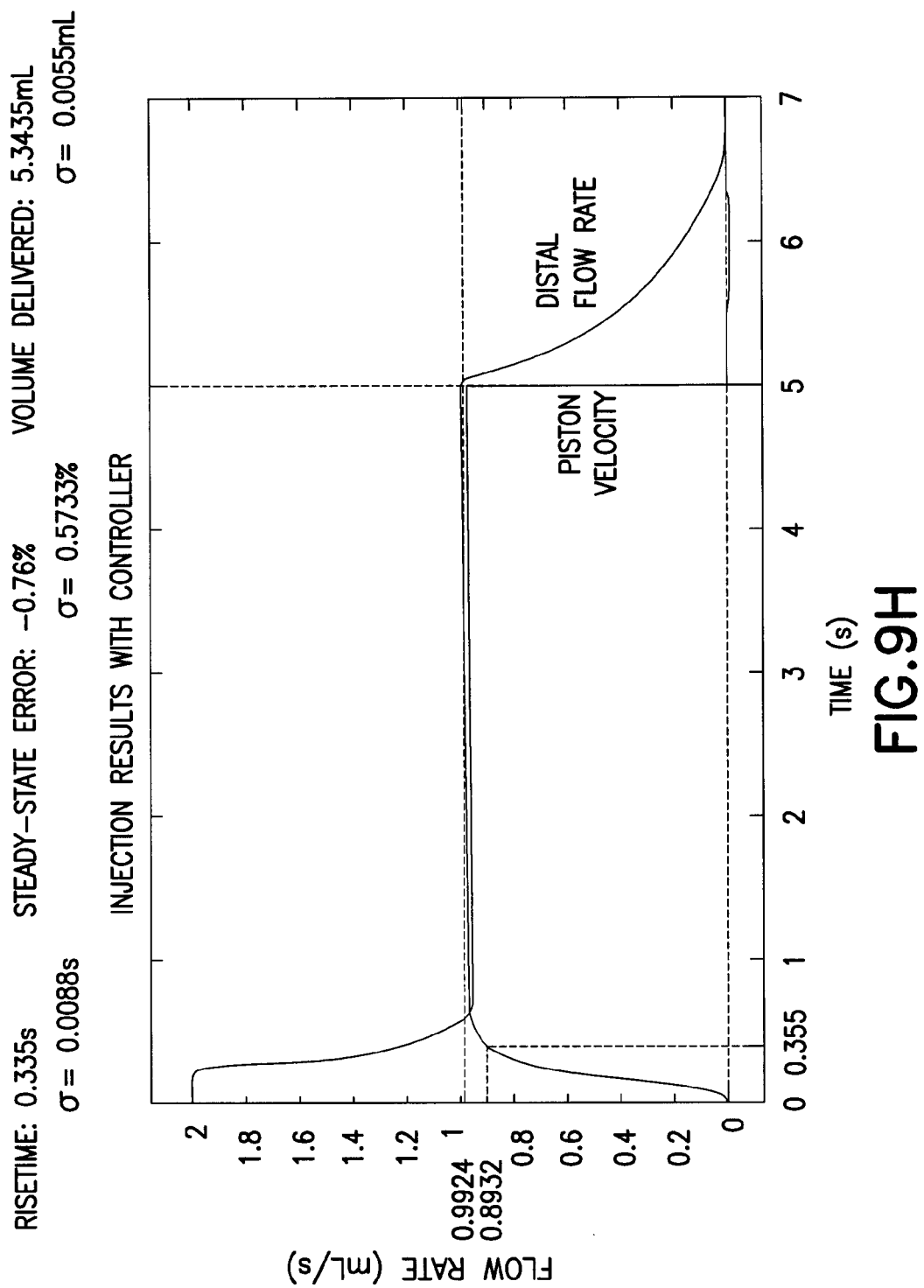
Figure 91:
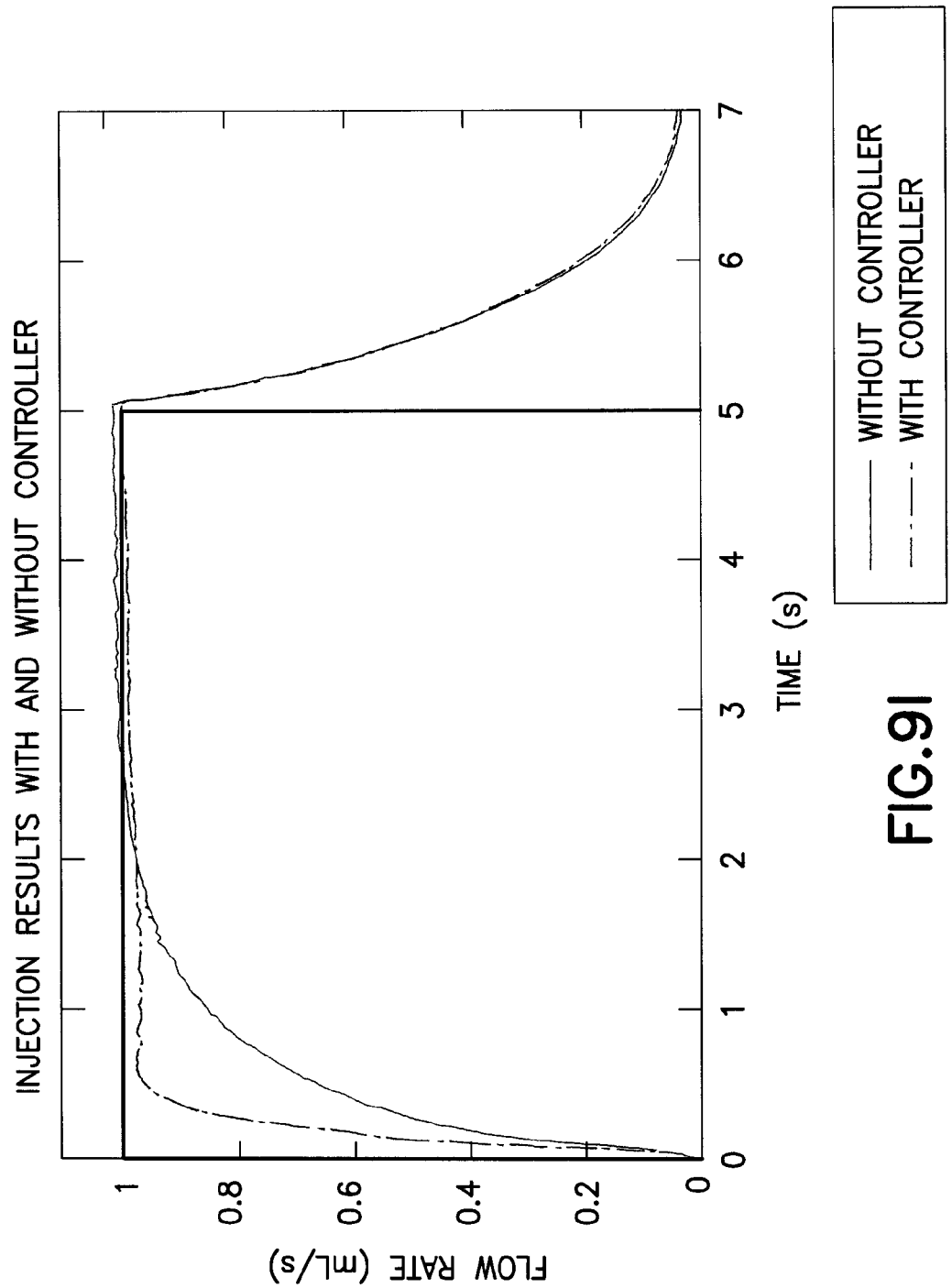

Results of the trials were compared against results from operation of the fluid delivery system 1500 without the control correction afforded by the foregoing algorithm. FIG. 9G is a graphical representation of injection bolus results from fluid delivery system 1500 without control and FIG. 9H is a graphical representation of injection bolus results from fluid delivery system 1500 with the control provided by the foregoing algorithm. FIG. 9I is a graphical representation display of both controlled and uncontrolled results from FIGS. 9G-9H in one graph. From comparing the graphical results from FIGS. 9G-9H, it may be determined that the rising-edge of injection bolus entering the body may be sharpened through algorithm-controlled operation of fluid delivery system 1500. Such controlled operation results in a tighter, more-square bolus which is preferred in many cases for diagnostic and treatment procedures. And, as mentioned herein, having this capability provides the ability to more controllably and repeatedly provide the desired bolus sharpness and profile, even if it is less than the sharpest that is potentially achievable. The foregoing controlling model (e.g., algorithm) takes into account the capacitance of the fluid path elements and actual fluid flow from the fluid flow path 1502 so that the flow out of the fluid delivery system 1500 is controlled, not just the position of the syringe plunger.

In another embodiment, to overcome the dispersion or mixing that occurs naturally from laminar or turbulent flow in fluid path elements, and to some extent by transitions and dead space in the fluid path elements, separating the various fluids by various separators is an option. The separators may be gas, solids, or to some extent a high viscosity, immiscible liquid. An alternative to overcome laminar flow bolus spreading problems is to have the drug introduced concentrically inside the flushing fluid, as shown in FIG. 6A. Drug 4000, which may be a radiopharmaceutical or any desired medical fluid, is pumped through a drug lumen 4001 and travels down the center of the fluid path as the flushing fluid is injected around the outside through outer lumen 4002. Flushing fluid is delivered to outer lumen 4002 via inlet port 4003. Ideally, in laminar flow there is no mixing between the layers and the center flow in a tube flows much faster than the edge, as described previously. Thus, utilizing this concept, providing the drug 4000 into the center of flow moves it along faster than if the drug 4000 was filling the whole outer lumen 4002. More importantly, when the flow of drug 4000 stops, the back edge of the drug 4000 travels faster down the length and out of the outer lumen 4002. This embodiment could be used in drug transport container 1100 with fluid path element 1160 flowing in through the drug lumen 4001 and fluid path element 1165 flowing in through inlet port 4003 and fluid path element 1150 is the tube or conduit down which the two fluids flow. It is advisable to use the drug delivery system of FIG. 5B in this case so that the drug and saline can flow simultaneously.

Figure 7:
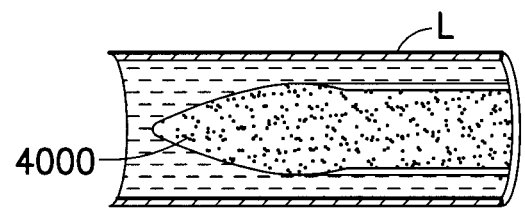
FIG. 7 is an embodiment of a desirable fluid velocity profile for an injection bolus provided by the apparatus and methods described herein.

Optionally, the flushing fluid could be separated from the drug 4000 when it reaches the end of outer lumen 4002 as shown in FIG. 6B. In FIG. 6B, flushing fluid is delivered to outer lumen 4002 via inlet port 4003 and is dispensed from outer lumen 4002 via outlet or exit port 4004. An outlet 4005 of outer lumen 4002 carries the drug 4000 out from outer lumen 4002. If the flushing fluid is withdrawn through outlet port 4004 at a rate equal to which it is injected into lumen 4002 via inlet port 4003, the flushing fluid will carry the drug 4000 along, preventing contact with the lumen wall, before the flushing fluid is withdrawn at lumen outlet 4005. This is beneficial in small animal injections where the total injection volume that can be given to the animal is very low. At the end of the injection bolus, if the drug flow rate is reduced and the flush flow rate is increased so that the total flow remains the same, and this is done at a rate so that the drug 4000 assumes a parabolic profile, as shown in FIG. 7, appropriate for the length of the lumen L being traversed, then the injection bolus tail in the center will "catch up" with the main part of the bolus as it moves the length of the tube as shown in FIG. 8B in relation to the back edge of the injection bolus. The drug 4000 will then exit with a tight, ideally rectangular profile.

Some molecules or drugs used or in development for nuclear medicine or other imaging procedures have a propensity to stick or adhere to various plastics. The placement of the drug in the center bolus as described herein has the benefit of reducing the drug that is lost by adherence to the walls of the tubing.

Another exemplary application that can benefit greatly from both of these embodiments where the drug travels down the center of a tube is angiography, where very viscous contrast media is delivered through narrow catheters. Providing a modest amount of saline or other low viscosity fluid on the outside of the more viscous X-ray contrast media can reduce the pressure drop for a given flow or correspondingly increase the flow for a given pressure. An additional example application is vertebroplasty, where a thick paste of bone cement is injected into bones of the spine to repair a fracture thereof. Additional applications include the filling of an aneurysm, commonly in the brain, or embolization of some deleterious tissue by selectively injecting hard or viscous material into the blood stream to block off the desired blood vessels.

Figure 8A:
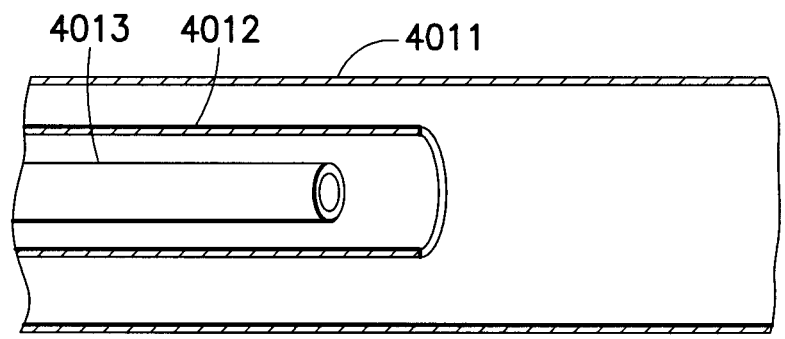
FIG. 8A is a multi-lumen conduit which may be used to achieve a desirable fluid velocity profile for multiple fluids.
Figure 8B:
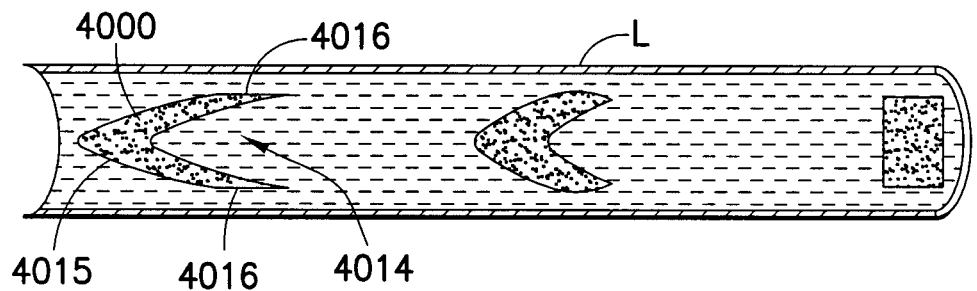
FIG. 8B is an embodiment of a fluid velocity profile for an injection bolus which may be achieved by the multi-lumen conduit shown in FIG. 8A.

In the case of a bolus that is small compared to the length of the tube, having three concentric inlets is advantageous, as shown in FIG. 8A, with the ability to independently control the flow rate of each lumen. Flushing fluid is injected through the first and third lumens 4011, 4013 and the drug 4000 is injected through the second or middle lumen 4012. In operation, flushing fluid is injected through the first and third lumens 4011, 4013 and no drug 4000 is injected. The ratio of the flows in first and third lumens 4011, 4013 is a function of the desired initial radius of the drug bolus. Then, as the flow rate of the drug 4000 injected through the drug lumen 4012 increases, the injection rate of flush through lumen 4011 decreases until the flow through lumen 4011 becomes zero, creating a parabolic profile 4014 shown in FIG. 8B. As this parabolic tail profile 4014 moves down the tube or lumen L, the center 4015 catches up with edges 4016. At the end of the injection bolus, as described previously, the flow rate of the drug 4000 is programmably reduced while that of the flush fluid is increased to create a parabolic tail profile 4014 to the drug 4000. These profiles can be controlled so that the injection bolus occurs as a sharp edge both at the beginning and the end of the injection bolus at the desired location in the lumen L, commonly the end of the tubing forming lumen L.

Figure 10A:
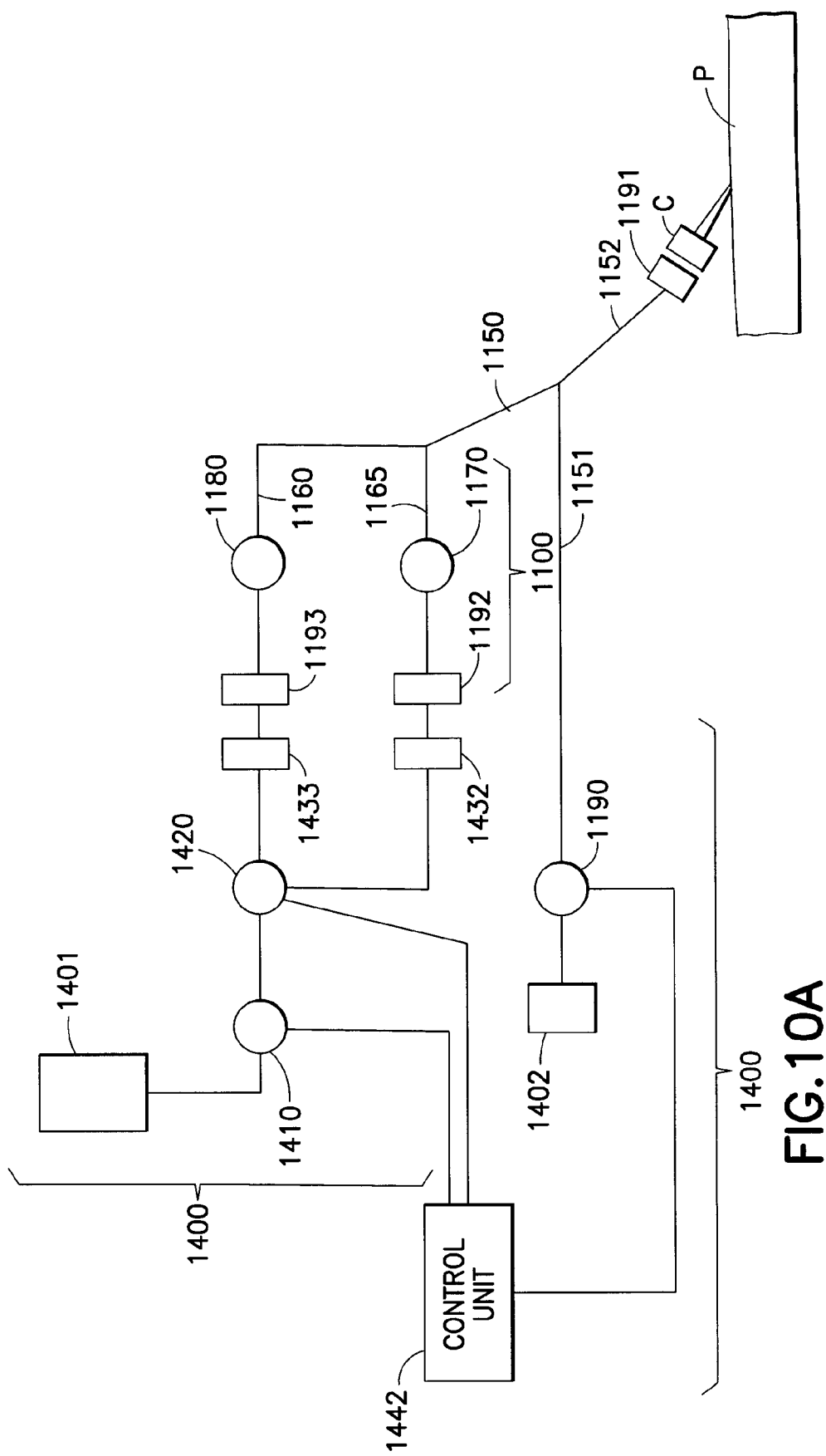
FIG. 10A is a fluid delivery system adapted to inject several fluids in desired injection sequences into a patient.
Figure 10B:
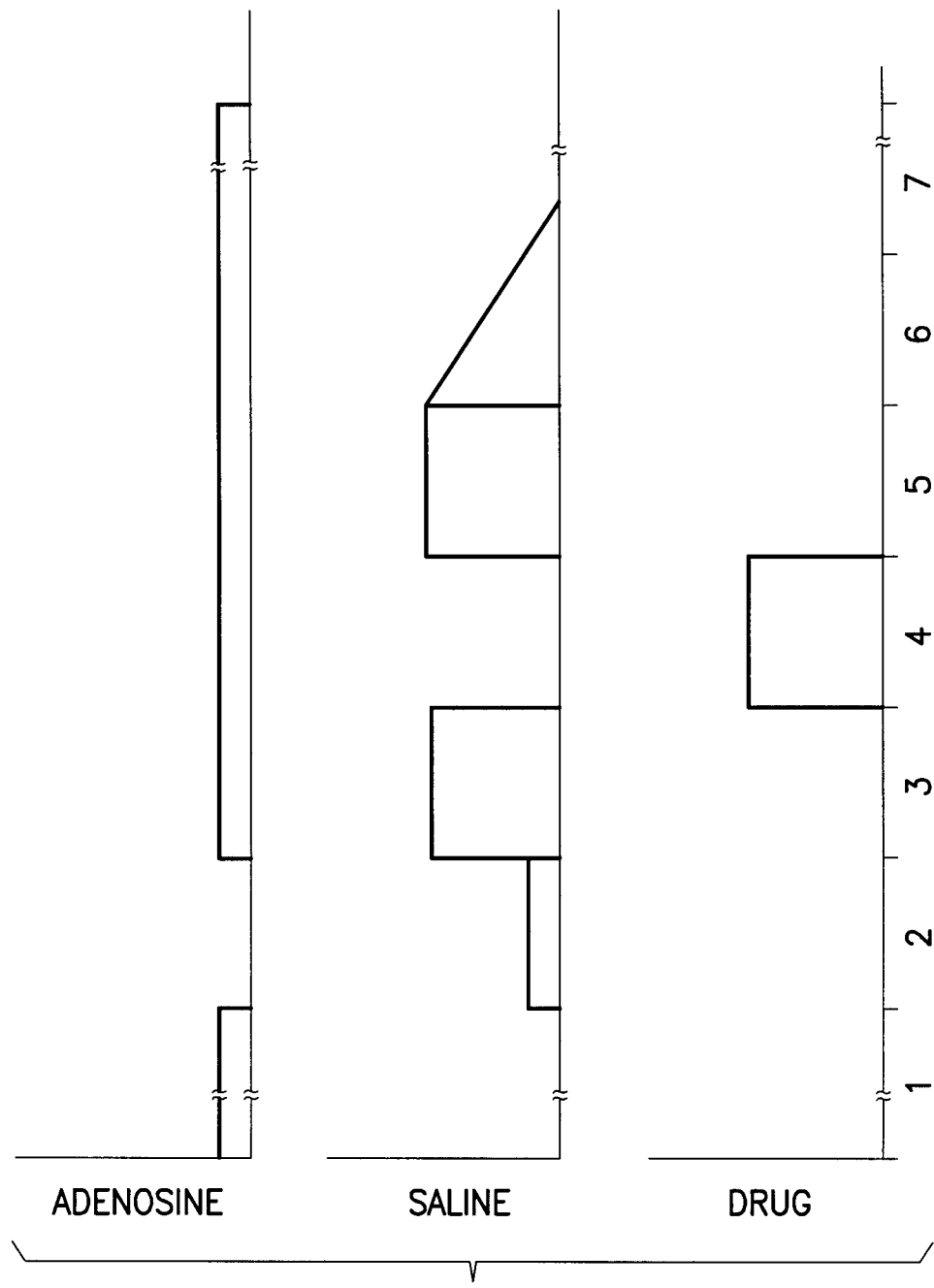
FIG. 10B is a graphical representation of one possible example of a multi-fluid injection sequence provided by the system of FIG. 10A.

Referring to FIGS. 10A-10B, during cardiac first pass imaging using the fluid delivery system shown in FIG. 10A, the patient's heart is stressed either by exercise on a treadmill or bicycle, or, alternatively, by a several minute infusion of a stress agent, for example, adenosine provided in a source container. FIG. 10A illustrates additional features added to the fluid delivery system of FIG. 5C, discussed previously. In FIG. 10A, drug source 1402 comprises adenosine which is injected at a very slow rate by fluid pump 1190 via fluid path element 1151 connected to patient fluid path element 1152, commonly on the order of 60 ml over 4 or 6 minutes. This injection is in contrast to the fluid contained in fluid or drug transport container 1100 and saline 1401 which is injected via fluid pump system 1400 and fluid path element 1150 into patient fluid path 1152 at several milliliters per second. There can be a significant problem when the fast saline or injection drug bolus flows into patient fluid path element 1152. This injection bolus pushes all the adenosine from drug source 1402 that is slowly moving in patient fluid path element 1152 and in the patient's arm veins into the central circulation as one large bolus instead of as a steady flow. This large bolus of adenosine can overstress the patient. The system of FIG. 10A integrates the control of the stressor adenosine infusion provided by pump unit 1190, and the fluid from drug transport container 1100 and saline from saline source 1401 provided by the fluid pump system 1400 to overcome this problem. As illustrated in FIG. 10A, a programmable control unit 1442 controls operation of adenosine pump unit 1190, saline and fluid injection pump unit 1410, and control valve 1420. An example sequence of flow profiles (not shown to scale) which may be provided by programmable control unit 1440 is illustrated in FIG. 10B.

In Phase 1 (as identified in FIG. 10B), there is slow infusion via fluid path elements 1151, 1152 of adenosine from drug source 1402 by pump unit 1190 which stresses the patient's heart. When the heart rate is almost sufficient, Phase 2 is started. In Phase 2, the flow of adenosine from drug source 1402 is stopped and the flow of saline from saline source 1401 is started. The saline from saline source 1401 initially is at the same rate as the adenosine infusion and pushes the adenosine out of patient fluid path element 1152. When the volume of saline is sufficient to clear most of the adenosine from patient fluid path element 1152, Phase 3 begins. The flow rate of saline from saline source 1401 is now that of the drug injection and the volume is sufficient to fill the patient's veins. Also in Phase 3, infusion of adenosine from drug source 1402 resumes at the previous slow rate. The adenosine is quickly carried along by the saline, but there is no large bolus or slug of adenosine because patient fluid path element 1152 has been cleared before the high flow rate of saline commences. Once sufficient volume of saline has been delivered, Phase 4 can begin. In Phase 4, the pump unit 1410 delivers the saline from saline source 1401 through fluid path element 1160, rapidly pushing a radioactive drug, for example, in drug transport container 1100 into the patient P. During Phase 4, the slow adenosine infusion continues by pump unit 1190. After the drug is delivered, in Phase 5, the pump unit 1410 continues pumping saline from saline source 1401 to flush the drug out of the patient's veins. If the saline flush were to immediately stop after the delivery of a sufficient volume, then there would be a gap in the delivery of adenosine as the fluid in fluid path element 1152 is now mostly saline. To avoid this precipitous drop in delivered adenosine, the saline flow rate is ramped down gradually. Alternatively or in conjunction with this procedure, the adenosine flow rate can be increased until the patient fluid path element 1152 is primarily filled with adenosine. Then, the saline flush may be stopped and the remainder of the adenosine is delivered as shown in Phase 7.

Other flow profiles may be used with the system and devices of this disclosure because of the programming and operational flexibility of these systems and devices and are considered within the scope of this disclosure. Alternatively, a new pharmaceutical stress agent known as regadenoson has been made available that does not require a steady infusion but can be delivered as an injection bolus. An exemplary embodiment for use with regadenoson includes priming all of the fluid path elements, 1150, 1160, and 1165 with saline and then delivering a standard infusion of 5 ml of regadenoson into fluid path element 1165 and, thereafter, delivering the radiopharmaceutical into fluid path element 1160. For the fluid dispensing or fluid delivery system 1300, an additional fluid path element or branch dispenses the additional regadenoson. For the fluid delivery system 1400 of FIG. 5, it physically remains the same but is operated differently. The fluid in fluid path element 1165 is dispensed quickly, followed by a sufficient volume of saline flush. Then, after the appropriate delay for the drug to take effect, the radiopharmaceutical is dispensed from fluid path element 1160, optionally with additional saline beforehand and with sufficient saline flush following thereafter.

The foregoing variation in the flow rate of various drugs to prevent unintended transient over delivery or under delivery can also be used in embodiments described herein which employ concentric flow arrangements. In this case, the other drug or drugs, for example, adenosine, can be mixed or merged with saline, and then the saline flows on the outside of the drug in the center. Alternatively, if the adenosine is sufficiently diluted, it could be used as the flushing fluid on the outside with the drug in the center and without the need for a separate delivery of saline.

Figure 11:
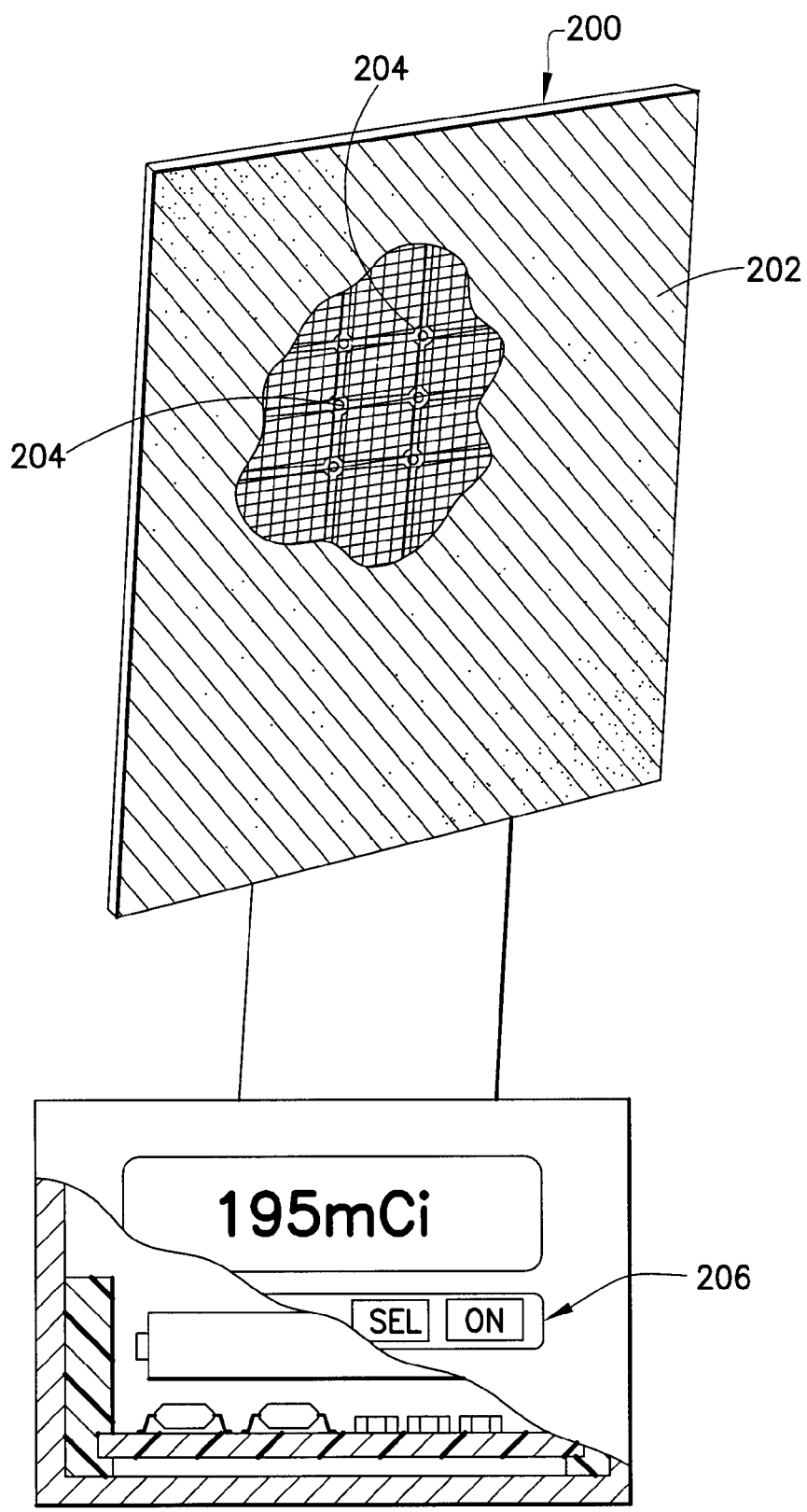
FIG. 11 is a perspective view of an exemplary hazardous fluid collection mat adapted to absorb radioactive fluid spills and alert an attendant.

A further feature of the present invention relates to the use of a mat or pad 200 with a disposable cloth, as shown in FIG. 11, which may be used at certain locations in the fluid delivery systems of FIGS. 5A-5C such as under or around all fluid connection points to absorb or catch any potential radioactive "drips" that may occur. As shown in FIG. 11, mat or pad 200 may be a matrix fabric 202 that is absorbent, such as material used to form disposable diapers. A feature of mat or pad 200 is the association of radiation detectors 204 desirably distributed into the matrix fabric 202 which are electronically connected to a display dosimeter 206. A suitable dosimeter for this purpose is disclosed in U.S. Pat. No. 5,274,239 to Lane et al. incorporated by reference herein. In addition, hand-held shielded wipes with disposable absorbent cloths can be made available for use in handling mat or pad 200. The absorbent fabric 202 forming mat or pad 200 may also include a colored agent such that the color changes when it absorbs any liquid. Moreover, it may be desirable to form matrix fabric 202 in glove form with an associated mini-dosimeter 206 so that an attendant medical professional may be made immediately aware if he or she comes into contact with radioactive liquid. Such gloves may be wholly or partially radiation-shielded to protect the wearer. The dosimeter may include an audible warning of this situation and/or provide a visual warning, for example, going into an intermittent blinking mode or change light colors to inform the glove-wearer of potential radiation exposure. Such gloves may be radiation shielded to limit radiation exposure to the attendant. Optionally, a portable gamma camera similar to those manufactured by eV Products of Saxonburg, Pa., can be used to scan the mat 200 to locate contamination, assess the quantity, and help in determining the source.

As is well-known in the radiopharmaceutical industry, shielding is of particular importance in the protection of personnel involved in the generation, refinement, transport, and delivery of radioactive radiopharmaceutical substances. Many prior art practices for shielding personnel involved with the handling of radiopharmaceutical fluids and like hazardous fluids were described previously in this disclosure. As an example, radiopharmaceutical fluids are often loaded into and transported in a shielded syringe arrangement 300, as shown in FIG. 14. Shielded syringe assembly 300 comprises a syringe 302 which contains the radiopharmaceutical and a shield 304. Syringe 302 includes an outlet 305. Such a shielded syringe assembly 300 is well-known in the art and a typical example may be found in U.S. Pat. No. 4,968,305 to Takahashi, et al., incorporated herein by reference for this purpose. As noted previously, typical syringe sizes for radiopharmaceutical syringes can be about 3 ml in volume and flush syringes (e.g., saline) can be between 20 ml-40 ml in volume. Certain drugs, adenosine for example, may also be loaded into such larger volume syringes as well. Neither the saline flush nor the adenosine is radioactive, thus no special shielding is needed for the syringe(s) containing them. A challenge in the radiopharmaceutical industry is to minimize the instances in which personnel are exposed to radiation. For example, transport containers (e.g., pigs) are known for the transport of radiopharmaceutical syringes, particularly shielded syringes. Within a medical facility or a nuclear medicine suite, lead lined syringe carriers are commonly used, for example, those available from Pinestar of Greenville, Pa. Generally of small "lunch box" shape, these carriers normally hold a shielded syringe assembly 300 containing a radioactive drug. Even with the use of transport pigs or shielded carriers, medical and other personnel are often required to handle the shielded syringe for radiation calibration activities and other activities such as connecting the shielded syringe to a fluid delivery system used to inject the radiopharmaceutical into a patient. During such activities, personnel are exposed to radiation from the unshielded ends of typical syringe shields and, further, during filling, priming, injection, and flushing operations involving the shielded syringe, personnel can be exposed to radiation from unshielded needles, tubing lines, and other fluid path components (e.g., valves, etc.).

As mentioned elsewhere in this description, it is a common practice to connect shielded syringe assembly 300 to a stopcock which is commonly connected to a tubing line to the patient and a second syringe filled with saline, so that the manual injection of the radiopharmaceutical can be followed rapidly by a saline flush and/or so that all or almost all of the radiopharmaceutical can be removed from syringe 302 and the fluid path. In this process of manually injecting and turning stopcocks, the operator is exposed to ionizing radiation from the drug in the fluid path. In addition, the manual turning of valves and injection causes inconsistent injections.

With the foregoing background information in mind, this disclosure provides an embodiment of a shielded transport container 330, as shown in FIGS. 12-15, which may be used to transport shielded syringe assembly 300 and an associated fluid path set 306 in a safe manner to, for example, a location where the shielded syringe unit 300 may be easily interfaced with a fluid delivery system, such as a powered injector unit and the like. An advantage of the shielded transport container 330 includes, for example, the ability to prime the fluid path set 306 up to shielded syringe assembly 300 without having to remove the shielded syringe assembly 300 from shielded transport container 330. Other advantages of this system are that it provides to the patient a tight bolus injection rapidly followed with a flush, while minimizing radiation dose to the operator or technologist; the radiopharmaceutical can be provided in the normal shielded syringe assembly 300, and radiation exposure to the operator and nearby personnel is reduced.

Figure 13:
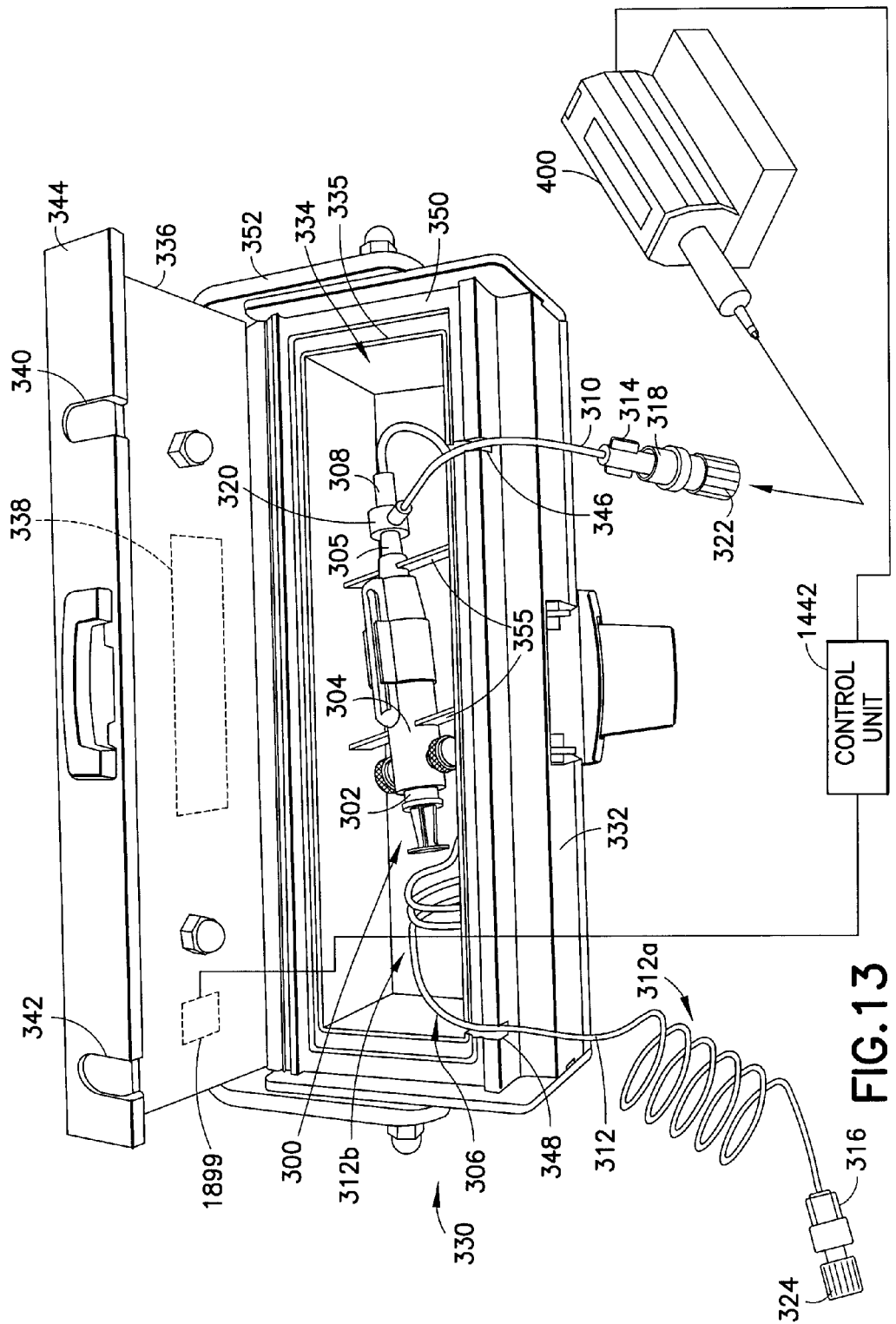
FIG. 13 is a perspective view of the hazardous fluid transport container of FIG. 12 shown in an open state.
Figure 15A:
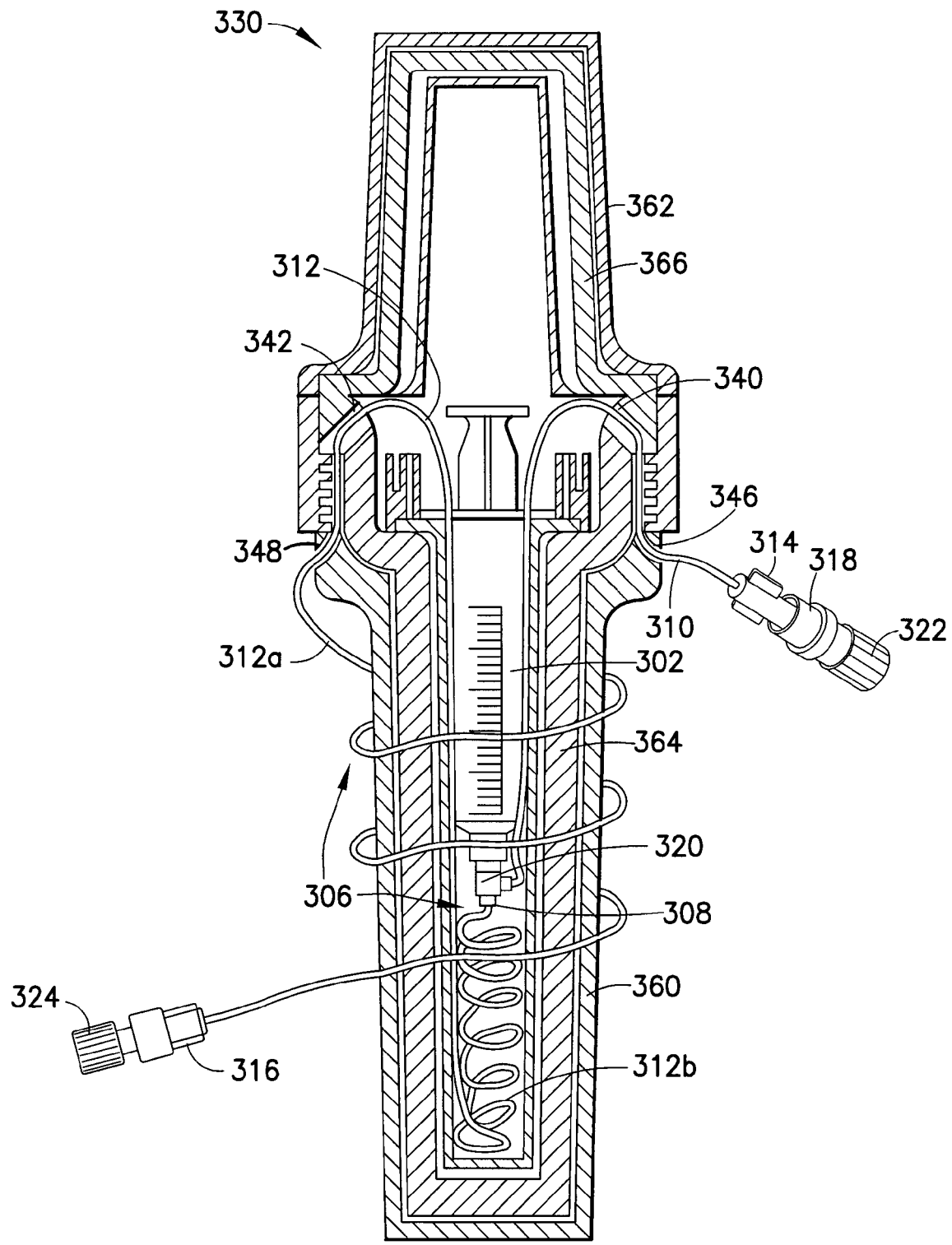
FIG. 15A is a cross-sectional view of another embodiment of the hazardous fluid transport container shown in FIGS. 12-13.
Figure 15B:
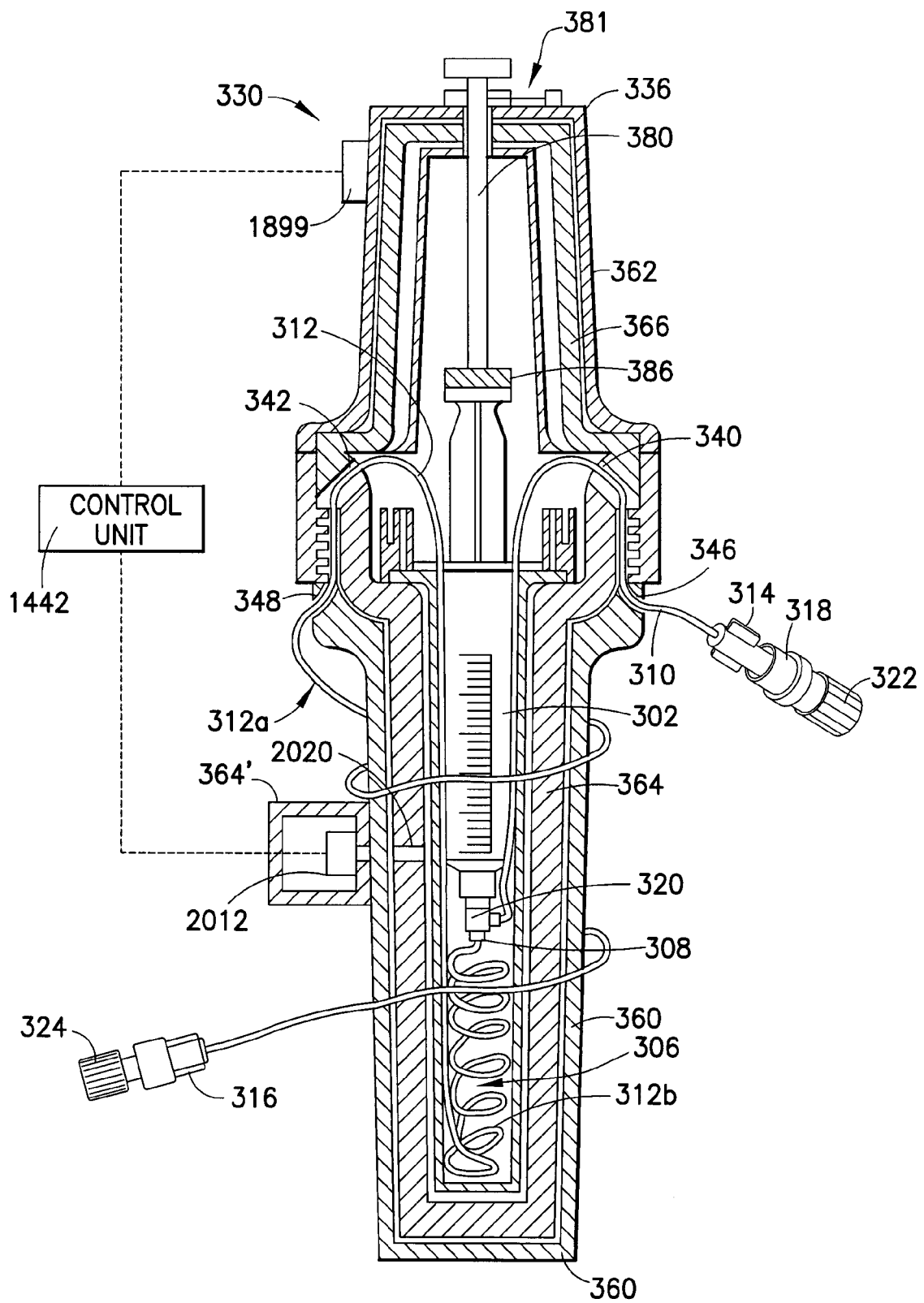
FIG. 15B is a cross-sectional view showing a variation of the hazardous fluid transport container shown in FIG. 15A.

To operate the system, in general, the shielded syringe assembly 300 containing the radiopharmaceutical is connected to a primed fluid path set 306 (which may be primed either before or after connection to syringe 302). It can be primed in any location, for example, in manufacture, in a hot lab, or in a patient injection area. The fluid path set 306 is connected to the patient and to an injector system 400, which can quickly deliver sufficient fluid volume to flush the radiopharmaceutical into the patient. The shielded transport container 330 may also be configured to be physically docked with an injector or "worn" by a patient. In the embodiment of FIG. 13, in exemplary operation, the operator opens the lid of the container 330, manually injects the radiopharmaceutical from the shielded syringe assembly 300 into the fluid path set 306, and quickly closes the lid. The exposure of the operator is limited to this brief time. The operator is not holding the shielded syringe assembly 300 while waiting to inject a patient or while flushing the fluid path set 306. The volume of the fluid path set 306 is chosen so that none of the radiopharmaceutical leaves the shielded transport container 330 until flushed out by saline from the injector system 400. When the radiopharmaceutical is to be delivered to the patient, the injector system is triggered and it controllably pushes the saline flush into and through the fluid path set 306, controllably flushing the previously primed fluid located in the fluid path set 306, followed by the radiopharmaceutical, and finally some of the flushing fluid into the patient. In alternative embodiments, one of which is shown in FIG. 15B, a mechanical pushrod 380 or other arrangement could be used so that even the radiation dose to the operator that comes from opening the lid to move the radiopharmaceutical from syringe 302 into fluid path element 306 can be further reduced if not eliminated. The push rod 380 may either be of material that is sufficient for shielding or incorporates a shielding element 386 which reduces exposure to the operator. The shielded transport container 330 also optionally has a push rod 380 securing device 381 to prevent accidental activation of the push rod 380. This feature is shown schematically as a thumb screw in FIG. 15B. Alternatively, the push rod 380 may engage the shielded transport container 330 in a threaded locking arrangement so that some amount of turning is required before the push rod 380 is disengaged and can move forward to push fluid from the syringe 302. Additionally, the push rod 380 may be connected directly to a powered injection system for operation without manual intervention.

The use of shielded transport container 330 provides a highly portable and mobile containment unit for shielded syringe assembly 300 and one that also contains drips and leakage during transport. Shielded transport container 330 is illustrated in a simple box form in FIGS. 12-13 for exemplary purposes only and it is within the scope of this disclosure to configure shielded transport container 330 in such a manner where it may interface directly with the housing and/or support structure of a powered injector device, such as the MEDRAD Stellant™ injector described previously. By "interface", this disclosure includes situations where shielded transport container 330 is physically docked with an injector device and situations where shielded transport container 330 is supported on support structure associated with the injector or its fluid handling components, for example, a conventional injector support tree or even a conventional IV pole. Illustrated injector 400 is provided for exemplary purposes and does not include associated support structure as described in the foregoing. Alternatively, as illustrated, the shielded transport container 330 may be placed near the injector device 400 a tubing line from the injector device 400 is run to an inlet connection 314 comprising an inlet check valve 318. Additional mounting and integration methods, designs, devices, and systems are illustrated, for example, International Publication No. WO 2008/011401A2 (International Application No. PCT/US2007/073673) which is incorporated herein by reference.

As noted in the foregoing, powered fluid injectors may have a dedicated support stand/structure and shielded transport container 330 may interface directly with such a support stand/structure. In the case of a physical integration with an injector device, additional components (not shown) may be associated with the injector device that are unique to the physical integration feature and/or are adapted specifically to the hazardous fluid contained in the shielded syringe assembly 300. For example, the injector may have a sensor to identify when the shielded transport container 330 is physically docked with the injector, with this information being communicated to an onboard or externally located control unit 1442 controlling injector operation. As discussed elsewhere in this disclosure, a dosimeter may also be provided on the injector and interface with, for example, an aperture or opening in the shielded transport container 330 so that a reading of radioactivity of the shielded syringe assembly 300 may be obtained and transmitted, for example, to the injector control unit (internal or externally located). Further, shielded transport container 330 may be marked with identifying indicia (e.g., bar codes and the like) or have other identifying/data storage or memory devices 1899 (e.g., RFID tags or memories) which may be read and/or written to by sensors on the injector and transmitted to the injector control unit so that injector operation may be controlled by the control unit based on this scanned or sensed information. In addition, the injector 400 or control unit 1442 may also write or record information to identifying/data storage device 1899 which can subsequently be used to transfer information related to the procedure or the dose the patient received. In general, it is contemplated that shielded transport container 330 may be adapted for a custom fit to the injector and/or its support structure and additionally or alternatively include custom fit fluid connections to the fluid path elements associated with the injector.

Conventional shielded materials may be used in connection with the body of shielded transport container 330, including lead, tungsten, tungsten loaded plastic, lead acrylic, as examples. Additionally, other embodiments of shielded transport container 330 may be tailored to the shape of the shielded syringe assembly 300, to variations in the fluid path set 306, to variations in the imager or patient facility with which shielded syringe assembly 300 and fluid path set 306 are cooperating, and to the injector with which shielded syringe assembly 300 and fluid path set 306 are interfaced. For example, shielded transport container 330 may be formed to exhibit the shape of shielded syringe assembly 300 and, thereby, receive in a mating engagement the shielded syringe assembly 300. Thus, shielded transport container 330 may be custom formed to accept shielded syringe assembly 300, for example, by forming shielded transport container 330 from curved lead, cast lead into the desired form, and injection molded radiation shielding material. Alternatively, shielded syringe assembly 300 may be formed for a custom fit into shielded transport container 330.

Shield transport container 330 generally comprises a container body portion 332 defining an internal compartment 334 and a closure lid 336 for enclosing the internal compartment 334. The internal compartment 334 defined by container body portion 332 may be sized and/or include internal structure configured to receive and mate with the shape of shielded syringe assembly 300, or multiple such assemblies 300. In such an alternative, the "mating" internal structure may comprise shielding material while surrounding structure forming shielded transport container 330 is unshielded. An "on-board" dosimeter may also be provided in shielded transport container 330 to obtain radioactivity readings in internal compartment 334, as described in International Application No. PCT/US07/89101 (WO 2008/083313) and U.S. Pat. No. 5,274,239 to Lane et al., both previously incorporated by reference. Desirably, such internal radioactivity readings are communicated to an operator of the fluid delivery system including the powered injector 400 and shielded transport container 330, such as by a display on the body of the shielded transport container 330 or on a display associated with the injector 400 and/or the control unit 1442 associated with the injector 400. Such a dosimeter may provide inputs to the injector control unit so that the control may identify the contents in the shielded syringe unit 300 based on measured radioactivity level. Furthermore, it is desirable for a radiation-shielded window 338 to be provided on the shielded transport container 330 so that attendant personnel may visually inspect the contents of the shielded transport container 330 as well as any fluid connection elements associated with, for example, shielded syringe assembly 300 and disposed in internal compartment 334. This visual check capability has importance in the area of air bubble detection should priming operations (to be discussed herein) relating to shielded syringe assembly 300 fail to fully purge air from the shielded syringe assembly 300 and its associated fluid path elements. Internal lighting (not shown) may be provided in internal compartment 334 to assist in the visual inspection of the shielded syringe assembly 300 and the fluid path components associated therewith.

Another feature of shielded transport container 330 is the provision of a removable and disposable internal tray unit, as represented schematically in FIG. 13 and identified with reference numeral 335, or similar structure within internal compartment 334 which may simply be discarded as hazardous medical waste after removal of shielded syringe assembly 300 once the contents of the shielded syringe assembly 300 have been dispensed to a patient. Removable tray or structure 335 may comprise internal walls 355 or like supporting elements to support shielded syringe assembly 300 and/or restrain fluid path 306 in internal compartment 334. As noted in connection with FIG. 11, mat or pad 200 may be used around fluid connection points to absorb or catch any potential radioactive "drips" that may occur. Such a mat or pad 200 may be adapted in a "tray" form and provided within internal compartment 334 to absorb leaks, drips, and spills therein. Such a disposable tray may simply be emptied from shielded transport container 330 and into an appropriate radiation-shielded medical waste receptacle. Moreover, it will be appreciated that a liquid tight seal is desirable between the container body portion 332 and closure lid 336 to prevent leakage of hazardous fluid such as radiopharmaceutical fluid. Moreover, the "tray" formed by mat or pad 200 may also contain and fix (geometrically or spatially) the various fluid path elements of fluid path set 306 as well as syringe 302 and shield 304 in a similar mechanical manner to that mentioned previously in connection with FIG. 4.

A pair of openings 340, 342 is defined in a front rim 344 of container closure lid 336, generally at opposing ends of the closure lid 336. Such openings 340, 342 register with similar openings 346, 348 defined in a rim 350 in container body portion 332. A handle 352 may be provided on container body portion 332 to facilitate carrying the shielded transport container 330.

As shown in FIGS. 13-14, shielded syringe assembly 300 generally comprises a radiopharmaceutical syringe 302 and a surrounding syringe shield 304. Such components are well-known in the radiopharmaceutical industry. A fluid path set 306 is connected to outlet 305 of syringe 302 and comprises a check valve T-connector 308, containing a check valve 320 arranged so that fluid can flow from syringe 302 into fluid path elements 310 and 312, but not back into syringe 302, and inlet and outlet connectors 314, 316, respectively associated with inlet fluid path element 310 and outlet fluid path element 312. Inlet fluid path element 310 may be a straight or coiled inlet fluid path element and outlet fluid path element 312 may be similarly configured. An example of a fluid path set generally similar to that described above is the product MRI Integral "T" with Check Valve, catalog number SIT 96V, currently available from MEDRAD, Inc. of Pittsburgh, Pa. Such inlet and outlet connectors 314, 316 are desirably conventional luer-type connectors, with the inlet connector 314 additionally comprising a check valve 318 permitting inflow into fluid path element 310 and thus into fluid path element 312 but not in the reverse direction. Check valve 318 is also chosen with a crack pressure sufficiently high that fluid will not flow out under gravity, but only when driven by a flushing fluid from injector 400 or like pressurizing device connected to inlet check valve 318. Check valve 318 may alternatively be on the outlet side, associated with outlet connector 316, or anywhere along the fluid path set 306. Optionally there may be check valves at both ends or multiple check valves along the path to provide some redundancy so that occurrence of drips of radioactive material is minimized. Check valve 320 prevents fluid flow into syringe 302 via T-connector 308. T-connector 308 comprises an outlet check valve 320 that permits outflow from syringe outlet 305 to outlet fluid path element 312. Sterile end caps 322, 324 may be associated with inlet check valve 318 and outlet connectors 314, 316 respectively.

As revealed in FIG. 13, once shielded syringe assembly 300 is placed within shielded transport container 330, inlet fluid path element 310 may be associated with registered "inlet" openings 340, 346 and outlet fluid path element 312 may be associated with registered "outlet" openings 342, 348, thereby making inlet and outlet connectors 314, 316 accessible outside of the shielded transport container 330. The outlet fluid path element 312 has two parts, namely, segment 312b that is inside shielded transport container 330 and segment 312a that is outside of container 330. Segment 312b is used to contain the radiopharmaceutical when it is ejected from the syringe 302 for delivery to the patient and subsequent flush, and this operates similarly to fluid path element 1160 of FIG. 2, containing a radiopharmaceutical for subsequent delivery. Segment 312a operates similarly to fluid path element 1150 of FIG. 2. There is no fluid path element similar to fluid path element 1165 in this embodiment, but one could be added to gain the full functionality of the previously discussed embodiment. The use of coiled medical tubing for the outlet fluid path element 312 permits attendant personnel to draw the tubing as needed to interface fluid path set 306 with, for example, an indwelling patient catheter or IV line. If desired, inlet fluid path element 310 may comprise coiled medical tubing, allowing it to stretch to an injector which may be remotely located. The coiled segments of outlet fluid path element 312 may initially come fully or primarily contained in the shielded transport container 330 for neatness and convenience, with the user then pulling tubing as needed. Additionally, "outlet" openings 342, 348 may be sized and/or include an elastomeric braking lining to limit how quickly the tubing of the outlet fluid path element 312 may be pulled outward from the shielded transport container 330. Preferably, there is a stop associated the outlet fluid path element 312 so that no portion of internal tubing segment 312b may be pulled out of the shielded transport container 330. Such features may also be provided or associated with the registered "inlet" openings 340, 346 as well.

If desired, shielded syringe assembly 300 and fluid path set 306 may be provided as a unitary cassette or cartridge component that "plugs" into a receiving structure (not shown) in internal compartment 334 defined by container body portion 332. Such a cassette or cartridge may be marked with identifying indicia (e.g., bar codes and the like) or have other identifying devices (e.g., RFID tags) which may be read by sensors in internal compartment 334 and which may be transmitted by a wired or wireless connection to a control unit associated, for example, with a powered injector so that injector operation may be controlled at least in part by this scanned or sensed information concerning the contents of the cassette or cartridge within the internal compartment 334. It will appreciated that such internal sensors in internal compartment 334 may be capable of other actions including determining the presence of the cassette or cartridge, identifying whether a fluid path set, such as fluid path set 306, is present or even that valves and connectors associated with the fluid path set are correctly positioned and interfaced with the sensor(s). In one embodiment, the internal sensors could be air or air bubble detectors associated, for example, with registered sets of openings 340, 346 and 342, 348 to detect the presence of air bubbles in the inlet and outlet fluid path elements 310, 312. Lighting may be provided in the registered sets of openings 340, 346 and 342, 348 to assist attendant personnel with air or air bubble detection and other activities such as priming the fluid path set 306 with priming fluid such as saline as described herein.

If desired, the internal compartment 334 in container body portion 332 may be divided such that the syringe 302 and accompanying syringe shield 304 are disposed in one segregated area while the components of the fluid path set 306, discussed previously, are disposed in a separate area from the syringe 302 and syringe shield 304. In such a circumstance, closure lid 336 may be bifurcated so that the separate internal areas for the syringe 302 and syringe shield 304 and the fluid path set 306 are separately accessible. Moreover, while the foregoing discussion generally relates to the housing of a single shielded syringe assembly 300 within shielded transport container 330, this should not be considered as limiting the scope of the invention to a single such application. It may be desirable to adapt shielded transport container 330 to enclose several shielded syringe assemblies 300 containing like or different hazardous fluids, for example multiple isotopes such as technetium and thallium, to be used in a nuclear medicine study of a single patient. The internal compartment 334 of container body portion 332 may be configured to accept multiple shielded syringe assemblies 300 and comprise segregated internal areas for the syringes 302/syringe shields 304 and fluid path sets 306. Thus, shielded transport container 330 may comprise a container body portion 332 and closure lid 336 which have multiple sets of registered openings 340, 346 and 342, 348 to accommodate multiple fluid path sets 306. Such multiple fluid path sets 306 may be in parallel and joined at a designated downstream connection point such as an indwelling patient catheter, as an example, or before exiting the shielded transport container 330.

Figure 12:
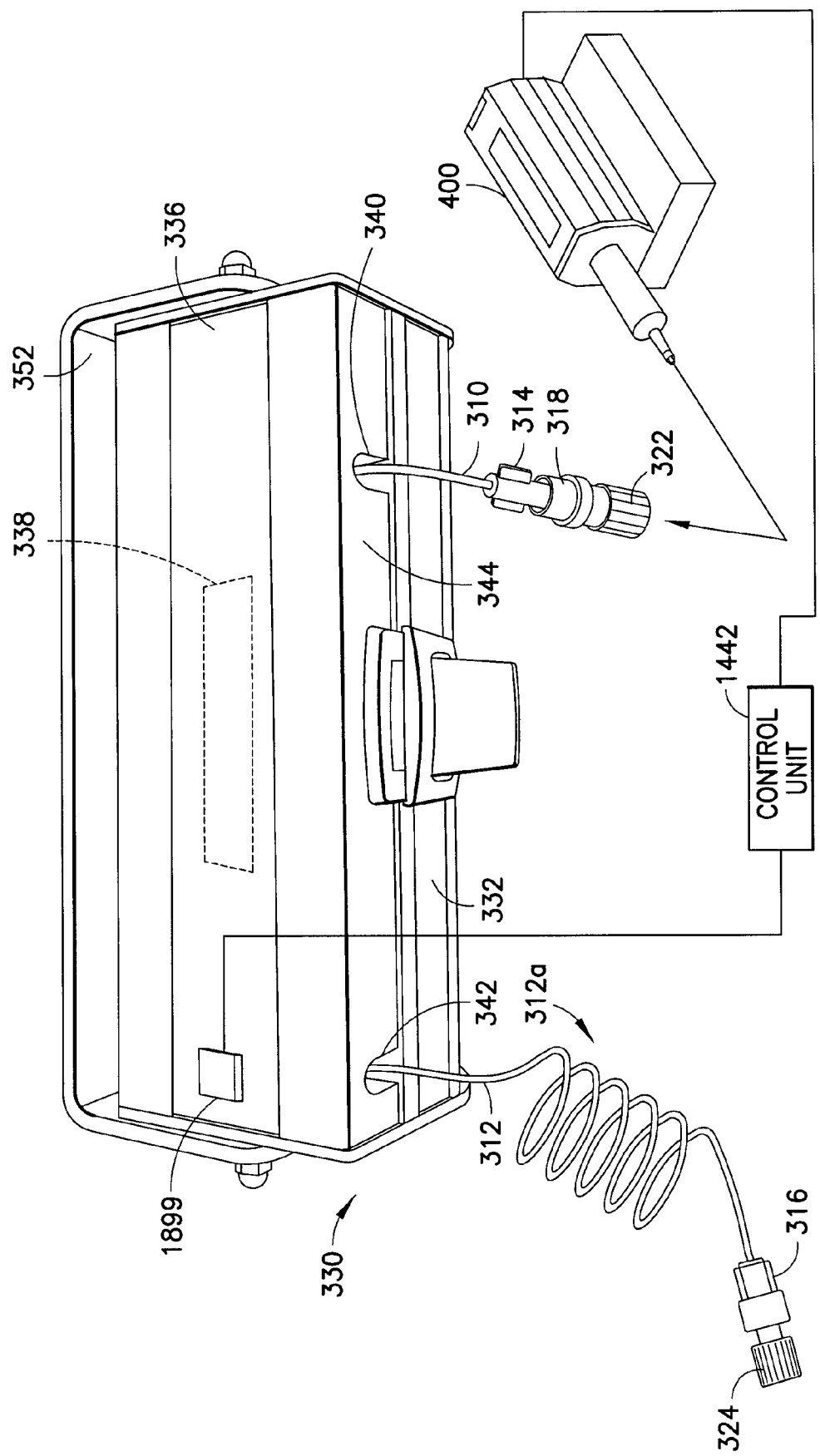
FIG. 12 is a perspective view of an exemplary embodiment of a hazardous fluid transport container.

As noted, it will be clear that the depicted box-shape of shielded transport container 330 shown in FIGS. 12-13 should not be considered as limiting. Other possible configurations, beyond the illustrated "lunch box" shape include a clam shell configuration or a transport pig configuration such as that disclosed in U.S. Pat. No. 6,425,174 (Reich) assigned to Syncor International, previously incorporated herein by reference. FIG. 15A illustrates modifications to the basic transport pig described in the foregoing Reich patent resulting in a "pig type" shielded transport container 330 according the present invention. The Reich patent discloses the basic components of a conventional transport pig and the following discussion relates to modifying that structure to obtain the pig shielded transport container 330 shown in FIG. 15A. In FIG. 15A, the internal tubing segment 312b of the fluid path set 306 that is to be shielded can be coiled in internal space normally allotted for the needle in a transport pig, with the transport pig being modified to provide an internal labyrinthine path for the two ends of the fluid path set 306 to exit the transport pig. The coiled, external tubing segment 312a of fluid path set 306 may be coiled around the outside of the "pig" shielded transport container 330, as shown in FIG. 15A.

The pig shielded transport container 330 as illustrated in FIG. 15A further modifies the basic transport pig of the Reich patent to include openings 346 and 348 in the sidewall of lower shell 360. Lower shell 360 is adapted to interface with upper shell or closure lid 362 via a threaded connection. Radiation shielding components 364, 366 reside within lower shell 360 and upper shell 362, respectively. Lower shielding component 364 likewise defines openings 340, 342. As shown in FIG. 15A, inlet fluid path element 310 passes through inlet openings 340, 346 and outlet fluid path element 312 pass through inlet openings 342, 348. In the present embodiment, shielded syringe assembly 300 does not necessarily require a separate radiation shield 304 associated with the syringe 302 as radiation shielding is provided by components 364, 366. The pig shielded transport container 330 alone provides sufficient shielding and the syringe 302 need not be removed from the container 330.

As stated previously, a desirable feature of the combination of shielded syringe assembly 300 and shielded transport container 330 is the ability to prime fluid path set 306 with a priming fluid such as saline, for example, in the nuclear medicine lab where the dose is prepared, prior to associating the shielded syringe assembly 300 with, for example, a powered injector unit 400. In particular, inlet fluid path element 310 may be connected via inlet connector 314 and check valve 318 to a source of priming fluid such as saline. Inlet check valve 318 prevents inflow of saline under gravity, but only conducts fluid under the greater pressure supplied from an injector 400 or even a hand syringe, for example, through inlet fluid path element 314 and into T-connector 308. Saline passes through T-connector 308 (but not into syringe 302 due to outlet check valve 320) to fill outlet fluid path element 312 with priming fluid. Once outlet fluid path element 312 is primed with saline, terminal end cap 324 may be provided on outlet connector 316 to seal the outlet fluid path element 312. Once the priming operation is complete, attendant medical personnel may carry the shielded transport container 330 to the room where the patient is to be injected. It is preferred that the syringe 302 and fluid path set 306 remain in the shielded container 330. Alternatively, if required, the operator can remove the primed shielded syringe assembly 300 and associated fluid path 306 and mount the same to powered injector 400 with sufficient or appropriate shielding, as an example. The outlet end cap 324 may be removed and the outlet connector 316 connected to a catheter or IV line connected to a patient. The outlet connector 316 is connected to the patient and inlet connector 314 is connected to the injector 400. The operator then manually injects all the radiopharmaceutical from syringe 302 into tubing segment 312b, and closes the lid on the shielded transport container 330. Thereafter, injection of the radiopharmaceutical fluid or other hazardous fluid in syringe 302 may commence when the operator triggers the powered injector 400. Radiation exposure is minimized during the priming operation as the radiopharmaceutical-containing syringe 302 is retained in the shielded transport container 330 throughout the priming operation. Moreover, after injection of the radiopharmaceutical fluid in syringe 302, the check valve arrangement in fluid path set 306 allows the entire fluid path set 306, including inlet fluid path element 310 and outlet fluid path element 312, to be flushed with saline or another fluid so that any residual radiopharmaceutical fluid in the outlet fluid path element 312 is pushed into the patient. It will be apparent that inlet fluid path element 310 may be connected to a saline flushing source and a pump device, such as a peristaltic pump, which provides the saline under pressure in fluid path set 306 to flush radiopharmaceutical fluid into the patient. Such a pump device may also be used in conducting the priming operation discussed previously. Alternatively, the fluid path set 306 may be transported to the patient injection room with the fluid path segments 310 and 312 unprimed. The inlet connector 314 may then be connected to the injector, and the fluid path segments 310 and 312 are primed before the outlet connector 316 is connected to the patient. While shielded transport container 330 is illustrated in FIGS. 12-14 as a box-like structure this should not be considered as limiting as the shielded transport container 330 may have any desirable shape such as the transport pig structure shown in FIG. 15A, as described in the foregoing.

The details of the preparation and connection of shielded syringe 302 comprising an enclosing shield 304 to fluid path 306 can be used to create small bubbles at either or both ends of the radioactive drug bolus which can reduce bolus spreading as the drug flows through the lengths of tubing, similar to the use of $CO_2$ in the earlier described embodiments. In current practice in the nuclear medicine field, as a syringe is filled from a vial using a needle to pierce a rubber septum and there is resulting radioactive drug in the needle. In the present embodiment, before such a syringe can be connected to the fluid path set 306, the needle must be removed. In this embodiment, it is preferred that the fluid in the needle be pulled into the syringe, along with a fraction of a ml of air. This ensures that the needle is empty and provides one of the fluid separation "bubbles" pursuant to previous aspects described hereinabove. Then, the needle is removed and safely discarded. When connecting the shielded syringe 302 with shield 304 or an unshielded syringe 302 to the fluid path set 306, there is a small bubble in the luer connector (typically female) of the T-connector 308 and in the luer connector (typically male) of the syringe 302. Thus, unless something special is done, there will be a small air bubble that is injected into the fluid path element 312b when fluid is first pushed from the syringe 302. Then, while delivering the fluid from the syringe 302, preferably holding the syringe vertical with the luer connector on the syringe 302 pointed down, a small bubble from the air that was drawn into the syringe previously is injected into fluid path element 312b. Through this procedure, small bubbles of air bracket the bolus of drug and help maintain a sharp bolus profile as it travels through the various fluid path elements on its way to the patient; this procedure is similar to the way $CO_2$ was used in the embodiments associated with FIG. 4.

The various descriptions in this disclosure relating to the use of a "tray" element or like component to spatially fix tubing segments or like fluid path elements (e.g., some or most of fluid path set 306) and create a replaceable module or cassette that is easier for a user to install is very beneficial. In addition, this arrangement has advantages when used in relationship to a radiation dosimeter or dose measuring element or device. In many devices and methods wherein radioactive materials and fluids are present, a dose calibrator is often used which typically employs a hollow cylindrical ion chamber where a container with the radiation dose to be measured is inserted into the center of the ion chamber. Such ion chambers are manufactured, for example, by Veenstra Instrumenten B.V. of the Netherlands. In the Intego™ PET Infusion System manufactured by MEDRAD, Inc, a fluid path element, a tube, is coiled on a simple tray, in this case a cylindrical form, which is placed in the hollow of an ion chamber for measurement of the dose. The benefit of a hollow ion chamber for use as a dose calibrator is that it effectively senses most of the radiation emitted from the material located therein and the measurement is substantially independent of the precise position of the radiation emitting material within the hollow space. Thus, an ion chamber can work well for measuring the radiation in a reasonable range of sizes of syringes, vials, or coiled tubes, but this type of radiation detector is large and expensive.

Alternatively, in U.S. Pat. Nos. 4,562,829 and 4,585,009 (both to Bergner) and in United States Patent Application Publication No. 2005/0277833 (Williams), all mentioned previously, small localized radiation detectors are use. In the Bergner patents there is a drawback that only a portion of the radiation to be delivered is measured at a time. In the Williams publication, measuring the radiation in a syringe with only a point radiation source can produce reading errors. In International Application No. PCT/US07/89101 (WO 2008/083313), previously incorporated by reference, an embodiment is disclosed which uses several small radiation sensors and geometric information to measure radiation in a syringe. This particular embodiment may be employed with the systems, devices, and methods of this disclosure.

Figure 16:
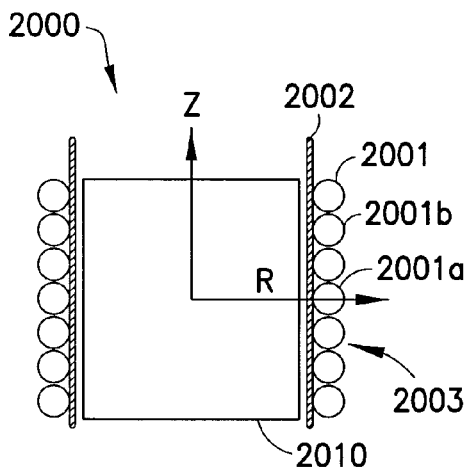
FIG. 16 is a schematic representation of an embodiment directed to detecting radioactivity of a radioactive fluid in a fluid path set comprising tubing.

A radiation detecting system 2000 which is an alternative to a hollow cylindrical ion chamber dose calibrator is represented in FIG. 16. A coiled tubing segment 2001 is held by a tray 2002 to create a module 2003 that can be placed over a simple generally cylindrical radiation detector 2010. Radiation detectors of this general geometry are common, including Geiger tubes, ion chambers, and solid state crystal detectors, as examples. If the whole tubing segment 2001 contains fluid of substantially the same concentration of radioactivity, system 2000 works well. Or, system 2000 works well if only the integral of the dose is measured as the drug flows through the whole tubing set at a constant flow rate. External shielding (not shown) may then be employed to protect workers, to prevent radiation from affecting other devices, and to prevent radiation from getting in and affecting this device. However, there is possibly a problem if the "tight" injection bolus as described earlier in this disclosure is a short compared to the length of the coiled tubing segment 2001 so that it only occupies some of the volume of the coiled tubing segment 2001, or if laminar flow spreads the injection bolus so that the concentration is not uniform throughout the length of the coiled tubing segment 2001, and also if the flow is not uniform or if the measurement of interest is something other than the total dose integrated over the whole transit time. In the embodiment of FIG. 16, the radiation detector will have a greater sensitivity to radioactivity in some coil segments as compare to others, for example, to coil segment 2001a than to coil segment 2001b. This causes non-uniformity in response to the same amount of radioactive drug depending upon where it is in the coiled fluid path or tubing segment 2001.

Figure 17A:
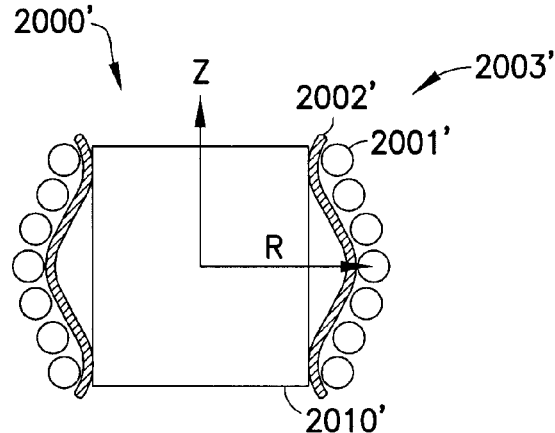
FIGS. 17A-17C are schematic representations of other embodiments of the radioactivity detecting arrangement shown FIG. 16.
Figure 17B:
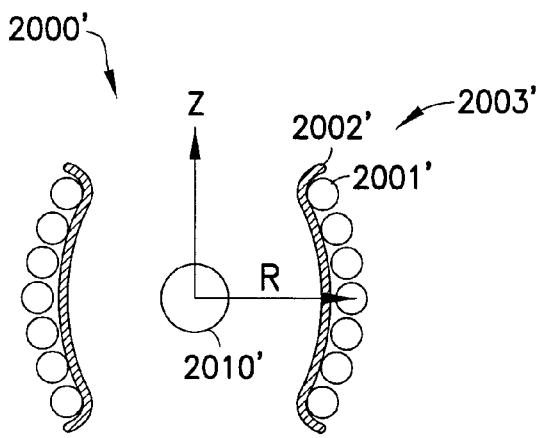
Figure 17C:
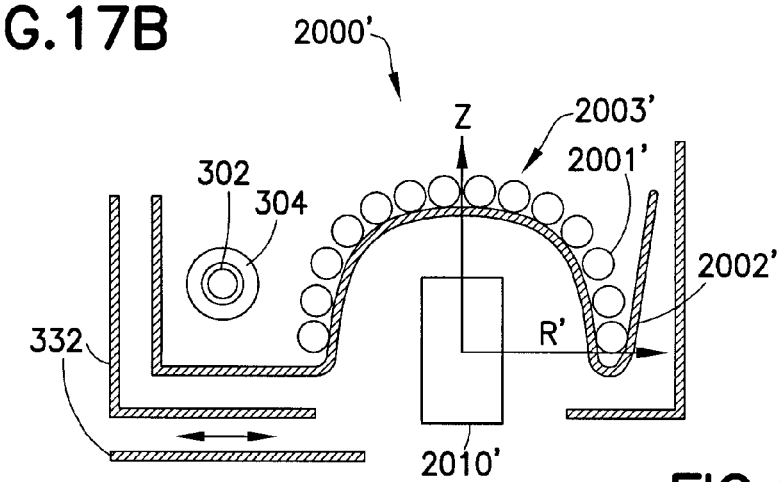

To overcome this difficulty a radiation detection system 2000', as shown in FIGS. 17A, 17B, and 17C according to an inventive embodiment of this disclosure, tray 2002' may be shaped to hold fluid path segment or coiled tubing segment 2001' so that they the coils lie along surfaces of "equal sensitivity" for radiation detector 2010'. For simplicity, radiation detector 2010' and the individual geometrical shapes shown in FIGS. 17A, 17B, and 17C are assumed to be cylindrically symmetrical, although this disclosure is not intended to be limited to shapes with this property. For each radiation detector 2010', the geometry of the radiation detector 2010' has a surface that is a function of R and Z axes such that anywhere on that surface, a small volume of radioactive fluid will give the same measurement of radioactivity at the radiation detector 2010'. In FIG. 17A, the center coil elements of coiled tubing segment 2001' are moved back a little from the surface of the radiation detector 2010' to achieve this effect. If the radiation detector 2010' is a small spherical detector, then the equal sensitivity surface is a sphere around the center of the radiation detector 2010', as illustrated in FIG. 17B. FIG. 17C illustrates a coiled tubing segment 2001' arranged in a cap shape which can be put onto or over the radiation detector 2010'. This geometry has benefits for ease of installing the tray 2003' and for overall fluid path design of the system 2000' which can more readily be done in a planar cassette to ease manufacture, assembly, and user interfacing. As shown in FIG. 17C, this tray could be placed in container body 332, and the dosimeter or radiation detector 2010' could either be part of the container body 332 or there could be a hole in the container body 332 which can be opened to allow the dosimeter to penetrate the container and measure the dose in the fluid path element 2003'. The opening could be covered by shielding when it is not in use to measure radiation and be arranged so that it can be opened and closed without exposing the operator to any radiation.

Even when the coil tubing segment 2001' is designed to be on an equal sensitivity surface of the radiation detector 2010', there will be variation of this surface geometry from radiation detector to radiation detector and there will be variation of the fluid path geometry from module 2003' to module 2003' due to manufacturing variation in the tray 2002' or the coiled tubing segment 2001'. One way to overcome this variation with a small injection bolus in the coiled tubing segment 2001' is to measure the radiation at two or more positions in the coiled tubing segment 2001' and average the readings to average out errors. This operation may be done by moving the injection bolus into position, stopping to take a measurement, moving to another position, stopping and measuring again, and so on until the desired number of measurements has been made. Or, this operation may be done by slowly moving the injection bolus through the coiled tubing segment 2001' and taking a time series of measurement as it flows through the coiled tubing segment 2001'.

An alternative embodiment for measuring the radioactivity before injecting a radioactive fluid into a patient or before putting the radioactive drug into, for example, hazardous fluid transport containers 1100 or 330 is to measure the radiation emanating from a small known and defined volume or geometry of the radioactive fluid. Once this concentration is known, by measuring the dose from a defined volume, the radiation dose dispensed or delivered is proportion to the concentration multiplied by the volume delivered. This is most easily illustrated in reference to shielded transport container 330 as shown in FIG. 15B. In FIG. 15B, which has the basic components described previously in connection with FIG. 15A, a radiation detector or sensor 2012 is arranged behind a small hole 2020 in radiation shielding 366. Generally surrounding the radiation detector is more shielding 364' to prevent the radiation detector 2012 from being affected by outside radiation. This small hole 2020 is arranged so that only radiation coming from a segment of the neck of syringe 302 strikes the radiation detector 2012. The syringe 302 is held in a repeatable and consistent geometric position within shielded transport container 330, for example, by detents, clips, or like structural elements (not shown). In operation, when the shielded transport container 330 is associated with an injector or other fluid pressurizing device for delivery, as in FIG. 5, the output of the radiation detector 2012 is communicated to a control unit 1442 associated with the injector or other pressurizing device which translates the radiation detection measurement into a radioactivity concentration using known designed sensitivity calibration. Injector control unit 1442 then causes the desired amount of drug to be injected into fluid path set 306, for example, by controllably moving piston pushrod 380, for subsequent delivery to the patient or, in the instance where the full volume is delivered manually, it can indicate for the record the concentration at the time of delivery. Control unit 1442 may also read and optionally write information from data storage device/memory unit 1899 as described previously. Alternately, the radiation detector 2012 and associated mechanical components and shielding 364' may be a reusable piece of equipment associated with the control unit 1442 and then the shielded transport container 330 would simply have a hole that is shielded except when in association with the radiation detector 2012, similar to that covered opening described above in relation to FIG. 17C. The measurement of the concentration of radioactive pharmaceutical is not limited to the neck of the syringe 302. It can also be done in other fluid path elements where the geometry with relation to the detector can be fixed and consistent and where radiation from nearby fluid container elements can be minimized to minimize interference. The radiation concentration measurement allows an accurate estimate or first guess of the volume to be drawn or delivered. The total dose can be measured and if necessary corrected after fluid motion.

The use of the various embodiments set forth in this disclosure, in combination or individually, has advantages in all delivery of radioactive drugs and all other medical fluids. For example, the bolus sharpening techniques of FIGS. 6 and 9 of this disclosure can be utilized in conjunction with the disclosure of International Application No. PCT/US07/89101 (WO 2008/083313), previously incorporated by reference, to provide tighter bolus performance.

While the embodiments of system, devices, and methods described hereinabove may in combination or individually be used to minimize the distortion of a test bolus injection and also improve the sharpness of an imaging bolus injection and, further, for the safe and efficient handling of hazardous fluids such as radiopharmaceutical fluids, those skilled in the art may make modifications and alterations to these embodiments without departing from the scope and spirit of the invention. The use of the embodiments set forth in this disclosure has advantages in all delivery of radioactive drugs and other medical fluids. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A hazardous radioactive fluid transport container, comprising:
    a portable housing;
    a first fluid path element disposed in the portable housing to conduct a radioactive fluid;
    one or more shield elements forming an enclosure surrounding the first fluid path element, each of the one or more shield elements being disposed within the portable housing;
    a second fluid path element disposed in the portable housing, wherein the second fluid path element is in fluid connection with the first fluid path element; and
    a third fluid path element in fluid connection with the first fluid path element and the second fluid path element, the third fluid path element provided to conduct a flushing fluid;
    wherein at least one of the first fluid path element, the second fluid path element, and the third fluid path element is accessible from outside the portable housing,
    wherein at least one of the first fluid path element, the second fluid path element, and the third fluid path element comprises coiled tubing paid outward from the portable housing and returned therein, and
    wherein the first fluid path element is filled with the radioactive fluid and the third fluid path element is filled with the flushing fluid, both filled via respective connectors for connecting to an outside radioactive fluid source and an outside flushing fluid source, respectively.

2. The radioactive fluid transport container of claim 1, further comprising at least one of a radiation detector and an air detector associated with one or more of the first fluid path element, the second fluid path element, and the third fluid path element.

3. The radioactive fluid transport container of claim 1, further comprising at least one control valve operably connected to one or more of the first fluid path element, the second fluid path element, and the third fluid path element.

4. The radioactive fluid transport container of claim 1, wherein the first fluid path element is a syringe.

5. A radioactive fluid delivery system, comprising:
    a portable housing enclosing an at least partially radiation shielded enclosure;
    a first fluid path element disposed in the shielded enclosure to conduct a radioactive fluid;
    a second fluid path element disposed in the portable housing and in fluid connection with the first fluid path element;
    a third fluid path element in fluid connection with the first fluid path element and the second fluid path element, the third fluid path element provided to conduct a flushing fluid; and
    a pump unit in controlled fluid connection with one or more of the first fluid path element and the third fluid path element, wherein the pump unit is configured to dispense fluid from one or more of the first fluid path element and the third fluid path element,
    wherein at least one of the first fluid path element, the second fluid path element, and the third fluid path element comprises coiled tubing paid outward from the portable housing and returned therein, and
    wherein the first fluid path element is filled with the radioactive fluid and the third fluid path element is filled with the flushing fluid, both filled via respective connectors for connecting to an outside radioactive fluid source and an outside flushing fluid source, respectively.

6. The radioactive fluid delivery system of claim 5, further comprising at least one of a radiation detector and an air detector associated with one or more of the first fluid path element, the second fluid path element, and the third fluid path element.

7. A method for priming a radiopharmaceutical delivery system and delivering a compact radiopharmaceutical drug bolus to a patient, the method comprising:
    delivering a first liquid to a fluid path element;
    delivering a fluid separator to the fluid path element;
    delivering a radiopharmaceutical drug to the fluid path element whereby the first liquid and the radiopharmaceutical drug are separated by the fluid separator flowing with the first liquid and the radiopharmaceutical drug to maintain separation between the first liquid and the radiopharmaceutical drug for bolus sharpness of the compact radiopharmaceutical drug bolus; and
    delivering the compact radiopharmaceutical drug bolus to the patient.

8. The method of claim 7, wherein the first liquid comprises a non-hazardous liquid.

9. The method of claim 7, wherein the fluid separator comprises a gas.

10. The method of claim 9, wherein the gas comprises carbon dioxide.

11. The method of claim 7, wherein the fluid separator comprises a liquid.

12. The method of claim 7, wherein the fluid separator comprises a solid member.

13. A radioactive fluid filling and transport system, comprising:
    a radioactive fluid transport container, comprising:
        a portable housing;
        a first fluid path element disposed in the portable housing to conduct a radioactive fluid;
        one or more shield elements forming an enclosure surrounding the first fluid path element, each of the one or more shield elements being disposed within the portable housing;
        a second fluid path element disposed in the portable housing and fluidly connected to the first fluid path element; and
        a third fluid path element in fluid connection with the first fluid path element and the second fluid path element, the third fluid path element provided to conduct a flushing fluid; and
    a filling system comprising at least a radioactive fluid source in reversible fluid connection with at least the first fluid path element; at least a flushing fluid source in reversible fluid connection with at least the third fluid path element; and at least one fluid pump associated with one or more of the at least a radioactive fluid source and the at least a flushing fluid source for dispensing fluid from the radioactive fluid source and the flushing fluid source into the first fluid path element and third fluid path element, respectively, wherein at least one of the first fluid path element, the second fluid path element, and the third fluid path element comprises coiled tubing be paid outward from the housing and returned therein, and wherein the first fluid path element is filled with the radioactive fluid and the third fluid path element is filled with the flushing fluid, both filled via respective connectors on the first fluid path element and the third fluid path element which are adapted to mate with mating connectors on the filling system.

14. The radioactive fluid filling and transport system of claim 13, wherein the one or more shield elements comprise a radiation shield.

15. The radioactive fluid filling and transport system of claim 13, further comprising at least one of a radiation detector and an air detector associated with one or more of the first fluid path element, the second fluid path element, and the third fluid path element.

16. The radioactive fluid filling and transport system of claim 2, further comprising a control valve in fluid connection with the at least a radioactive fluid source and the first fluid path element.

17. A system for dispensing pharmaceuticals, comprising:
a transport container comprising:
  a portable housing;
  a first fluid path element disposed in the portable housing to conduct a radioactive fluid;
  one or more shield elements forming an enclosure surrounding the first fluid path element, each of the one or more shield elements being disposed within the portable housing;
  a second fluid path element disposed in the portable housing, wherein the second fluid path element is in fluid connection with the first fluid path element; and
  a third fluid path element in fluid connection with the first fluid path element and the second fluid path element, the third fluid path element provided to conduct a flushing fluid,
  wherein at least one of the first fluid path element, the second fluid path element, and the third fluid path element comprises tubing accessed from outside the housing and paid outward from the housing and returned therein; and
a filling station comprising:
  a radioactive fluid source in fluid connection with at least a first filling station fluid path element terminating in a first mating connector configured to reversibly connect to a first connector element on the first fluid path element; a flushing fluid source in fluid connection with at least a second filling station fluid path element terminating in a second mating connector configured to reversibly connect to a second connector element on the third fluid path element;
  one or more fluid pump units; and
  a control unit operably connected to the one or more fluid pump units and configured to control the one or more fluid pump units.

18. The system of claim 17, further comprising one or more check valves operably connected to the second fluid path element.

19. The system of claim 17, further comprising one or more control valves fluidly connected to one or more of the at least a first filling station fluid path element, wherein the one or more control valves are operably connected to the control unit.

20. The system of claim 17, further comprising one or more data storage devices associated with one or more of the radioactive fluid source and the flushing fluid source.

21. The system of claim 17, wherein the filling station further comprises a waste container.

22. The system of claim 17, further comprising a carbon dioxide source conduit fluidly connected to a carbon dioxide source and the at least a first filling station fluid path element.

23. The system of claim 17, wherein the first fluid path element is a syringe.

* * * * *

UNITED STATES PATENT AND TRADEMARK OFFICE
CERTIFICATE OF CORRECTION

PATENT NO. : 9,056,200 B2
APPLICATION NO. : 12/996520
DATED : June 16, 2015
INVENTOR(S) : Uber III et al.

Page 1 of 1

It is certified that error appears in the above-identified patent and that said Letters Patent is hereby corrected as shown below:

IN THE SPECIFICATION:
In Column 14, Line 42, delete "and or" and insert -- and/or --, therefor.
In Column 20, Line 60, delete "container 1110," and insert -- container 1100, --, therefor.
In Column 32, Line 67, delete "inlet fluid path element 314" and insert -- inlet fluid path element 310 --, therefor.
In Column 35, Line 41, delete "tray 2003'" and insert -- tray2002'--, therefor.

IN THE CLAIMS:
In Column 37, Line 15, in Claim 1, delete "A hazardous radioactive" and insert -- A radioactive --, therefor.
In Column 38, Line 61, in Claim 13, delete "system comprising" and insert -- system, comprising: --, therefor.
In Column 39, Line 6, in Claim 13, delete "be paid" and insert -- paid --, therefor.
In Column 39, Line 21, in Claim 16, delete "of claim 2," and insert -- of claim 13 --, therefor.

Signed and Sealed this
Eighth Day of March, 2016

Michelle K. Lee
*Director of the United States Patent and Trademark Office*